US010612037B2

(12) United States Patent
Bowen et al.

(10) Patent No.: US 10,612,037 B2
(45) Date of Patent: Apr. 7, 2020

(54) INSECTICIDAL PROTEINS TOXIC OR INHIBITORY TO HEMIPTERAN PESTS

(71) Applicant: Monsanto Technology LLC, St. Louis, MO (US)

(72) Inventors: David J. Bowen, Wildwood, MO (US); Catherine A. Chay, Ballwin, MO (US); Arlene R. Howe, Clarkson Valley, MO (US); Jennifer L. Lutke, Ballwin, MO (US); Eric Van Fleet, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 204 days.

(21) Appl. No.: 15/627,164

(22) Filed: Jun. 19, 2017

(65) Prior Publication Data

US 2018/0002386 A1 Jan. 4, 2018

Related U.S. Application Data

(60) Provisional application No. 62/352,136, filed on Jun. 20, 2016.

(51) Int. Cl.
*C12N 15/82* (2006.01)
*C07K 14/32* (2006.01)
*A01N 63/02* (2006.01)
*A01N 37/46* (2006.01)

(52) U.S. Cl.
CPC ......... *C12N 15/8286* (2013.01); *A01N 37/46* (2013.01); *A01N 63/02* (2013.01); *C07K 14/32* (2013.01); *Y02A 40/162* (2018.01)

(58) Field of Classification Search
None
See application file for complete search history.

(56) References Cited

U.S. PATENT DOCUMENTS

| 5,723,440 | A | 3/1998 | Stockhoff et al. |
|---|---|---|---|
| 5,885,963 | A | 3/1999 | Stockhoff et al. |
| 5,942,658 | A | 8/1999 | Donovan et al. |
| 7,473,821 | B2 | 1/2009 | Abad et al. |
| 7,524,810 | B1 | 4/2009 | Schnepf |
| 7,615,686 | B2 | 11/2009 | Miles et al. |
| 7,674,959 | B2 | 3/2010 | Carozzi et al. |
| 8,318,900 | B2 | 11/2012 | Sampson et al. |
| 8,513,493 | B2 | 8/2013 | Baum et al. |
| 8,609,936 | B2 | 12/2013 | Baum et al. |
| 2006/0021087 | A1 | 1/2006 | Baum et al. |

FOREIGN PATENT DOCUMENTS

| WO | WO/1993/014205 | 7/1993 |
|---|---|---|
| WO | WO/1996/039843 | 12/1996 |
| WO | WO/2001/071042 | 9/2001 |
| WO | WO/2002/078437 | 10/2002 |
| WO | WO/2005/110068 | 11/2005 |
| WO | WO/2006/107761 | 10/2006 |
| WO | WO/2007/027776 | 3/2007 |
| WO | WO/2008/134072 | 11/2008 |
| WO | WO/2010/025320 | 3/2010 |
| WO | WO/2010/099365 | 9/2010 |

OTHER PUBLICATIONS

GenBank Accession #EEM68354, 2009.*
Guo et al, 2004, Proc. Natl. Acad. Sci. USA 101: 9205-9210.*
Argolo-Filho et al, 2014, Insects 5:62-91.*
Argôlo-Filho et al., "*Bacillus thuringiensis* is an environmental pathogen and host-specificity has developed as an adaptation to human-generated ecological niches," *Insects* 5(1):62-91; 2014.
Baum et al., "Binary toxins from *Bacillus thuringiensis* active against the western corn rootworm, *Diabrotica virgifera virgifera* LeConte," *Appl Environ Microbiol* 70(8):4889-4898; 2004.
Chan et al., "Unusual amino acid determinants of host range in the Mtx2 family of mosquitocidal toxins," *J Biol Chem* 271(24):14183-14187; 1996.
Chougule et al., "Toxins for transgenic resistance to hemipteran pests," *Toxins (Basel)* 4(6):405-429; 2012.
Crickmore et al., "Revision of the nomenclature for the *Bacillus thuringiensis* pesticidal crystal proteins," 62(3):807-813; 1998.
Donovan et al., "Characterization of two genes encoding *Bacillus thuringiensis* insecticidal crystal proteins toxic to *Coleoptera* species," *Appl Environ Microbiol* 58(12):3921-3927; 1992.
EBI Accession No. GSP: ABB68459, "Drosophila Melanogaster Polypeptide SEQ ID No. 32169. DYDERPSKRP RGKPTAGTAG RKISPRKPGR VEERRSNFNED RPLGRRRSEK ERTTPSSALD," XP 002600478, Mar. 2002, Database Geneseq.
EMBL Accession DQ836184, "Bacillus thuringiensis strain F14-1 Cry51Aa1 (cry51Aa1) gene, complete CDs," created on Aug. 1, 2007.
Extended European Search Report for European Patent Application No. 13772577.6, dated Sep. 14, 2015.
Extended European Search Report for European Patent Application 08754143.9, dated Oct. 6, 2010.
GenBank Accession No. DQ836184, "Bacillus thuringiensis strain F14-1 Cry51Aa1 (cry51 Aa1) gene, complete cds," Aug. 1, 2007.
Höfte et al., "Insecticidal crystal proteins of *Bacillus thuringiensis*," *Microbiol Rev* 53(2):242-255; 1989.
Huang et al., "Microbial control and biotechnology research on Bacillus thuringiensis in China," *J Invertebr Pathol* 95(3)175-180; 2007.

(Continued)

*Primary Examiner* — Anne Kubelik
(74) *Attorney, Agent, or Firm* — Dentons US LLP; Timothy Ball; Carine Doyle

(57) ABSTRACT

Nucleotide sequences are disclosed encoding novel, insecticidal TIC4747 and related proteins exhibiting Hemipteran and Lepidopteran inhibitory activity, as well as fragments thereof. Particular embodiments provide compositions and transformed plants, plant parts, and seeds containing a polynucleotide construct encoding one or more of the toxin proteins within the TIC4747-related protein toxin class.

22 Claims, No Drawings

Specification includes a Sequence Listing.

(56) References Cited

OTHER PUBLICATIONS

International Search Report and Written Opinion for PCT/US2008/005542, dated Nov. 24, 2008.
Lambert et al., "Novel *Bacillus thuringiensis* insecticidal crystal protein with a silent activity against coleopteran larvae," *Appl Environ Microbiol* 58(8):2536-2542; 1992.
Liu et al., "New gene from nine *Bacillus sphaericus* strains encoding highly conserved 35.8-kilodalton mosquitocidal toxins," *Appl Environ Microbiol* 62(6):2174-2176; 1996.
NCBI Accession No. DQ836184, "Bacillus Thuringiensis Strain F14-1 Cry51Aa1 (cry51Aa1) Gene", obtained on Oct. 1, 2010.
NCBI Sample GenBank Record, obtained Oct. 1, 2010.
Palma et al., "*Bacillus thuringiensis* toxins: An overview of their biocidal activity," *Toxins (Basel)* 6(12):3296-3325; 2014.
Soberón et al., "Engineering modified Bt toxins to counter insect resistance," *Science* 318(5856):1640-1642; 2007.
Thanabalu et al., "A Bacillus sphaericus gene encoding a novel type of mosquitocidal toxin of 31.8 kDa," *Gene* 170(1):85-89; 1996.
Vita et al., "Scorpion toxins as natural scaffolds for protein engineering," *Proc Natl Acad Sci U S A* 92(14):6404-6408; 1995.
Von Tersch et al., "Membrane-permeabilizing activities of *Bacillus thuringiensis* coleopteran-active toxin CryIIIB2 and CryIIIB2 domain I peptide," *Appl Environ Microbiol* 60(10):3711-3717; 1994.
Wellman-Desbiens et al., "Development of a *Bacillus thuringiensis*-based assay on *Lygus hesperus,*" *J Econ Entomol* 98(5):1469-1479; 2005.

* cited by examiner

INSECTICIDAL PROTEINS TOXIC OR INHIBITORY TO HEMIPTERAN PESTS

REFERENCE TO RELATED APPLICATION

This application claims the benefit of U.S. Provisional Application No. 62/352,136, filed Jun. 20, 2016, which is herein incorporated by reference in its entirety.

INCORPORATION OF SEQUENCE LISTING

The file named "38_21_61965_0001_ST25.txt" containing a computer-readable form of the Sequence Listing was created on May 22, 2017. This file is 220,940 bytes in size (as measured in the MS-Windows® operating system), filed contemporaneously with this application by electronic submission (using the United States Patent Office EFS-Web filing system), and is incorporated herein by reference in its entirety.

FIELD OF THE INVENTION

The invention generally relates to the field of insect inhibitory proteins. A novel class of insecticidal proteins exhibiting insect inhibitory activity against agriculturally-relevant pests of crop plants and seeds is disclosed in this application. In particular, the disclosed class of proteins exhibits insecticidal activity against agriculturally-relevant pests of crop plants and seeds, particularly the Hemipteran order of insect pests. Plants, plant parts, and seeds containing a recombinant nucleic acid molecule encoding one or more of the disclosed toxin proteins are provided.

BACKGROUND OF THE INVENTION

Improving crop yield from agriculturally-significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts with respect to food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Hemiptera, are considered a major cause of damage to field crops, thereby decreasing crop yields in infested areas. Hemipteran pest species which negatively impact agriculture include, but are not limited to, stink bug, Western tarnished plant bug and Tarnished plant bug.

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for insecticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of other bacterial species, such as *Brevibacillus laterosporus, Lysinibacillus sphaericus* ("Ls" formerly known as *Bacillus sphaericus*) and *Paenibacillus popilliae*.

Crystalline and secreted soluble insecticidal protein toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal proteins has been globally adopted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal proteins used in these crops has created a selection pressure for existing insect alleles that impart resistance to the currently-utilized insecticidal proteins.

Hemipteran pests injure plants by puncturing tissues with their piercing and sucking mouthparts and then extracting plant fluids. The principle damage to tissues comes from loss of plant fluids and injection of digestive enzymes. The puncture sites can be predisposed to colonization by pathogenic organisms, causing significant yield and quality loss. One family in the order of Hemiptera, Pentatomidae, has many members commonly referred to as Stink Bugs. Certain species of Stink Bugs that are agricultural pests have become difficult to control with insecticidal chemicals due to the emergence of resistant populations.

Various characteristics of Stink Bugs result in a high susceptibility to resistance emergence. For example, Stink Bugs can have multiple generations in a single growing season. Further, they can overwinter as adults almost anywhere where they can be protected (including homes), and then begin feeding on various host plants as the temperatures rise. Once development begins, Stink Bugs have two to three generations, depending on the species and host plants.

On corn, Stink Bugs are most often found feeding on young plants in late spring and early summer. Feeding at this time results in holes in the leaf, and if severe, results in deformed plants. The Brown Stink Bug is the primary Stink Bug pest for corn crops during the early vegetative stages.

The Brown Marmorated Stink Bug, another corn pest, is generally found in late summer on corn usually feeding on the ear, directly destroying the kernels. This is especially a concern on sweet corn and can be quite damaging.

On soybean, most of the injury from Stink Bugs occurs during second half of the growing season when significant feeding takes place on pods and developing seed. Darkish spots will occur where the mouthparts puncture the plant tissue, although these are difficult to see. This can cause deformation and abortion of the seeds, as well as provide a route for infection by pathogenic organisms. Stink Bug feeding on soybean often results in delayed leaf maturity and foliage retention. During seed formation, seeds will become shriveled, deformed, undersized, and even be aborted. Feeding on more developed seeds will result in minor shriveling and discoloration. This not only negatively affects yield, but also will result in lower market value or inhibit the sale of produced seed.

Due to warming temperatures, stink bugs are expanding their population size and geographical range in the United States. Due to the damage on agricultural crops inflicted by stink bugs, their high susceptibility to the emergence there is a need to find new and novel insect toxins that are effective against Hemipteran insect pests such as stink bugs.

SUMMARY OF THE INVENTION

The present invention provides a novel class of insect inhibitory polypeptides (insect toxic proteins) which are shown to exhibit inhibitory activity against several hemipteran pests of crop plants. Each of the proteins can be used alone or in combination with each other and with other Bt proteins and toxic agents in formulations and in planta, providing alternatives to known Bt proteins and insecticide chemistries.

In one embodiment, a recombinant nucleic acid molecule is disclosed comprising a heterologous promoter fragment operably linked to a polynucleotide segment encoding a pesticidal protein or fragment thereof, wherein said pesticidal protein or pesticidal fragment thereof (a) comprises the amino acid sequence of SEQ ID NO:12, SEQ ID NO:2, SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:22, SEQ ID NO:24, SEQ ID NO:26, or SEQ ID NO:28; or (b) comprises an amino acid sequence having at least from about 62% to about 100% amino acid sequence identity, or any fraction percentage point between 62% and 100%, to the proteins selected from the group consisting of SEQ ID NO:12, SEQ ID NO:2, SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:22, SEQ ID NO:24, SEQ ID NO:26, and SEQ ID NO:28. In another embodiment, said polynucleotide segment hybridizes to a polynucleotide having the nucleotide sequence of SEQ ID NO:11, SEQ ID NO:1, SEQ ID NO:3, SEQ ID NO:5, SEQ ID NO:7, SEQ ID NO:9, SEQ ID NO:13, SEQ ID NO:15, SEQ ID NO:17, SEQ ID NO:19, SEQ ID NO:21, SEQ ID NO:23, SEQ ID NO:25, or SEQ ID NO:27 under hybridization conditions of 68° C., followed by washing at 68° C., in 2×SSC containing 0.1% SDS; or (b) said recombinant nucleic acid molecule is in operable linkage with a vector, and said vector is selected from the group consisting of a plasmid, phagemid, bacmid, cosmid, and a bacterial or yeast artificial chromosome. The recombinant nucleic acid molecule can comprise a sequence that functions to express the pesticidal protein in a plant; or is expressed in a plant cell to produce a pesticidally effective amount of pesticidal protein.

In another embodiment, host cells are provided which contain at least one recombinant nucleic acid molecule disclosed herein, wherein the host cell is selected from the group consisting of a bacterial, a yeast, and a plant cell. Bacterial host cells include at least species such as *Agrobacterium, Rhizobium, Bacillus, Brevibacillus, Escherichia, Pseudomonas, Klebsiella*, and *Erwinia*. The *Bacillus* species is a *Bacillus cereus* or a *Bacillus thuringiensis*, the *Brevibacillus* is a *Brevibacillus laterosperous*, and said *Escherichia* is an *Escherichia coli*. Yeast host cells include at least *Pichya* and *Saccharomyces* species. Plant host cells include at least dicotyledonous plant cells and monocotyledonous plant cells, and as applicable, further include at least an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cells.

In another embodiment, the pesticidal protein exhibits activity against an insect species of the order Hemiptera, including *Chinavia hilaris, Chinavia marginata, Chinavia pensylvanica, Chlorochroa granulose, Chlorochroa kanei, Chlorochroa ligata, Chlorochroa lineate, Chlorochroa opuntiae, Chlorochroa persimilis, Chlorochroa rossiana, Chlorochroa sayi, Chlorochroa uhleri, Chlorochroa belfragii, Chlorochroa faceta, Chlorochroa osborni, Chlorochroa saucia, Chlorochroa senilis, Nezara viridula, Edessa meditabunda, Edessa bifida, Edessa florida, Euschistus heros, Euschistus acuminatus, Euschistus biformis, Euschistus conspersus, Euschistus crenator, Euschistus egglestoni, Euschistus ictericus, Euschistus inflatus, Euschistus latimarginatus, Euschistus obscures, Euschistus politus, Euschistus quadrator, Euschistus sevus, Euschistus strenuous, Euschistus tristigmus, Euschistus variolarius Halyomorpha halys, Thyanta accerra, Thyanta calceata, Thyanta custator, Thyanta pallidovirens, Thyanta perditor, Thyanta maculate, Thyanta pseudocasta Dichelops melacanthus, Dichelops avilapiresi, Dichelops bicolor, Dichelops dimidatus, Dichelops furcatus, Dichelops furcifrons, Dichelops lobatus, Dichelops miriamae, Dichelops nigrum, Dichelops peruanus, Dichelops phoenix, Dichelops saltensis, Piezodorus guildinni, Piezodorus lituratus Megacopta cribraria, Lygus hesperus*, and *Lygus lineolaris*.

Also provided are plants comprising a recombinant nucleic acid molecule comprising a polynucleotide segment corresponding to a heterologous promoter operably linked to a segment encoding a pesticidal protein or pesticidal fragment thereof, wherein: (a) said pesticidal protein or pesticidal fragment thereof comprises the amino acid sequence of SEQ ID NO:12, SEQ ID NO:2, SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:22, SEQ ID NO:24, SEQ ID NO:26, or SEQ ID NO:28; or (b) said pesticidal protein or pesticidal fragment thereof comprises an amino acid sequence having at least from about 62% to about 100% amino acid sequence identity, or any fraction percentage point between 62% and 100%, to the proteins selected from the group consisting of SEQ ID NO:12, SEQ ID NO:2, SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:22, SEQ ID NO:24, SEQ ID NO:26, and SEQ ID NO:28; or (c) said polynucleotide segment hybridizes under stringent hybridization conditions to a polynucleotide having the nucleotide sequence of SEQ ID NO:11, SEQ ID NO:1, SEQ ID NO:3, SEQ ID NO:5, SEQ ID NO:7, SEQ ID NO:9, SEQ ID NO:13, SEQ ID NO:15, SEQ ID NO:17, SEQ ID NO:19, SEQ ID NO:21, SEQ ID NO:23, SEQ ID NO:25, or SEQ ID NO:27 under hybridization conditions of 68° C., followed by washing at 68° C., in 2×SSC containing 0.1% SDS; or (d) said plant exhibits a detectable amount of said pesticidal protein, wherein the pesticidal protein is chosen from the group consisting of SEQ ID NO:12, SEQ ID NO:2, SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:22, SEQ ID NO:24, SEQ ID NO:26, and SEQ ID NO:28.

In one embodiment, the plant is either a dicotyledonous plant or a monocotyledonous plant. In another embodiment, the plant is further selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In a further embodiment, seeds comprising the recombinant nucleic acid molecules are disclosed.

In another embodiment, an insect inhibitory composition is provided comprising the recombinant nucleic acid molecules as set forth herein. The insect inhibitory composition can further comprise a nucleotide sequence encoding at least one other pesticidal agent that is different from said pesticidal protein. In certain embodiments, the at least one other pesticidal agent is selected from the group consisting of an insect inhibitory protein, an insect inhibitory dsRNA molecule, and an ancillary protein. The at least one other pesticidal agent in the insect inhibitory composition exhibits activity against one or more pest species of the orders Lepidoptera, Coleoptera, Hemiptera, Homoptera, or Thysanoptera. The at least one other pesticidal agent in the insect inhibitory composition is selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC3131, TIC2160, VIP3A, VIP3B, VIP3Ab, AXMI-001, AXMI-002, AXMI-030, AXMI-035, AXMI-036, AXMI-045, Axmi52, Axmi58, Axmi88, Axmi97, Axmi102, Axmi112, Axmi117, Axmi100, AXMI-115, AXMI-113, and AXMI-005, AXMI134, AXMI-150, Axmi171, AXMI-184, axmi196, axmi204, axmi207, axmi209, Axmi205, AXMI218, AXMI220, AXMI221z, AXMI222z, AXMI223z, AXMI224z and AXMI225z, AXMI238, AXMI270, AXMI279, AXMI335, AXMI345, AXMI-R1, and variants thereof, IP3 and variants thereof, DIG-3, DIG-5, DIG-10, DIG-11, DIG-657 protein, PHI-4 variants, PIP-72 variants, PIP-45 variants, PIP-64 variants, PIP-74 variants, PIP-77 variants, DIG-305, PIP-47 variants, DIG-17, DIG-90, DIG-79, and DIG-303.

Commodity products are provided comprising a detectable amount of the recombinant nucleic acid molecules disclosed herein. Such commodity products include commodity corn which may be bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of this application, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

Also contemplated is a method of producing seed comprising one or more of the recombinant nucleic acid molecules disclosed herein. The method includes planting at least one such seed; growing a plant from the seed; and harvesting progeny seed from the plant, wherein the harvested seed comprises the one or more recombinant nucleic acid molecules.

In another embodiment, a plant resistant to insect infestation is provided. The cells of said plant optionally comprise: (a) a recombinant nucleic acid molecule encoding an insecticidally effective amount of a pesticidal protein as set forth in SEQ ID NO:12, SEQ ID NO:2, SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:22, SEQ ID NO:24, SEQ ID NO:26, or SEQ ID NO:28; or (b) an insecticidally effective amount of a protein comprising an amino acid sequence having at least 62%, or 65%, or 70%, or 80%, or 85%, or 90%, or 95%, or about 100% amino acid sequence identity to SEQ ID NO:12, SEQ ID NO:2, SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:22, SEQ ID NO:24, SEQ ID NO:26, or SEQ ID NO:28.

Also disclosed are methods for controlling a Lepidopteran species pest, and controlling a Hemipteran species pest infestation of a plant, particularly a crop plant. The method will comprise contacting the pest with an insecticidally effective amount of a pesticidal proteins as set forth in SEQ ID NO:12, SEQ ID NO:2, SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:22, SEQ ID NO:24, SEQ ID NO:26, or SEQ ID NO:28; or contacting the pest with an insecticidally effective amount of one or more pesticidal proteins comprising an amino acid sequence having at least 62%, or 65%, or 70%, or 80%, or 85%, or 90%, or 95%, or about 100% amino acid sequence identity to SEQ ID NO:12, SEQ ID NO:2, SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:22, SEQ ID NO:24, SEQ ID NO:26, or SEQ ID NO:28.

BRIEF DESCRIPTION OF THE SEQUENCES

SEQ ID NO:1 is the nucleotide sequence encoding the TIC4747 toxin protein obtained from *Bacillus thuringiensis* (Bt) species CFB007452.

SEQ ID NO:2 is the amino acid sequence of TIC4747 protein.

SEQ ID NO:3 is the nucleotide sequence encoding the TIC7181 toxin protein obtained from Bt species EG9737.

SEQ ID NO:4 is the amino acid sequence of TIC7181 protein.

SEQ ID NO:5 is the nucleotide sequence encoding the TIC4904 toxin protein obtained from Bt species CFB007432.

SEQ ID NO:6 is the amino acid sequence of TIC4904 protein.

SEQ ID NO:7 is the nucleotide sequence encoding the TIC6547 toxin protein obtained from Bt species CFB231019.

SEQ ID NO:8 is the amino acid sequence of TIC6547 protein.

SEQ ID NO:9 is the native nucleotide sequence encoding the TIC4006 toxin protein obtained from Bt species WC12466.

SEQ ID NO:10 is the amino acid sequence of TIC4006 protein.

SEQ ID NO:11 is a synthetic coding sequence encoding a TIC4747PL pesticidal protein designed for expression in a plant cell wherein an additional alanine codon is inserted immediately following the initiating methionine codon.

SEQ ID NO:12 is the amino acid sequence of TIC4747PL encoded by a synthetic coding sequence designed for expression in a plant cell (SEQ ID NO:11), and wherein an additional alanine amino acid is inserted immediately following the initiating methionine.

SEQ ID NO:13 is a synthetic coding sequence encoding a TIC7181PL pesticidal protein designed for expression in a plant cell wherein an additional alanine codon is inserted immediately following the initiating methionine codon.

SEQ ID NO:14 is the amino acid sequence of TIC7181PL encoded by a synthetic coding sequence designed for expression in a plant cell (SEQ ID NO:13), and wherein an additional alanine amino acid is inserted immediately following the initiating methionine.

SEQ ID NO:15 is a synthetic coding sequence encoding a TIC4904PL pesticidal protein designed for expression in a plant cell wherein an additional alanine codon is inserted immediately following the initiating methionine codon.

SEQ ID NO:16 is the amino acid sequence of TIC4904PL encoded by a synthetic coding sequence designed for expression in a plant cell (SEQ ID NO:15), and wherein an additional alanine amino acid is inserted immediately following the initiating methionine.

SEQ ID NO:17 is a synthetic coding sequence encoding a TIC6547PL pesticidal protein designed for expression in a plant cell wherein an additional alanine codon is inserted immediately following the initiating methionine codon.

SEQ ID NO:18 is the amino acid sequence of TIC6547PL encoded by a synthetic coding sequence designed for expression in a plant cell (SEQ ID NO:17), and wherein an additional alanine amino acid is inserted immediately following the initiating methionine.

SEQ ID NO:19 is a synthetic coding sequence encoding a TIC4006PL pesticidal protein designed for expression in a plant cell wherein an additional alanine codon is inserted immediately following the initiating methionine codon.

SEQ ID NO:20 is the amino acid sequence of TIC4006PL encoded by a synthetic coding sequence designed for expression in a plant cell (SEQ ID NO:19), and wherein an additional alanine amino acid is inserted immediately following the initiating methionine.

SEQ ID NO:21 is a nucleotide sequence encoding TIC4747_His which is comprised of the TIC4747 coding sequence with a Histadine tag coding sequence operably linked 3' to the TIC4747 coding sequence.

SEQ ID NO:22 is the amino acid sequence of TIC4747 His.

SEQ ID NO:23 is a nucleotide sequence encoding TIC4904_His which is comprised of the TIC4904 coding sequence with a Histadine tag coding sequence operably linked 5' to the TIC4904 coding sequence.

SEQ ID NO:24 is the amino acid sequence of TIC4904 His.

SEQ ID NO:25 is a nucleotide sequence encoding TIC6547_His which is comprised of the TIC6547 coding sequence with a Histadine tag coding sequence operably linked 5' to the TIC6547 coding sequence.

SEQ ID NO:26 is the amino acid sequence of TIC6547_His.

SEQ ID NO:27 is a nucleotide sequence encoding TIC4006_His which is comprised of the TIC4006 coding sequence with a Histadine tag coding sequence operably linked 5' to the TIC4006 coding sequence.

SEQ ID NO:28 is the amino acid sequence of TIC4006_His.

DETAILED DESCRIPTION OF THE INVENTION

One problem in the art of agricultural pest control can be characterized as a need for new insecticidal proteins that are efficacious against target pests, exhibit broad spectrum toxicity against target pest species, are capable of being expressed in plants without causing undesirable agronomic issues, and provide an alternative mode of action compared to current toxins that are used commercially in plants.

Novel insecticidal proteins are disclosed herein, exemplified by TIC4747 and related family members that provide resistance to Hemipteran insect pests. Also disclosed are synthetic coding sequences designed for expression in a plant cell that encode a TIC4747PL and related family member toxin proteins in which an alanine amino acid residue is provided immediately following the initiating methionine residue to improve expression in the plant cell. Further disclosed are recombinant nucleic acid molecules comprising a promoter in operable linkage to a coding sequence encoding a TIC4747 or TIC4747PL toxin protein, or related family members, or fragment thereof.

Reference in this application to "TIC4747 proteins," "TIC4747 protein toxins," "TIC4747 toxin proteins," "TIC4747 pesticidal proteins," "TIC4747-related toxins," "TIC4747-related family members," "TIC4747-related protein toxin class or family," "TIC4747-related toxin proteins," "TIC4747-related toxin polypeptides," "TIC4747-related pesticidal proteins," "TIC4747 protein toxin class," "variants of TIC4747," or 'TIC4747 variants" and the like, refer to any novel insect inhibitory protein that comprises, that consists, that is substantially homologous to, that is similar to, or that is derived from the insect inhibitory polypeptide sequence of TIC4747 (SEQ ID NO:2), the insect inhibitory polypeptide sequence of TIC4747-related family members TIC7181 (SEQ ID NO:4), TIC4904 (SEQ ID NO:6), TIC6547 (SEQ ID NO:8) and TIC4006 (SEQ ID NO:10), plant-optimized polypeptides sequences of TIC474 or TIC4747-related family members, and insect inhibitory segments thereof, or combinations thereof, that confer activity against Hemipteran pests, including any protein exhibiting insect inhibitory activity if alignment of such protein with TIC4747 or TIC4747-related family members results in at least about 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% amino acid sequence identity (or any fraction percentage in this range).

The term “segment” or “fragment” is used in this application to describe consecutive amino acid or nucleic acid sequences that are shorter than the complete amino acid or nucleic acid sequence describing a disclosed TIC4747, TIC4747PL or related family member insecticidal protein. A segment or fragment exhibiting insect inhibitory activity is also disclosed in this application if alignment of such segment or fragment, with the corresponding section of the TIC4747 or TIC4747PL and related family member insecticidal protein, results in amino acid sequence identity of any fraction percentage from about 62 to about 100 percent between the segment or fragment and the corresponding section of the TIC4747 or TIC4747PL and related family member insecticidal protein.

Reference in this application to the terms “active” or “activity”, “pesticidal activity” or “pesticidal”, or “insecticidal activity”, “insect inhibitory” or “insecticidal” refer to efficacy of a toxic agent, such as an insecticidal protein, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the insecticidal protein) or killing (causing the morbidity, mortality, or reduced fecundity of) a pest. These terms are intended to include the result of providing a pesticidally effective amount of an insecticidal protein to a pest where the exposure of the pest to the insecticidal protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the insecticidal protein in or on the plant. In general, pesticidal activity refers to the ability of an insecticidal protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Hemiptera. The insecticidal protein can be produced by the plant or can be applied to the plant or to the environment within the location where the plant is located. The terms “bioactivity,” “effective,” “efficacious” or variations thereof are also terms interchangeably utilized in this application to describe the effects of the insecticidal proteins of the present invention on target insect pests.

A pesticidally effective amount of a toxic agent, when provided in the diet of a target pest, exhibits pesticidal activity when the toxic agent contacts the pest. A toxic agent can be an insecticidal protein or one or more chemical agents known in the art. Insecticidal chemical agents and insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Insecticidal protein agents include the insecticidal proteins set forth in this application, as well as other proteinaceous toxic agents including those that target Hemipteran pest species, as well as protein toxins that are used to control other plant pests such as Cry proteins available in the art for use in controlling *Lepidopteran, Coleopteran, Thysanopteranm* and *Homopteran* species.

It is intended that reference to a pest, particularly a pest of a crop plant, means insect pests of crop plants, particularly those Hemipteran insect pests that are controlled by the TIC4747 toxin protein class. However, reference to a pest can also include *Lepidopteran, Coleopteran, Homopteran*, and *Thysanopteran* insect pests of plants, as well as nematodes and fungi when toxic agents targeting these pests are co-localized or present together with a TIC4747-related insecticidal protein, or a protein that is 62 to about 100 percent identical to the insecticidal protein.

The insecticidal proteins of the TIC4747 protein toxin class are related by a common function and exhibit insecticidal activity towards insect pests from the Hemipteran insect species as well as the Lepidopteran insect species.

The insects of the order Hemiptera include, but are not limited to, Stink Bugs of the family Pentatomidae: Green Stink Bugs from the genus *Chinavia* (*Chinavia hilaris, Chinavia marginata*, and *Chinavia pensylvanica*), Stink bugs of the genus *Chlorochroa* (*Chlorochroa granulose, Chlorochroa kanei, Chlorochroa ligata, Chlorochroa lineate, Chlorochroa opuntiae, Chlorochroa persimilis, Chlorochroa rossiana, Chlorochroa sayi, Chlorochroa uhleri, Chlorochroa belfragii, Chlorochroa faceta, Chlorochroa osborni, Chlorochroa saucia*, and *Chlorochroa senilis*), Southern Green Stink Bug (*Nezara viridula*), Stink Bugs from the genus *Edessa* (*Edessa meditabunda, Edessa bifida*, and *Edessa florida*), the Neotropical Brown Stink Bug (*Euschistus heros*), stink bugs from the genus *Euschistus* (*Euschistus acuminatus, Euschistus biformis, Euschistus conspersus, Euschistus crenator, Euschistus egglestoni, Euschistus ictericus, Euschistus inflatus, Euschistus latimarginatus, Euschistus obscures, Euschistus politus, Euschistus quadrator, Euschistus sevus, Euschistus strenuous, Euschistus tristigmus*, and *Euschistus variolarius*), Brown Marmorated Stink Bug (*Halyomorpha halys*), Red-Shouldered Stink Bug (*Thyanta accerra*), stink bugs of the genus *Thyanta* (*Thyanta calceata, Thyanta custator, Thyanta pallidovirens, Thyanta perditor, Thyanta maculate*, and *Thyanta pseudocasta*), the Green Belly Stink Bug (*Dichelops melacanthus*) and other stink bugs of the genus *Dichelops* (*Dichelops avilapiresi, Dichelops bicolor, Dichelops dimidatus, Dichelops furcatus, Dichelops furcifrons, Dichelops lobatus, Dichelops miriamae, Dichelops nigrum, Dichelops peruanus, Dichelops phoenix*, and *Dichelops saltensis*), the Red Banded Stink Bug (*Piezodorus guildinni*) as well as *Piezodorus lituratus*; and insects of the family of Plataspidae such as Kudzu Bug (*Megacopta cribraria*), Western tarnished plant bug (*Lygus hesperus*), and Tarnished plant bug (*Lygus lineolaris*).

The insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), bertha armyworm (*Mamestra configurata*), black cutworm (*Agrotis ipsilon), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., cotton leaf worm (*Alabama argillacea*), fruit tree leaf roller (*Archips argyrospila*), European leafroller (*Archips rosana*) and other *Archips* species, Asiatic rice borer or rice stem borer (*Chilo suppressalis*), rice leaf roller (*Cnaphalocrocis medinalis*), corn root webworm (*Crambus caliginosellus*), bluegrass webworm (*Crambus teterrellus*), southwestern corn borer (*Diatraea grandiosella*), sugarcane borer (*Diatraea saccharalis*), spiny bollworm (*Earias insulana*), spotted bollworm (*Earias vittella*), American bollworm (*Helicoverpa armigera*), corn earworm or cotton bollworm (*Helicoverpa zea*), sod webworm (*Herpetogramma licarsisalis*), European grape vine moth (*Lobesia botrana*), citrus leafminer (*Phyllocnistis citrella*), large white butterfly (*Pieris brassicae*), imported cabbageworm, or small white butterfly (*Pieris rapae*), tobacco cutworm or cluster caterpillar (*Spodoptera litura*), and tomato leafminer (*Tuta absoluta*).

Reference in this application to an "isolated DNA molecule," or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further herein, an open reading frame (ORF) encoding TIC4747 (SEQ ID NO:1) was discovered in DNA obtained from *Bacillus thuringiensis* (Bt) species CFB007452. The coding sequence was cloned and expressed in microbial host cells to produce recombinant proteins used in bioassays. High throughput sequencing and bioinformatic techniques were used to screen microbial genomes for genes encoding proteins exhibiting similarity to TIC4747. The resulting proteins—TIC4904, TIC4006, TIC6547, and TIC7181—along with TIC4747, the polypeptides encoding these proteins, and the plant-optimized polypeptides and polynucleotides for these proteins constitute the TIC4747 protein toxin class. Bioassays using microbial host cell-derived proteins of TIC4747 demonstrated activity against the Hemipteran insect pest species Southern Green Stink Bug (*Nezara viridula*), Neotropical Brown Stink Bug (*Euschistus heros*), Western tarnished plant bug (*Lygus hesperus*), and Tarnished plant bug (*Lygus lineolaris*). The novel insecticidal protein, TIC6547 exhibits insecticidal activity against the Lepidopteran insect pest species Diamondback Moth (*Plutella xylostella*). The novel insecticidal protein, TIC7181 demonstrated activity against Tarnished plant bug (*Lygus lineolaris*).

It is contemplated that additional toxin protein sequences related to TIC4747 can be created by using the amino acid sequence of the proteins in the TIC4747 protein toxin class to create proteins with novel properties. Proteins from the TIC4747 protein toxin class can be aligned to combine differences at the amino acid level into novel amino acid sequence variants and making appropriate changes to the recombinant nucleic acid sequence encoding the variants.

It is further contemplated that improved variants of the TIC4747 toxin class can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

It is also contemplated that fragments of proteins in the TIC4747 protein toxin class can be truncated forms wherein one or more amino acids are deleted from the N-terminal end, C-terminal end, the middle of the protein or combinations thereof wherein the fragments and variants retain insect inhibitory activity. These fragments can be naturally occurring or synthetic variants of proteins in the TIC4747 protein toxin class or derived protein variants, but should retain the insect inhibitory activity of proteins in the TIC4747 protein toxin class.

Proteins that resemble TIC4747 and related family member insecticidal proteins can be identified by comparison to each other using various computer based algorithms known in the art (See Tables 1 and 2). For example, amino acid sequence identities of proteins related to the TIC4747 and related family member insecticidal proteins can be analyzed using a Clustal W alignment using these default parameters:

Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of the subject protein). Other alignment algorithms are also available in the art, provide results similar to those obtained using Clustal W alignment and are contemplated in this application.

It is intended that a query protein exhibiting insect inhibitory activity against a Hemipteran or Lepidopteran insect species is related to the TIC4747 protein toxin class if alignment of such query protein with the subject TIC4747 and related family member insecticidal proteins set forth in SEQ ID NOs:2, 4, 6, 8, 10, 12, 14, 16, 18, or 20 results in at least about 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% amino acid sequence identity (or any fraction percentage in this range) between the query and subject protein.

Exemplary proteins of TIC4747 (SEQ ID NO:2) and related family members TIC7181 (SEQ ID NO:4), TIC4904 (SEQ ID NO:6), TIC6547 (SEQ ID NO:8), and TIC4006 (SEQ ID NO:10) were aligned with each other using a Clustal W algorithm. A pair-wise matrix of percent amino acid sequence identities for each pair was created, as reported in Table 1.

TABLE 1

Pair-wise matrix display of exemplary proteins.

| Sequence | TIC4747 SEQ ID NO: 2 | TIC7181 SEQ ID NO: 4 | TIC4904 SEQ ID NO: 6 | TIC6547 SEQ ID NO: 8 | TIC4006 SEQ ID NO: 10 |
|---|---|---|---|---|---|
| TIC4747 | — | 99.9 (1216) | 94.2 (1147) | 93.1 (1133) | 82.3 (1001) |
| TIC7181 | 99.9 (1216) | — | 94.2 (1146) | 93 (1132) | 82.2 (1000) |
| TIC4904 | 94.2 (1147) | 94.2 (1146) | — | 93.3 (1135) | 81.8 (995) |
| TIC6547 | 93.6 (1133) | 93.5 (1132) | 93.7 (1135) | — | 82.8 (1003) |
| TIC4006 | 82.5 (1001) | 82.4 (1000) | 82 (995) | 82.7 (1003) | — |

In addition to percent identity, the TIC4747 and related family member proteins can also be related by primary structure (conserved amino acid motifs), by lengths (about 1211 to 1217 amino acids) and by other characteristics. Characteristics of TIC4747 and related family members are presented in Table 2 below.

As described further in the Examples of this application, a recombinant nucleic acid molecule sequences encoding the proteins of the TIC4747 protein toxin class were designed for use in plants. One exemplary plant-optimized recombinant nucleic acid molecule sequence encoding TIC4747 is TIC4747PL (SEQ ID NO:11). TIC4747PL has an additional alanine amino acid immediately following the initiating methionine relative to TIC4747. The additional alanine residue inserted into TIC4747 is believed to improve the expression of the protein in planta.

Expression cassettes and vectors containing the recombinant nucleic acid molecule sequence can be constructed and introduced into corn, soybean or cotton plant cells in accordance with transformation methods and techniques known in the art. For example, Agrobacterium-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), U.S. Pat. No. 7,026,528 (wheat), and U.S. Pat. No. 6,365,807 (rice), and in Arencibia et al. (1998) Transgenic Res. 7:213-222 (sugarcane) all of which are incorporated herein by reference in their entirety. Transformed cells can be regenerated into transformed plants that express proteins from the TIC4747 protein toxin class and demonstrate pesticidal activity through bioassays performed in the presence of Lepidopteran or Hemipteran pest larvae using plant leaf disks obtained from the transformed plants.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. As

TABLE 2

Characteristics of TIC4747 and related family members.

| Protein | Molecular Weight (in Daltons) | Amino Acid Length | Isoelectric Point | Charge at PH 7.0 | No. of Strongly Basic (—) Amino Acids | No. of Strongly Acidic Amino Acids | No. of Hydrophobic Amino Acids | No. of Polar Amino Acids |
|---|---|---|---|---|---|---|---|---|
| TIC4747 | 137364.49 | 1217 | 6.2587 | −5.0 | 145 | 134 | 601 | 616 |
| TIC7181 | 137378.52 | 1217 | 6.2587 | −5.0 | 145 | 134 | 601 | 616 |
| TIC4904 | 137335.54 | 1217 | 6.1028 | −7.0 | 141 | 134 | 602 | 615 |
| TIC6547 | 136629.45 | 1211 | 6.0733 | −7.0 | 141 | 135 | 597 | 614 |
| TIC4006 | 136704.56 | 1213 | 5.8876 | −9.0 | 135 | 132 | 592 | 621 | understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

Recombinant nucleic acid molecule compositions that encode TIC4747 or related family member insecticidal proteins are contemplated. For example, TIC4747 and related family member insecticidal proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to TIC4747 or related family member insecticidal protein encoding sequences for expression of the protein in plants or a Bt-functional promoter operably linked to a TIC4747 or related family member protein encoding sequence for expression of the protein in a Bt bacterium or other *Bacillus* species. Other elements can be operably linked to TIC4747 or related family member protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NOs:1, 3, 5, 7, 9, 11, 13, 15, 17, and 19 that encodes the polypeptides or proteins having the amino acid sequences set forth in SEQ ID NOs:2, 4, 6, 8, 10, 12, 14, 16, 18, and 20. The codons of a recombinant polynucleotide molecule encoding for proteins disclosed herein can be substituted by synonymous codons (known in the art as a silent substitution).

A recombinant DNA construct comprising TIC4747 or related family member protein encoding sequences can further comprise a region of DNA that encodes for one or more insect inhibitory agents which can be configured to concomitantly express or co-express with a DNA sequence encoding a TIC4747 or related family member protein, a protein different from TIC4747 or related family member proteins, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of a toxic agent.

A recombinant DNA construct can be assembled so that all proteins or dsRNA molecules are expressed from one promoter or each protein or dsRNA molecules is under separate promoter control or some combination thereof. The proteins of this invention can be expressed from a multi-gene expression system in which one or more proteins of the TIC4747 protein toxin class are expressed from a common nucleotide segment which also contains other open reading frames and promoters, depending on the type of expression system selected. In one example, a plant multi-gene expression system can utilize multiply-linked expression cassettes, each cassette expressing a different protein or other agent such as one or more dsRNA molecules. Yet in another example, a plant multi-gene expression system can utilize multiply-unlinked expression cassettes each expressing a different protein or other agent such as one or more dsRNA molecules.

Recombinant polynucleotides or recombinant DNA constructs comprising TIC4747 or a related family member protein encoding sequence can be delivered to host cells by vectors, e.g., a plasmid, baculovirus, synthetic chromosome, virion, cosmid, phagemid, phage, or viral vector. Such vectors can be used to achieve stable or transient expression of TIC4747 or a related family member protein encoding sequence in a host cell, or subsequent expression of the encoded polypeptide. An exogenous recombinant polynucleotide or recombinant DNA construct that comprises TIC4747 or a related family member protein encoding sequence and that is introduced into a host cell is referred herein as a "transgene."

Transgenic bacteria, transgenic plant cells, transgenic plants, and transgenic plant parts that contain a recombinant polynucleotide that expresses any one or more of TIC4747 or a related family member protein encoding sequence are provided herein. The term "bacterial cell" or "bacterium" can include, but is not limited to, an *Agrobacterium, Rhizobium, Bacillus, Brevibacillus, Escherichia, Pseudomonas, Klebsiella*, and *Erwinia* wherein the *Bacillus* species can be a *Bacillus cereus* or a *Bacillus thuringiensis*, the *Brevibacillus* can be a *Brevibacillus laterosperous*, and the *Escherichia* can be an *Escherichia coli* cell. The term "plant cell" or "plant" can include but is not limited to a monocot, a dicot, an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect or Hemiptera or Lepidoptera-inhibitory amounts of TIC4747 or a related family member are provided. Such plants can be made by introducing a recombinant polynucleotide that encodes any of the TIC4747 or related family member proteins provided herein into a plant cell, and selecting a plant derived from the plant cell that expresses a Lepidoptera-inhibitory or Hemiptera-inhibitory amount of the protein. Plants can be derived from the plant cells by regeneration, seed, pollen, or meristem transformation techniques. Methods for transforming plants are known in the art.

Processed plant products, wherein the processed product comprises a detectable amount of a protein from the TIC4747 protein toxin class, an insect inhibitory fragment thereof, or any distinguishing portion thereof, are also disclosed herein. In certain embodiments, the processed product is selected from the group consisting of plant parts, plant biomass, oil, meal, sugar, animal feed, flour, flakes, bran, lint, hulls, processed seed and seed. In certain embodiments, the processed plant product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a protein from the TIC474 protein toxin class.

Plants expressing a protein from the TIC4747 protein toxin class can be crossed by breeding transgenic events expressing other toxin proteins or expressing other transgenic traits such as herbicide tolerance genes, genes conferring yield or stress tolerance traits, and the like, or such traits can be combined in a single vector so that the traits are all linked.

As described further in the Examples of this application, synthetic or artificial sequences encoding TIC4747 and related family member insecticidal proteins were designed for use in plants. Exemplary synthetic nucleotide sequences that were designed for use in plants are set forth in SEQ ID NO:11 (TIC4747PL), SEQ ID NO:13 (TIC7181PL), SEQ ID NO:15 (TIC4904PL), SEQ ID NO:17 (TIC6547PL), and SEQ ID NO:19 (TIC4006PL).

For expression in plant cells, the TIC4747 and related family member insecticidal proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the TIC4747 and related family member insecticidal proteins to the chloroplast, a sequence encoding a chloroplast transit peptide is placed 5' in operable linkage and in frame to a synthetic coding sequence encoding the TIC4747PL and related family member insecticidal protein that has been designed for optimal expression in plant cells.

Expression cassettes and vectors containing these synthetic or artificial nucleotide sequences can be constructed and introduced into corn, cotton, and soybean plant cells in accordance with transformation methods and techniques which are known in the art. Transformed cells are regenerated into transformed plants that are observed to be expressing the TIC4747PL and related family member insecticidal protein. To test pesticidal activity, bioassays are performed in the presence of Hemipteran pest nymphs using, for example developing soybean pods obtained from the transformed soybean plants or leaf discs from transformed corn plants.

TIC4747 and related family member protein-encoding sequences and sequences having a substantial percentage identity to TIC4747 and related family member protein-encoding sequences can be identified using methods known to those of ordinary skill in the art such as polymerase chain reaction (PCR), thermal amplification and hybridization. For example, the proteins of the TIC4747 and related family member protein toxin class can be used to produce antibodies that bind specifically to this class of proteins, and can be used to screen for and to find other members of the class.

Further, nucleotide sequences encoding the TIC4747 protein toxin class (and reverse complement sequences) can be used as probes and primers for screening to identify other members of the class using thermal-cycle or isothermal amplification and hybridization methods. Nucleotide sequence homologs, e.g., insecticidal proteins encoded by nucleotide sequences that hybridize to each or any of the sequences disclosed in this application under stringent hybridization conditions, are an embodiment of the present invention. The invention also provides a method for detecting a first nucleotide sequence that hybridizes to a second nucleotide sequence, wherein the first nucleotide sequence (or its reverse complement sequence) encodes an insecticidal protein or insecticidal fragment thereof and hybridizes under stringent hybridization conditions to the second nucleotide sequence. In such case, the second nucleotide sequence can be any of the nucleotide sequences disclosed in the TIC4747 protein toxin class under stringent hybridization conditions. Nucleotide coding sequences hybridize to one another under appropriate hybridization conditions, such as stringent hybridization conditions, and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding such related proteins, and those sequences, to the extent that they function to express insecticidal proteins either in Bt strains or in plant cells, are embodiments of the present invention, recognizing of course that many such redundant coding sequences will not hybridize under these conditions to the native Bt sequences encoding TIC4747 and related family members. This application contemplates the use of these, and other identification methods known to those of ordinary skill in the art, to identify TIC4747 and related family member protein-encoding sequences and sequences having a substantial percentage identity to TIC4747 and related family member protein-encoding sequences.

This disclosure also contemplates the use of molecular methods known in the art to engineer and clone commercially useful proteins comprising chimeras of proteins from pesticidal proteins; e.g., the chimeras may be assembled from segments of TIC4747 and related family member proteins to derive additional useful embodiments including assembly of segments of TIC4747 and related family member proteins with segments of diverse proteins different from TIC4747 and related proteins. Proteins of the TIC4747 protein toxin class may be subjected to alignment to each other and to other Bt pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity and/or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

Methods of controlling insects, in particular Hemipteran and Lepidopteran infestations of crop plants, with proteins from the TIC4747 toxin protein class are also disclosed in this application. Such methods can comprise growing a plant comprising an insect- or Hemiptera- or Lepidoptera-inhibitory amount of a protein from the TIC4747 toxin protein class. In certain embodiments, such methods can further comprise any one or more of: (i) applying any composition comprising or encoding a protein of the TIC4747 protein toxin class to the plant or a seed that gives rise to the plant; and (ii) transforming the plant or a plant cell that gives rise to the plant with a polynucleotide encoding a protein of the TIC4747 protein toxin class. In general, it is contemplated that any protein in the TIC4747 protein toxin class can be provided in a composition, provided in a microorganism, or provided in a transgenic plant to confer insect inhibitory activity against Lepidopteran insects.

In certain embodiments, a recombinant polypeptide of the TIC4747 protein toxin class is the insecticidally active ingredient of an insect inhibitory composition prepared by culturing recombinant Bt cells under conditions to express and produce proteins of the TIC4747 protein toxin class. Such a composition can be prepared by desiccation, lyophilization, homogenization, extraction, filtration, centrifugation, sedimentation, or concentration of a culture of recombinant Bt cells expressing/producing said recombinant polypeptide. Such a process can result in a Bt or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the target pest species to provide a refuge for such unprotected plants. One particular example is described in U.S. Pat. No. 6,551,962, which is incorporated by reference in its entirety.

In one embodiment, to reduce the likelihood of resistance development, an insect inhibitory composition or transgenic plant comprising one or more proteins from the TIC4747 protein toxin class can further comprise at least one additional polypeptide that exhibits insect inhibitory activity against the same or other susceptible target insect species, but is different from the TIC4747 protein toxin. Possible additional polypeptides for such a composition include an insect inhibitory protein, an insect inhibitory dsRNA molecule, and an ancillary protein. One example for the use of such ribonucleotide sequences to control insect pests is described in U.S. Patent Publication 2006/0021087. Such additional polypeptide for the control of Lepidopterans may be selected from the group consisting of a Lepidopteran insect inhibitory protein, such as, but not limited to, Cry1A (U.S. Pat. No. 5,880,275), Cry1Ab, Cry1Ac, Cry1A.105, Cry1Ae, Cry1B (U.S. patent Publication Ser. No. 10/525,318), Cry1C (U.S. Pat. No. 6,033,874), Cry1D, Cry1Da, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, TIC2160 (International Application Publication WO2016/061392(A2)), Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, axmi209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), DIG-657 (International Application Publication WO2015/195594(A2)), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO: 2 and derivatives thereof as described in U.S. Patent Publication 2012-0167259 A1, SEQ ID NO: 2 and derivatives thereof as described in U.S. Patent Publication 2012-0047606 A1, SEQ ID NO: 2 and derivatives thereof as described in U.S. Patent Publication 2011-0154536 A1, SEQ ID NO: 2 and derivatives thereof as described in U.S. Patent Publication 2011-0112013 A1, SEQ ID NO: 2 and 4 and derivatives thereof as described in U.S. Patent Publication 2010-0192256 A1, SEQ ID NO: 2 and derivatives thereof as described in U.S. Patent Publication 2010-0077507 A1, SEQ ID NO: 2 and derivatives thereof as described in U.S. Patent Publication 2010-0077508 A1, SEQ ID NO: 2 and derivatives thereof as described in U.S. Patent Publication 2009-0313721 A1, SEQ ID NO: 2 or 4 and derivatives thereof as described in U.S. Patent Publication 2010-0269221 A1, SEQ ID NO: 2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO: 2 and derivatives thereof as described in U.S. Pat. No. 7,510,878(B2), SEQ ID NO: 2 and derivatives thereof as described in U.S. Pat. No. 7,812,129(B1); DIG-911 and DIG-180 as described in US Patent Publication No. 2015-0264940A1, and the like.

Where the target insect pest is a Hemipteran insect pest, such additional polypeptide may be selected from the group consisting of Hemipteran-active proteins such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1).

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Coleopteran pests, combinations of insect inhibitory proteins of the present invention can be used with Coleopteran-active proteins such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), PHI-4 variants (U.S. Patent Application Publication 2016-0281105 A1), PIP-72 variants (WO 2016-144688 A1), PIP-45 variants, PIP-64 variants, PIP-74 variants, PIP-75 variants, and PIP-77 variants (WO 2016-144686 A1), DIG-305 (WO 2016109214 A1), PIP-47 variants (U.S. Patent Publication 2016-0186204 A1), DIG-17, DIG-90, DIG-79 (WO 2016-057123 A1), DIG-303 (WO 2016-070079 A1), and $\overline{\omega}$-Hexatoxin-Hv1a (U.S. Patent Application Publication US2014-0366227 A1).

Additional polypeptides for the control of Coleopteran, Lepidopteran, and Hemipteran insect pests can be found on the *Bacillus thuringiensis* toxin nomenclature website maintained by Neil Crickmore (on the World Wide Web at btnomenclature.info).

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are complementary in mode of action with the proteins disclosed, so that the formulation pesticides act through a different mode of action to control the same or similar pests that can be controlled by the proteins disclosed, or that such pesticides act to control pests within a broader host range, such as Lepidopteran or Hemipteran species or other plant pest species such as Coleopteran species that are not effectively controlled.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

EXAMPLES

In view of the foregoing, those of skill in the art should appreciate that changes can be made in the specific aspects which are disclosed and still obtain a like or similar result without departing from the spirit and scope of the invention.

Thus, specific details disclosed herein are not to be interpreted as limiting. It should be understood that the entire disclosure of each reference cited herein is incorporated by reference in its entirety within the disclosure of this application.

Example 1

Discovery of Novel Bt Genes

This Example describes the discovery of the pesticidal proteins TIC4747, TIC7181, TIC4904, TIC6547, and TIC4006.

A sequence encoding a novel Bacillus thuringiensis (Bt) pesticidal protein was identified, cloned, sequence confirmed, and tested in bioassay. The pesticidal protein TIC4747, presented herein as SEQ ID NOs 1 (Bt coding sequence) and 2 (protein), was isolated from Bacillus thuringiensis strain CFB007452. High throughput sequencing and bioinformatics were used to screen Bt genomes for genes (open reading frames) encoding proteins exhibiting similarity to TIC4747. Four related toxin proteins were identified in this screen and are presented in Table 3, along with the corresponding Bt strain and percent identity to TIC4747.

TABLE 3

TIC4747 and related toxin proteins.

| Toxin | Strain | Coding Sequence | Protein Sequence | % Identity to TIC4747 protein |
|---|---|---|---|---|
| TIC4747 | CFB007452 | 1 | 2 | — |
| TIC4904 | CFB007432 | 5 | 6 | 94.2 |
| TIC4006 | WC12466 | 9 | 10 | 82.3 |
| TIC6547 | CFB231019 | 7 | 8 | 93.1 |
| TIC7181 | EG9737 | 3 | 4 | 99.9 |

Nucleotide segments encoding TIC4747 and related family members were made by polymerase chain reaction (PCR) amplification using genomic DNA from the corresponding strains and cloned into Bt plasmid expression vectors which comprised a sporulation stage promoter operably linked to each toxin coding sequence.

Example 2

Bioassay of TIC4747 and Related Family Members Against Insect Pests

TIC4747 and related family members were expressed in Bt and E. coli, and assayed for toxicity to various species of Lepidoptera, Coleoptera, Hemiptera, and Diptera.

Bacillus thuringiensis host cells were transformed with plasmid expression vectors comprising the insect toxin coding sequences presented in Table 3 of Example 1. The transformed Bt cells were grown in liquid culture, harvested during the sporulation growth stage, and protein was extracted from the cell lysate. In addition, Histadine tagged proteins, TIC4747 His (SEQ ID NO:22, encoded by SEQ ID NO:21), TIC4904 His (SEQ ID NO:24, encoded by SEQ ID NO:23), TIC6547_His (SEQ ID NO:26, encoded by SEQ ID NO:25), and TIC4006_His (SEQ ID NO:28, encoded by SEQ ID NO:27) were prepared in E. coli cells using methods known in the art.

Preparations of TIC4747, TIC4006, TIC4904, and TIC6547 were presented in an insect diet bioassay against the Lepidopteran pest species Fall Armyworm (FAW, Spodoptera frugiperda), Corn Earworm (CEW, Helicoverpa zea), European Corn Borer (ECB, Ostrinia nubilalis), Southwestern Corn borer (SWC, Diatraea grandiosella), Soybean Looper (SL, Chrysodeixis includens), Velvetbean Caterpillar (VBC, Anticarsia gemmatalis), Tobacco Budworm (TBW, Heliothis virescens), Black Cutworm (BCW, Agrotis ipsilon), Southern Armyworm (SAW, Spodoptera eridania), and Diamondback Moth (DBM, Plutella xylostella); the Coleopteran pest species Western Corn Rootworm (WCR, Diabrotica virgifera LeConte) and Colorado Potato Beetle (CPB, Leptinotarsa decemlineata); the Hemipteran pest species Tarnished Plant Bug (TPB, Lygus lineolaris), Western Tarnished Plant Bug (WTPB, Lygus hesperus), Southern Green Stink Bug (SGB, Nezara viridula), Neotropical Brown Stink Bug (NBSB, Euschistus heros). Preparations of TIC4747, TIC4006, and TIC4904 were also presented in an insect diet bioassay against the Dipteran pest species Yellow Fever Mosquito (YFM, Aedes aegypti). Preparations of TIC7181 were presented in an insect diet bioassay against the pests, CEW, ECB, FAW, SAW, SBL, SWCB, TBW, VBC, CPB, TPB, and WTB.

The pesticidal toxin TIC4747 demonstrated activity against Tarnished Plant Bug, Western Tarnished Plant Bug, Green Stink Bug, and Neotropical Brown Stink Bug. The pesticidal toxin TIC6547 demonstrated activity against Diamondback Moth. The pesticidal toxin TIC7181 demonstrated activity against Tarnished Plant Bug.

Example 3

Design of Synthetic Coding Sequences Encoding TIC4747PL and Related Family Members for Expression in Plant Cells Synthetic coding sequences are designed for use in expression of the encoded protein in plants, and are cloned into binary plant transformation vectors, and used to transform plant cells. The synthetic sequences are synthesized, according to methods generally described in U.S. Pat. No. 5,500,365 to avoid certain inimical problem sequences such as ATTTA and A/T rich plant polyadenylation sequences, while preserving the amino acid sequence of the original protein. The synthetic coding sequences presented in Table 4 below encode plant version proteins of TIC4747 and related family members wherein an additional alanine amino acid residue is incorporated immediately following the initiating methionine amino acid residue in the native toxin protein sequence to improve plant expression of the toxin.

TABLE 4

Synthetic coding sequences used for expression of TIC4747PL and related family members in plant cells.

| Toxin | Plant Coding Sequence SEQ ID NO: | Plant Protein SEQ ID NO: |
|---|---|---|
| TIC4747PL | 11 | 12 |
| TIC7181PL | 13 | 14 |
| TIC4904PL | 15 | 16 |
| TIC6547PL | 17 | 18 |
| TIC4006PL | 19 | 20 |

The synthetic coding sequences encoding TIC4747PL and related family members are cloned into binary plant transformation vectors comprising a first transgene cassette for expression of the TIC4747PL toxin or related family members and a second transgene cassette for selection of transformed plant cells. This first cassette comprises a plant expressible promoter operably linked 5' to an optional intron, which is operably linked 5' to a plastid targeted or untargeted TIC4747PL toxin or related family member coding sequence, which is operably linked 5' to a 3' UTR.

The second transgene cassette for selection of transformed plant cells uses either glyphosate or an antibiotic such as spectinomycin.

Example 4

Assay of TIC4747PL and Related Family Members Against Hemipteran Pests in Stably Transformed Soybean Plants This Example describes the assay of activity against Hemipteran insect pests in soybean plants stably transformed to express TIC4747PL or related family member toxins.

Soybean plants are transformed using binary plant transformation vectors as described in Example 3. The transformed soybean plant cells are induced to form whole plants. Assay for activity against the Hemipteran pests is performed using a variety of techniques which will depend upon the species of Hemipteran pests and the preferred target tissue of that pest. For example, the Hemipteran pest species of Stink Bugs typically feed on the developing seeds and pods of the soybean plant. To assay for activity against Stink Bugs, R5 stage pods are harvested from the transgenic soybean plants expressing TIC4747PL or related family members and placed in a covered Petri dish or large multi-well plate containing a layer of either agar or wet paper to provide humidity to the feeding environment. Second instar Stink Bug nymphs are placed in the Petri dish or large multi-well plate. A cover providing for the exchange of oxygen while preventing desiccation is placed over the feeding environment. The Stink Bug nymphs are allowed to feed for several days. Measurements of stunting and mortality are taken and compared to Stink Bugs nymphs feeding on pods from untransformed soybean plants.

Alternatively, assay of activity can also be performed on whole stably transformed plants. Transformed plants expressing a protein from the TIC4747 protein toxin class are grown in a growth chamber or in the greenhouse. At R5 stage, the plants are enclosed in a cage made from breathable plastic "pollination" sheets (Vilutis and Company Inc, Frankfort, Ill.). The sheet sleeves are secured to the main stem just above the soil surface using a Velcro® tie. Each plant is infested with a specific number of second instar Stink Bug nymphs. The nymphs are released into each individual cage through a small slit on the cage side and then the cage is securely closed ensuring the insects won't escape; and allowed to feed on the soybean pods for several days to a week or more. Observations are taken each day to determine measurements of stunting and mortality. At the end of the feeding period, the live and dead nymphs are collected. The plants are cut below the cages and moved to a laboratory where the insects are collected for each plant. Before opening the cage, the plants are vigorously shaken to ensure all of the insects fall off from their feeding sites to the base of the cage. Then the cage base is opened and all plant material is removed and placed on a black sheet. The insects can be collected using an aspirator or some other means. The number of insects and their developmental stage is recorded for each plant. The number and developmental stage of dead nymphs is also recorded. These measurements are compared to the measurements obtained from the negative control, un-transformed plants.

Delays in development of the Stink Bug nymphs (stunting) or mortality are interpreted as an indication of toxicity if, when compared to the un-transformed controls, there is a significant difference.

Example 5

Assay of TIC4747PL or Related Family Member Activity Against Hemipteran Pests in Stably Transformed Corn Plants This Example describes the assay of activity against Hemipteran insect pests in corn plants stably transformed to express TIC4747PL or related family member toxins.

Corn plants are transformed using binary plant transformation vectors as described in Example 3 above. The transformed corn plant cells are induced to form whole plants. Assay for activity against the Hemipteran pests is performed using a variety of techniques which will depend upon the species of Hemipteran pest and the preferred target tissue of that pest. For example, the Hemipteran pest species of Stink Bugs typically feed on the young corn plants in late spring or early summer, resulting in holes in the leaf, and if severe, deformed plants. In late summer, Stink Bugs typically feed on the ear itself, directly destroying the kernels.

One method to assay for Stink Bug activity is to expose the Stink Bug nymphs to leaf discs derived from stably transformed corn plants expressing TIC4747PL or related family members in large multi-well plates. Second stage instar Stink Bug nymphs are placed in large multi-well plates with leaf discs derived from the stably transformed corn plants and allowed to feed for several days. Measurements of stunting and mortality are taken and compared to Stink Bug nymphs who have fed on un-transformed corn leaf discs.

Alternatively, whole transformed plants can be used to assay for Stink Bug activity. Stably transformed corn plants expressing TIC4747PL or related family members are enclosed in cages in a similar manner as described for soybean plants in Example 4 above. Second instar nymphs are introduced to V3 stage corn plants and allowed to feed for several days to a week. After the prescribed feeding period, the nymphs are collected as described in Example 4 above. Measurements of stunting and mortality are compared to un-transformed control plants.

To assay Stink Bug activity using stably transformed corn ears, a similar approach can be taken as that of assaying in V3 stage plants. The developing corn ears of stably transformed corn plants expressing TIC4747PL or related family members are encapsulated using sheets of material that permit the free exchange of air while preventing escape of the Stink Bug nymphs. The encapsulated ears are infested with second instar stage Stink Bug nymphs and allowed to feed on the developing kernels of the ear for several days to a week. Measurements of stunting and mortality are compared to un-transformed control plant ears.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide segment encoding a pesticidal protein or fragment thereof, wherein:
   a) said pesticidal protein comprises the amino acid sequence of SEQ ID NO:2, SEQ ID NO:4, SEQ ID NO:12, SEQ ID NO:14, or SEQ ID NO:22; or b) said pesticidal protein comprises an amino acid sequence having at least 99% amino acid sequence identity to the amino acid sequence of SEQ ID NO:2, SEQ ID NO:4, SEQ ID NO:12, SEQ ID NO:14, or SEQ ID NO:22.

2. A vector comprising the recombinant nucleic acid molecule of claim 1, wherein said vector is selected from the group consisting of a plasmid, phagemid, bacmid, cosmid, and a bacterial or yeast artificial chromosome.

3. A host cell comprising the recombinant nucleic acid molecule of claim 1, wherein said host cell is selected from the group consisting of a bacterial and a plant cell.

4. The host cell of claim 3, wherein the bacterial host cell is from a genus of bacteria selected from the group consisting of: *Agrobacterium, Rhizobium, Bacillus, Brevibacillus, Escherichia, Pseudomonas, Klebsiella*, and *Erwinia*; and wherein said *Bacillus* species is a *Bacillus cereus* or a *Bacillus thuringiensis*, said *Brevibacillus* is a *Brevibacillus laterosperous*, and said *Escherichia* is an *Escherichia coli*.

5. The host cell of claim 3, wherein said plant cell is a dicotyledonous or a monocotyledonous plant cell.

6. The host cell of claim 5, wherein said plant host cell is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

7. The recombinant nucleic acid molecule of claim 1, wherein said protein exhibits activity against an insect species of the order of Hemiptera.

8. The recombinant nucleic acid molecule of claim 7, wherein said insect species is selected from the group consisting of: *Chinavia hilaris, Chinavia marginata, Chinavia pensylvanica, Chlorochroa granulose, Chlorochroa kanei, Chlorochroa ligata, Chlorochroa lineate, Chlorochroa opuntiae, Chlorochroa persimilis, Chlorochroa rossiana, Chlorochroa sayi, Chlorochroa uhleri, Chlorochroa belfragii, Chlorochroa faceta, Chlorochroa osborni, Chlorochroa saucia, Chlorochroa senilis, Nezara viridula, Edessa meditabunda, Edessa bifida, Edessa florida, Euschistus heros, Euschistus acuminatus, Euschistus biformis, Euschistus conspersus, Euschistus crenator, Euschistus egglestoni, Euschistus ictericus, Euschistus inflatus, Euschistus latimarginatus, Euschistus obscures, Euschistus politus, Euschistus quadrator, Euschistus sevus, Euschistus strenuous, Euschistus tristigmus, Euschistus variolarius Halyomorpha halys, Thyanta accerra, Thyanta calceata, Thyanta custator, Thyanta pallidovirens, Thyanta perditor, Thyanta maculate, Thyanta pseudocasta Dichelops melacanthus, Dichelops avilapiresi, Dichelops bicolor, Dichelops dimidatus, Dichelops furcatus, Dichelops furcifrons, Dichelops lobatus, Dichelops miriamae, Dichelops nigrum, Dichelops peruanus, Dichelops phoenix, Dichelops saltensis, Piezodorus guildinni, Piezodorus lituratus Megacopta cribraria, Lygus hesperus*, and *Lygus lineolaris*.

9. A plant comprising a recombinant nucleic acid molecule comprising a heterologous promoter operably linked to a polynucleotide segment encoding a pesticidal protein or fragment thereof, wherein:

a) said pesticidal protein comprises the amino acid sequence of SEQ ID NO:2, SEQ ID NO:4, SEQ ID NO:12, SEQ ID NO:14, or SEQ ID NO:22; or b) said pesticidal protein comprises an amino acid sequence having at least 99% amino acid sequence identity to the amino acid sequence of SEQ ID NO:2, SEQ ID NO:4, SEQ ID NO:12, SEQ ID NO:14, or SEQ ID NO:22;

wherein said plant exhibits a detectable amount of said pesticidal protein, wherein the pesticidal protein comprises an amino acid sequence of SEQ ID NO: 2, SEQ ID NO:4, SEQ ID NO:12, SEQ ID NO:14, or SEQ ID NO:22.

10. The plant of claim 9, wherein said plant is a monocot plant or a dicot plant.

11. The plant of claim 10, wherein the plant is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

12. A seed from the plant of claim 9, wherein said seed comprises said recombinant nucleic acid molecule.

13. An insect inhibitory composition comprising the recombinant nucleic acid molecule of claim 1.

14. The insect inhibitory composition of claim 13, further comprising a nucleotide sequence encoding at least one other pesticidal agent that is different from said pesticidal protein.

15. The insect inhibitory composition of claim 14, wherein said at least one other pesticidal agent is selected from the group consisting of an insect inhibitory protein, an insect inhibitory dsRNA molecule, and an ancillary protein.

16. The insect inhibitory composition of claim 15, wherein said at least one other pesticidal agent exhibits activity against one or more pest species of the orders Lepidoptera, Coleoptera, Hemiptera, Homoptera, or Thysanoptera.

17. The insect inhibitory composition of claim 16, wherein said at least one other pesticidal protein is selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC3131, TIC2160, VIP3A, VIP3B, VIP3Ab, AXMI-001, AXMI-002, AXMI-030, AXMI-035, AXMI-036, AXMI-045, Axmi52, Axmi58, Axmi88, Axmi97, Axmi102, Axmi112, Axmi117, Axmi100, AXMI-115, AXMI-113, AXMI-005, AXMI134, AXMI-150, Axmi171, AXMI-184, axmi196, axmi204, axmi207, axmi209, Axmi205, AXMI218, AXMI220, AXMI221z, AXMI222z, AXMI223z, AXMI224z, AXMI225z, AXMI238, AXMI270, AXMI279, AXMI335, AXMI345, AXMI-R1 and variants thereof, IP3 and variants thereof, DIG-3, DIG-5, DIG-10, DIG-11, DIG-657 protein, PHI-4 variants, PIP-72 variants, PIP-45 variants, PIP-64 variants, PIP-74 variants, PIP-77 variants, DIG-305, PIP-47 variants, DIG-17, DIG-90, DIG-79, and DIG-303.

18. A commodity product produced from the host cell of claim 3, said commodity product comprising a detectable amount of said recombinant nucleic acid molecule or pesticidal protein.

19. The commodity product of claim 18, selected from the group consisting of commodity corn bagged by a grain handler, corn flakes, corn cakes, corn flour, corn meal, corn syrup, corn oil, corn silage, corn starch, corn cereal, edible soybean, rice, wheat, sorghum, pigeon pea, peanut, fruit, melon, and vegetable commodity products containing a detectable amount of the recombinant nucleic acid molecule of claim 3, whole or processed cotton seed, cotton oil, lint, seeds and plant parts processed for feed or food, fiber, paper, biomasses, and fuel products derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

20. A method of producing seed comprising the recombinant nucleic acid molecule of claim 1, said method comprising:
   a) planting at least one seed comprising said recombinant nucleic acid molecule;
   b) growing plants from said seed; and
   c) harvesting seed from said plants, wherein said harvested seed comprises said recombinant nucleic acid molecule.

21. A plant resistant to insect infestation, wherein said plant comprises the recombinant nucleic acid molecule of claim 1.

22. A method for controlling a Lepidopteran species pest, and controlling a Hemipteran species infestation of a plant, said method comprising contacting the pest with a transgenic plant cell expressing an insecticidally effective amount of a pesticidal protein comprising an amino acid sequence having at least 99% amino acid sequence identity to SEQ ID NO:2, SEQ ID NO:4, SEQ ID NO:12, SEQ ID NO:14, or SEQ ID NO:22.

* * * * *

SEQUENCE LISTING

<160> NUMBER OF SEQ ID NOS: 28

<210> SEQ ID NO 1
<211> LENGTH: 3654
<212> TYPE: DNA
<213> ORGANISM: Bacillus thuringiensis
<220> FEATURE:
<221> NAME/KEY: misc_feature
<222> LOCATION: (1)..(3654)
<223> OTHER INFORMATION: The native nucleotide sequence encoding TIC4747
toxin protein obtained from Bacillus thuringiensis species
CFB007452.

<400> SEQUENCE: 1

```
atggatcaaa agattataaa aatgcgagaa gcagtcaatg ccttgttttc caataatcat      60
ttaaaattga atattactga ttacaatata gatcagactg cataccttgt tgatagtatg     120
tctgatgacg catatcgaca agaaaaaatg atgtttctcg atcaaatcaa atttgcaaag     180
cgcttgagcc aaaaacgcaa cctgttgaat catggagatt ttgaaggatc caattggaca     240
ggtaagaatg gatggaaaag aataaattat gtagttgtcg catcggatca tcctatattt     300
aaaggccgat atttacacat accaggtgca acaaccgcga tgagtggcgc aatcattccg     360
acttatgtat atcaaagtat agatgaatcg aagttaaaac cgtatacacg ttatttggta     420 cgaggggtttg ttggaaagag tcaagattta gcgttacttg tttcccggta taccaaagaa     480
gtgtacaaga aaatcaatgt accaaatgat aaagactacg atatgacatc gcatataaat     540
agggaagaga atctatggca aatagatat ataaaagaca cttcggttca aaattcaatc     600
tctatgtgca aaaatccaca tgaatttacg tgtcatattg atataggga actggataga     660 aagaaaggtc ctggtataac catcggtttt caaattggaa caacagatgg gatggcaaca     720
ttagataata tagaagtgat agaagcacat ccgttaaccg gatacgcctt agcacgtatc     780
gaaaaacgtg aacgtaaatg gaaacaaaaa tggctagagc atcgaataca aatcgaaaag     840
gctgtgcaaa cagcgcaaga ggtgattcga aatttattta catgcccaca acaaaatcaa     900
ttgaactgga tgacaacccg aaacgacatt gcacatgcag aaacattgat aaaagagatt     960
tcatatcggt atagccaact ttcttgtgga gatttcccca tactaccaga agaggcgtat    1020
gacatccttc aacaactttc aactgcagtt gaaaccgcaa aagcgttgta tacacaacga    1080
aacgtggtga ataatgggga ttttcaagct ggattatcga attggcatag acagatggt    1140 gcagagatac aacaaattca gaatgcatcc tctgttctaa taattacaga ctgggctgcg    1200
aatatttcac aagacatgcg tgtagttgaa aaaggtagct atctgttgcg cgtaacagcg    1260
aaaaaagaag atgccggaga aggttatatt acaattagtg attgtgccgc attgatagaa    1320
acattgacat ttacaacggg ggaatctgtg gaaagtctga cacattctga tattcattca    1380
aggctccata acgctataa taaaaaacac ataaaaaacc atccttcaga agaatatgaa    1440
atagaatcgg atcttcattt atttaatagg gcggaacaaa acggttctct ccctctagc    1500 tatgtaacca aaacgatgga aatctttccg gaaaccaatc gagtacgcat tgaaattga    1560 gaaacaggtg aacatttat agtggaaagt gtggaattaa ttcgaatgga acagatgaac    1620
gaaacaaaca atccagatgt agatgttcaa attgtaatga atgatacacc cgctacacaa    1680
tttgatccag tttcttttac agaatccacg gtgaggccca gaaatgctca gtatgcatat    1740
tctcatgatt caaatatagg ttatgaaaat cctaactgga tggctgatat ttcaggtgat    1800
```

-continued

```
actttatttta ctgatttatc tatccctggt acacataata caatggctct ttatggagga    1860
gatattacac aatgtcaaac gatgtcactg aatacgcaat tacatgtagg aattcgttat    1920
ttagatattc gctgtaggca catagaaaat gcttttgcga ttcatcatgg acctgtgtac    1980
caaaatgcga tgtttggaga tgtttgtatt gccgtaagga attttttgag aagcaaccct    2040
agtgaaacag tatttatgcg gataaaagaa gaacatacag cagaaaacaa tacaagatct    2100
ttttcagata catttgcaga ttataagtct caatatagcg acttattttg ggattggaca    2160
ggtgataacc caagattaag tgaaataaga ggaaaagttg ttgttttaca aaattttttca   2220
ggtggtaaat ttggtatcaa ttacaataca ttgaatactc aagatcaata tcatttaaat    2280
acaaactggg atttatatga taaatggcta ttcgtcaaag aacatttgta tgccgctgac    2340
aactcttata aaagtggccg taaacaagta tatctgaatt acctaagtgg atcaggtggt    2400
tcatttcctt attttgttgc aagtggacat agtagtccag gtacagatgc tccacaatta    2460
tctacaggtc taacaacacc agcatttgca agctggtatc cggattttcc acggggaagt    2520
tgttttatag gaatttgcac aatttacttt gaaggaacaa atattcttac aagtcagtgg    2580
atagagaaaa atgattttaa atatatagga atcatagctg ctgattttcc aggaagaaca    2640
ttaatttcca atattattag tctgaataaa cttcttagct tagaaattaa aaatggtggt    2700
acctatcaaa ttgtttccgc tttaaataat agtagtgtta tagatatgag tctgagtgga    2760
gatcgaaatg ttcacctatg gtccaataac ggtactctta atcaagtatg gaaattcgtg    2820
tatgattcaa atagattggc ataccaaatt aaaagtctat ccgatgaaaa tttagtacta    2880
acttgggctt attatagtag taatcgagat aatgtaattg ttgcttctaa tcaaaatagc    2940
gatgagcaat attggatacc tgagcgcaca ggcgcatatc attattttaa aaatctcatc    3000
aatccctcgg gagcattaga tgtaagcgga tcaggaacaa caaacggaac gaatattttg    3060
tattggagtt ataacagagc aacgaatcaa aaattcaaac tggaagaagt aaatatacct    3120
ggaggtcaag ctgaaggtgt acttttatat gcagatgcta attatgtagg gaaatctgta    3180
ctactaacaa atagtgtctc aaaccttaga gacgttggta tgaatgatat agccagttct    3240
ataaaattta ttggtcctta tcaagctact ctatatgaac atgataattt tacaggtgcg    3300
gcttttactc tcacatctaa tgttgcaaat ttaaaagatg ttggcatgaa tgatacagtt    3360
agttctataa aaattacaaa gacatctgga ggccgagctc aggtatatat tttatatgca    3420
gatgctaatt atgtaggcag atctgtatgg ttaacatcta atgttgcaaa tttaaaagat    3480
attggcatga atgatacagt cagttctgta gaaattgttg gcgcatatca agccacttta    3540
tatggggatg ccaattatac agggaaggct tataatctca ctcataatgt tacaaattta    3600
aaagatgttg gcatgaatga tatagtcagt tccataaaaa ttttagtgt gtaa           3654
```

<210> SEQ ID NO 2
<211> LENGTH: 1217
<212> TYPE: PRT
<213> ORGANISM: Bacillus thuringiensis
<220> FEATURE:
<221> NAME/KEY: MISC_FEATURE
<222> LOCATION: (1)..(1217)
<223> OTHER INFORMATION: The amino acid sequence of TIC4747.

<400> SEQUENCE: 2

```
Met Asp Gln Lys Ile Ile Lys Met Arg Glu Ala Val Asn Ala Leu Phe
1               5                   10                  15

Ser Asn Asn His Leu Lys Leu Asn Ile Thr Asp Tyr Asn Ile Asp Gln
```

```
                20                  25                  30
Thr Ala Tyr Leu Val Asp Ser Met Ser Asp Ala Tyr Arg Gln Glu
            35                  40                  45
Lys Met Met Phe Leu Asp Gln Ile Lys Phe Ala Lys Arg Leu Ser Gln
    50                  55                  60
Lys Arg Asn Leu Leu Asn His Gly Asp Phe Glu Gly Ser Asn Trp Thr
65                  70                  75                  80
Gly Lys Asn Gly Trp Lys Arg Asn Asn Tyr Val Val Ala Ser Asp
                85                  90                  95
His Pro Ile Phe Lys Gly Arg Tyr Leu His Ile Pro Gly Ala Thr Thr
            100                 105                 110
Ala Met Ser Gly Ala Ile Ile Pro Thr Tyr Val Tyr Gln Ser Ile Asp
        115                 120                 125
Glu Ser Lys Leu Lys Pro Tyr Thr Arg Tyr Leu Val Arg Gly Phe Val
        130                 135                 140
Gly Lys Ser Gln Asp Leu Ala Leu Leu Val Ser Arg Tyr Thr Lys Glu
145                 150                 155                 160
Val Tyr Lys Lys Ile Asn Val Pro Asn Asp Lys Asp Tyr Asp Met Thr
            165                 170                 175
Ser His Ile Asn Arg Glu Glu Asn Leu Trp His Asn Arg Tyr Ile Lys
            180                 185                 190
Asp Thr Ser Val Gln Asn Ser Ile Ser Met Cys Lys Asn Pro His Glu
        195                 200                 205
Phe Thr Cys His Ile Asp Ile Gly Glu Leu Asp Arg Lys Lys Gly Pro
        210                 215                 220
Gly Ile Thr Ile Gly Phe Gln Ile Gly Thr Thr Asp Gly Met Ala Thr
225                 230                 235                 240
Leu Asp Asn Ile Glu Val Ile Glu Ala His Pro Leu Thr Gly Tyr Ala
            245                 250                 255
Leu Ala Arg Ile Glu Lys Arg Glu Arg Lys Trp Lys Gln Lys Trp Leu
        260                 265                 270
Glu His Arg Ile Gln Ile Glu Lys Ala Val Gln Thr Ala Gln Glu Val
        275                 280                 285
Ile Arg Asn Leu Phe Thr Cys Pro Gln Gln Asn Gln Leu Asn Trp Met
        290                 295                 300
Thr Thr Arg Asn Asp Ile Ala His Ala Glu Thr Leu Ile Lys Glu Ile
305                 310                 315                 320
Ser Tyr Arg Tyr Ser Gln Leu Ser Cys Gly Asp Phe Pro Ile Leu Pro
            325                 330                 335
Glu Glu Ala Tyr Asp Ile Leu Gln Gln Leu Ser Thr Ala Val Glu Thr
            340                 345                 350
Ala Lys Ala Leu Tyr Thr Gln Arg Asn Val Val Asn Asn Gly Asp Phe
        355                 360                 365
Gln Ala Gly Leu Ser Asn Trp His Arg Thr Asp Gly Ala Glu Ile Gln
        370                 375                 380
Gln Ile Gln Asn Ala Ser Ser Val Leu Ile Ile Thr Asp Trp Ala Ala
385                 390                 395                 400
Asn Ile Ser Gln Asp Met Arg Val Val Glu Lys Gly Ser Tyr Leu Leu
            405                 410                 415
Arg Val Thr Ala Lys Lys Glu Asp Ala Gly Glu Gly Tyr Ile Thr Ile
            420                 425                 430
Ser Asp Cys Ala Ala Leu Ile Glu Thr Leu Thr Phe Thr Thr Gly Glu
        435                 440                 445
```

```
Ser Val Glu Ser Leu Thr His Ser Asp Ile His Ser Arg Leu His Lys
450                 455                 460

Arg Tyr Asn Lys Lys His Ile Lys Asn His Pro Ser Glu Glu Tyr Glu
465                 470                 475                 480

Ile Glu Ser Asp Leu His Leu Phe Asn Arg Ala Glu Gln Asn Gly Ser
            485                 490                 495

Leu Pro Ser Ser Tyr Val Thr Lys Thr Met Glu Ile Phe Pro Glu Thr
        500                 505                 510

Asn Arg Val Arg Ile Glu Ile Gly Glu Thr Gly Thr Phe Ile Val
    515                 520                 525

Glu Ser Val Glu Leu Ile Arg Met Glu Gln Met Asn Glu Thr Asn Asn
530                 535                 540

Pro Asp Val Asp Val Gln Ile Val Met Asn Asp Thr Pro Ala Thr Gln
545                 550                 555                 560

Phe Asp Pro Val Ser Phe Thr Glu Ser Thr Val Arg Pro Arg Asn Ala
            565                 570                 575

Gln Tyr Ala Tyr Ser His Asp Ser Asn Ile Gly Tyr Glu Asn Pro Asn
            580                 585                 590

Trp Met Ala Asp Ile Ser Gly Asp Thr Leu Phe Thr Asp Leu Ser Ile
            595                 600                 605

Pro Gly Thr His Asn Thr Met Ala Leu Tyr Gly Gly Asp Ile Thr Gln
    610                 615                 620

Cys Gln Thr Met Ser Leu Asn Thr Gln Leu His Val Gly Ile Arg Tyr
625                 630                 635                 640

Leu Asp Ile Arg Cys Arg His Ile Glu Asn Ala Phe Ala Ile His His
                645                 650                 655

Gly Pro Val Tyr Gln Asn Ala Met Phe Gly Asp Val Cys Ile Ala Val
            660                 665                 670

Arg Asn Phe Leu Arg Ser Asn Pro Ser Glu Thr Val Phe Met Arg Ile
        675                 680                 685

Lys Glu Glu His Thr Ala Glu Asn Asn Thr Arg Ser Phe Ser Asp Thr
690                 695                 700

Phe Ala Asp Tyr Lys Ser Gln Tyr Ser Asp Leu Phe Trp Asp Trp Thr
705                 710                 715                 720

Gly Asp Asn Pro Arg Leu Ser Glu Ile Arg Gly Lys Val Val Leu
            725                 730                 735

Gln Asn Phe Ser Gly Gly Lys Phe Gly Ile Asn Tyr Asn Thr Leu Asn
            740                 745                 750

Thr Gln Asp Gln Tyr His Leu Asn Thr Asn Trp Asp Leu Tyr Asp Lys
    755                 760                 765

Trp Leu Phe Val Lys Glu His Leu Tyr Ala Ala Asp Asn Ser Tyr Lys
    770                 775                 780

Ser Gly Arg Lys Gln Val Tyr Leu Asn Tyr Leu Ser Gly Ser Gly Gly
785                 790                 795                 800

Ser Phe Pro Tyr Phe Val Ala Ser Gly His Ser Ser Pro Gly Thr Asp
                805                 810                 815

Ala Pro Gln Leu Ser Thr Gly Leu Thr Thr Pro Ala Phe Ala Ser Trp
            820                 825                 830

Tyr Pro Asp Phe Pro Arg Gly Ser Cys Phe Ile Gly Ile Cys Thr Ile
            835                 840                 845

Tyr Phe Glu Gly Thr Asn Ile Leu Thr Ser Gln Trp Ile Glu Lys Asn
    850                 855                 860
```

Asp Phe Lys Tyr Ile Gly Ile Ile Ala Ala Asp Phe Pro Gly Arg Thr
865                 870                 875                 880

Leu Ile Ser Asn Ile Ile Ser Leu Asn Lys Leu Leu Ser Leu Glu Ile
            885                 890                 895

Lys Asn Gly Gly Thr Tyr Gln Ile Val Ser Ala Leu Asn Asn Ser Ser
        900                 905                 910

Val Ile Asp Met Ser Leu Ser Gly Asp Arg Asn Val His Leu Trp Ser
    915                 920                 925

Asn Asn Gly Thr Leu Asn Gln Val Trp Lys Phe Val Tyr Asp Ser Asn
    930                 935                 940

Arg Leu Ala Tyr Gln Ile Lys Ser Leu Ser Asp Glu Asn Leu Val Leu
945                 950                 955                 960

Thr Trp Ala Tyr Tyr Ser Ser Asn Arg Asp Asn Val Ile Val Ala Ser
            965                 970                 975

Asn Gln Asn Ser Asp Glu Gln Tyr Trp Ile Pro Glu Arg Thr Gly Ala
        980                 985                 990

Tyr His Tyr Phe Lys Asn Leu Ile Asn Pro Ser Gly Ala Leu Asp Val
        995                 1000                1005

Ser Gly Ser Gly Thr Thr Asn Gly Thr Asn Ile Leu Tyr Trp Ser
    1010                1015                1020

Tyr Asn Arg Ala Thr Asn Gln Lys Phe Lys Leu Glu Glu Val Asn
    1025                1030                1035

Ile Pro Gly Gly Gln Ala Glu Gly Val Leu Leu Tyr Ala Asp Ala
    1040                1045                1050

Asn Tyr Val Gly Lys Ser Val Leu Leu Thr Asn Ser Val Ser Asn
    1055                1060                1065

Leu Arg Asp Val Gly Met Asn Asp Ile Ala Ser Ser Ile Lys Phe
    1070                1075                1080

Ile Gly Pro Tyr Gln Ala Thr Leu Tyr Glu His Asp Asn Phe Thr
    1085                1090                1095

Gly Ala Ala Phe Thr Leu Thr Ser Asn Val Ala Asn Leu Lys Asp
    1100                1105                1110

Val Gly Met Asn Asp Thr Val Ser Ser Ile Lys Ile Thr Lys Thr
    1115                1120                1125

Ser Gly Gly Arg Ala Thr Gly Ile Tyr Leu Tyr Ala Asp Ala Asn
    1130                1135                1140

Tyr Val Gly Arg Ser Val Trp Leu Thr Ser Asn Val Ala Asn Leu
    1145                1150                1155

Lys Asp Ile Gly Met Asn Asp Thr Val Ser Ser Val Glu Ile Val
    1160                1165                1170

Gly Ala Tyr Gln Ala Thr Leu Tyr Gly Asp Ala Asn Tyr Thr Gly
    1175                1180                1185

Lys Ala Tyr Asn Leu Thr His Asn Val Thr Asn Leu Lys Asp Val
    1190                1195                1200

Gly Met Asn Asp Ile Val Ser Ser Ile Lys Ile Phe Ser Val
    1205                1210                1215

<210> SEQ ID NO 3
<211> LENGTH: 3654
<212> TYPE: DNA
<213> ORGANISM: Bacillus thuringiensis
<220> FEATURE:
<221> NAME/KEY: misc_feature
<222> LOCATION: (1)..(3654)
<223> OTHER INFORMATION: The native nucleotide sequence encoding TIC7181
      toxin protein obtained from Bacillus thuringiensis species EG9737.

<400> SEQUENCE: 3

```
atggatcaaa agattataaa aatgcgagaa gcagtcaatg ccttgttttc caataatcat      60
ttaaaattga atattactga ttacaatata gatcagactg cataccttgt tgatagtatg     120
tctgatgacg catatcgaca agaaaaaatg atgtttctcg atcaaatcaa atttgcaaag     180
cgcttgagcc aaaaacgcaa cctgttgaat catggagatt ttgaaggatc caattggaca     240
ggtaagaatg gatggaaaag aataattat gtagttgtcg catcggatca tcctatattt      300
aaaggccgat atttacacat accaggtgca acaaccgcga tgagtggcgc aatcattccg     360
acttatgtat atcaaagtat agatgaatcg aagttaaaac cgtatacacg ttatttggta     420
cgagggtttg ttggaaagag tcaagattta gcgttacttg tttcccggta taccaaagaa     480
gtgtacaaga aaatcaatgt accaaatgat aaagactacg atatgacatc gcatataaat     540
agggaagaga atctatggca caatagatat ataaaagaca cttcggttca aaattcaatc     600
tctatgtgca aaaatccaca tgaatttacg tgtcatattg atataggga  actggataga    660
aagaaaggtc ctggtataac catcggtttt caaattggaa caacagatgg gatggcaaca    720
ttagataata tagaagtgat agaagcacat ccgttaaccg gatacgcctt agcacgtatc    780
gaaaaacgtg aacgtaaatg gaaacaaaaa tggctagagc atcgaataca aatcgaaaag    840
gctgtgcaaa cagcgcaaga ggtgattcga aatttattta catgcccaca acaaaatcaa    900
ttgaactgga tgacaacccg aaacgacatt gcacatgcag aaacattgat aaaagagatt    960
tcatatcggt atagccaact ttcttgtgga gatttcccca tactaccaga agaggcgtat   1020
gacatccttc aacaactttc aactgcagtt gaaaccgcaa aagcgttgta tacacaacga   1080
aacgtggtga ataatgggga ttttcaagct ggattatcga attggcatag acagatggt    1140
gcagagatac aacaaattca gaatgcatcc tctgttctaa taattacaga ctgggctgcg   1200
aatatttcac aagacatgcg tgtagttgaa aaaggtagct atctgttgcg cgtaacagcg   1260
aaaaagaag  atgccggaga aggttatatt acaattagtg attgtgccgc attgatagaa   1320
acattgacat ttacaacggg ggaatctgtg gaaagtctga cacattctga tattcattca   1380
aggctccata acgctataa  taaaaaacac ataaaaaacc atccttcaga agaatatgaa   1440
atagaatcgg atcttcattt atttaatagg gcggaacaaa acggttctct cccctctagc   1500
tatgtaacca aaacgatgga atctttccg  gaaaccaatc gaatacgcat tgaaattgga   1560
gaaacaggtg aacatttat  agtggaaagt gtggaattaa ttcgaatgga acagatgaac   1620
gaaacaaaca atccagatgt agatgttcaa attgtaatga atgatacacc cgctacacaa   1680
tttgatccag tttctttac  agaatccacg gtgaggccca gaaatgctca gtatgcatat   1740
tctcatgatt caaatatagg ttatgaaaat cctaactgga tggctgatat ttcaggtgat   1800
actttattta ctgatttatc tatccctggt acacataata caatggctct ttatggagga   1860
gatattacac aatgtcaaac gatgtcactg aatacgcaat tacatgtagg aattcgttat   1920
ttagatattc gctgtaggca catagaaaat gcttttgcga ttcatcatgg acctgtgtac   1980
caaaatgcga tgtttggaga tgtttgtatt gccgtaagga attttttgag aagcaaccct   2040
agtgaaacag tatttatgcg gataaaagaa gaacatacag cagaaaacaa tacaagatct   2100
ttttcagata catttgcaga ttataagtct caatatagcg acttattttg ggattggaca   2160
ggtgataacc caagattaag tgaaataaga ggaaagttg  ttgttttaca aaattttca    2220
ggtggtaaat ttggtatcaa ttacaataca ttgaatactc aagatcaata tcatttaaat   2280
```

```
acaaactggg atttatatga taaatggcta ttcgtcaaag aacatttgta tgccgctgac    2340
aactcttata aaagtggccg taaacaagta tatctgaatt acctaagtgg atcaggtggt    2400
tcatttcctt attttgttgc aagtggacat agtagtccag gtacagatgc tccacaatta    2460
tctacaggtc taacaacacc agcatttgca agctggtatc cggattttcc acggggaagt    2520
tgttttatag gaatttgcac aatttacttt gaaggaacaa atattcttac aagtcagtgg    2580
atagagaaaa atgattttaa atatatagga atcatagctg ctgattttcc aggaagaaca    2640
ttaatttcca atattattag tctgaataaa cttcttagct tagaaattaa aaatggtggt    2700
acctatcaaa ttgtttccgc tttaaataat agtagtgtta tagatatgag tctgagtgga    2760
gatcgaaatg ttcacctatg gtccaataac ggtactctta atcaagtatg gaaattcgtg    2820
tatgattcaa atagattggc ataccaaatt aaaagtctat ccgatgaaaa tttagtacta    2880
acttgggctt attatagtag taatcgagat aatgtaattg ttgcttctaa tcaaaatagc    2940
gatgagcaat attggatacc tgagcgcaca ggcgcatatc attatttaa aaatctcatc    3000 aatccctcgg gagcattaga tgtaagcgga tcaggaacaa caaacggaac gaatattttg    3060
tattggagtt ataacagagc aacgaatcaa aaattcaaac tggaagaagt aaatatacct    3120
ggaggtcaag ctgaaggtgt acttttatat gcagatgcta attatgtagg gaaatctgta    3180
ctactaacaa atagtgtctc aaaccttaga gacgttggta tgaatgatat agccagttct    3240
ataaaattta ttggtcctta tcaagctact ctatatgaac atgataattt tacaggtgcg    3300
gcttttactc tcacatctaa tgttgcaaat ttaaagatg ttggcatgaa tgatacagtt    3360
agttctataa aaattacaaa gacatctgga ggccgagcta caggtatata tttatatgca    3420
gatgctaatt atgtaggcag atctgtatgg ttaacatcta atgttgcaaa tttaaaagat    3480
attggcatga atgatacagt cagttctgta gaaattgttg gcgcatatca agccacttta    3540
tatggggatg ccaattatac agggaaggct tataatctca ctcataatgt tacaaattta    3600
aaagatgttg gcatgaatga tatagtcagt tccataaaaa ttttagtgt gtaa           3654
```

<210> SEQ ID NO 4
<211> LENGTH: 1217
<212> TYPE: PRT
<213> ORGANISM: Bacillus thuringiensis
<220> FEATURE:
<221> NAME/KEY: MISC_FEATURE
<222> LOCATION: (1)..(1217)
<223> OTHER INFORMATION: The amino acid sequence of a TIC7181 protein.

<400> SEQUENCE: 4

```
Met Asp Gln Lys Ile Ile Lys Met Arg Glu Ala Val Asn Ala Leu Phe
1               5                   10                  15

Ser Asn Asn His Leu Lys Leu Asn Ile Thr Asp Tyr Asn Ile Asp Gln
            20                  25                  30

Thr Ala Tyr Leu Val Asp Ser Met Ser Asp Asp Ala Tyr Arg Gln Glu
        35                  40                  45

Lys Met Met Phe Leu Asp Gln Ile Lys Phe Ala Lys Arg Leu Ser Gln
    50                  55                  60

Lys Arg Asn Leu Leu Asn His Gly Asp Phe Glu Gly Ser Asn Trp Thr
65                  70                  75                  80

Gly Lys Asn Gly Trp Lys Arg Asn Asn Tyr Val Val Val Ala Ser Asp
                85                  90                  95

His Pro Ile Phe Lys Gly Arg Tyr Leu His Ile Pro Gly Ala Thr Thr
            100                 105                 110
```

-continued

Ala Met Ser Gly Ala Ile Ile Pro Thr Tyr Val Tyr Gln Ser Ile Asp
            115                 120                 125
Glu Ser Lys Leu Lys Pro Tyr Thr Arg Tyr Leu Val Arg Gly Phe Val
    130                 135                 140
Gly Lys Ser Gln Asp Leu Ala Leu Leu Val Ser Arg Tyr Thr Lys Glu
145                 150                 155                 160
Val Tyr Lys Lys Ile Asn Val Pro Asn Asp Lys Asp Tyr Asp Met Thr
                165                 170                 175
Ser His Ile Asn Arg Glu Glu Asn Leu Trp His Asn Arg Tyr Ile Lys
            180                 185                 190
Asp Thr Ser Val Gln Asn Ser Ile Ser Met Cys Lys Asn Pro His Glu
    195                 200                 205
Phe Thr Cys His Ile Asp Ile Gly Glu Leu Asp Arg Lys Lys Gly Pro
    210                 215                 220
Gly Ile Thr Ile Gly Phe Gln Ile Gly Thr Thr Asp Gly Met Ala Thr
225                 230                 235                 240
Leu Asp Asn Ile Glu Val Ile Glu Ala His Pro Leu Thr Gly Tyr Ala
                245                 250                 255
Leu Ala Arg Ile Glu Lys Arg Glu Arg Lys Trp Lys Gln Lys Trp Leu
            260                 265                 270
Glu His Arg Ile Gln Ile Glu Lys Ala Val Gln Thr Ala Gln Glu Val
    275                 280                 285
Ile Arg Asn Leu Phe Thr Cys Pro Gln Gln Asn Gln Leu Asn Trp Met
    290                 295                 300
Thr Thr Arg Asn Asp Ile Ala His Ala Glu Thr Leu Ile Lys Glu Ile
305                 310                 315                 320
Ser Tyr Arg Tyr Ser Gln Leu Ser Cys Gly Asp Phe Pro Ile Leu Pro
                325                 330                 335
Glu Glu Ala Tyr Asp Ile Leu Gln Gln Leu Ser Thr Ala Val Glu Thr
            340                 345                 350
Ala Lys Ala Leu Tyr Thr Gln Arg Asn Val Val Asn Asn Gly Asp Phe
    355                 360                 365
Gln Ala Gly Leu Ser Asn Trp His Arg Thr Asp Gly Ala Glu Ile Gln
370                 375                 380
Gln Ile Gln Asn Ala Ser Ser Val Leu Ile Ile Thr Asp Trp Ala Ala
385                 390                 395                 400
Asn Ile Ser Gln Asp Met Arg Val Val Glu Lys Gly Ser Tyr Leu Leu
                405                 410                 415
Arg Val Thr Ala Lys Lys Glu Asp Ala Gly Glu Gly Tyr Ile Thr Ile
            420                 425                 430
Ser Asp Cys Ala Ala Leu Ile Glu Thr Leu Thr Phe Thr Thr Gly Glu
    435                 440                 445
Ser Val Glu Ser Leu Thr His Ser Asp Ile His Ser Arg Leu His Lys
    450                 455                 460
Arg Tyr Asn Lys Lys His Ile Lys Asn His Pro Ser Glu Glu Tyr Glu
465                 470                 475                 480
Ile Glu Ser Asp Leu His Leu Phe Asn Arg Ala Glu Gln Asn Gly Ser
                485                 490                 495
Leu Pro Ser Ser Tyr Val Thr Lys Thr Met Glu Ile Phe Pro Glu Thr
            500                 505                 510
Asn Arg Ile Arg Ile Glu Ile Gly Glu Thr Gly Gly Thr Phe Ile Val
    515                 520                 525
Glu Ser Val Glu Leu Ile Arg Met Glu Gln Met Asn Glu Thr Asn Asn

```
                530                 535                 540
Pro Asp Val Asp Val Gln Ile Val Met Asn Asp Thr Pro Ala Thr Gln
545                 550                 555                 560

Phe Asp Pro Val Ser Phe Thr Glu Ser Thr Val Arg Pro Arg Asn Ala
                565                 570                 575

Gln Tyr Ala Tyr Ser His Asp Ser Asn Ile Gly Tyr Glu Asn Pro Asn
                580                 585                 590

Trp Met Ala Asp Ile Ser Gly Asp Thr Leu Phe Thr Asp Leu Ser Ile
                595                 600                 605

Pro Gly Thr His Asn Thr Met Ala Leu Tyr Gly Gly Asp Ile Thr Gln
                610                 615                 620

Cys Gln Thr Met Ser Leu Asn Thr Gln Leu His Val Gly Ile Arg Tyr
625                 630                 635                 640

Leu Asp Ile Arg Cys Arg His Ile Glu Asn Ala Phe Ala Ile His His
                645                 650                 655

Gly Pro Val Tyr Gln Asn Ala Met Phe Gly Asp Val Cys Ile Ala Val
                660                 665                 670

Arg Asn Phe Leu Arg Ser Asn Pro Ser Glu Thr Val Phe Met Arg Ile
                675                 680                 685

Lys Glu Glu His Thr Ala Glu Asn Asn Thr Arg Ser Phe Ser Asp Thr
690                 695                 700

Phe Ala Asp Tyr Lys Ser Gln Tyr Ser Asp Leu Phe Trp Asp Trp Thr
705                 710                 715                 720

Gly Asp Asn Pro Arg Leu Ser Glu Ile Arg Gly Lys Val Val Leu
                725                 730                 735

Gln Asn Phe Ser Gly Gly Lys Phe Gly Ile Asn Tyr Asn Thr Leu Asn
                740                 745                 750

Thr Gln Asp Gln Tyr His Leu Asn Thr Asn Trp Asp Leu Tyr Asp Lys
                755                 760                 765

Trp Leu Phe Val Lys Glu His Leu Tyr Ala Ala Asp Asn Ser Tyr Lys
                770                 775                 780

Ser Gly Arg Lys Gln Val Tyr Leu Asn Tyr Leu Ser Gly Ser Gly Gly
785                 790                 795                 800

Ser Phe Pro Tyr Phe Val Ala Ser Gly His Ser Ser Pro Gly Thr Asp
                805                 810                 815

Ala Pro Gln Leu Ser Thr Gly Leu Thr Thr Pro Ala Phe Ala Ser Trp
                820                 825                 830

Tyr Pro Asp Phe Pro Arg Gly Ser Cys Phe Ile Gly Ile Cys Thr Ile
                835                 840                 845

Tyr Phe Glu Gly Thr Asn Ile Leu Thr Ser Gln Trp Ile Glu Lys Asn
850                 855                 860

Asp Phe Lys Tyr Ile Gly Ile Ile Ala Ala Asp Phe Pro Gly Arg Thr
865                 870                 875                 880

Leu Ile Ser Asn Ile Ile Ser Leu Asn Lys Leu Leu Ser Leu Glu Ile
                885                 890                 895

Lys Asn Gly Gly Thr Tyr Gln Ile Val Ser Ala Leu Asn Asn Ser Ser
                900                 905                 910

Val Ile Asp Met Ser Leu Ser Gly Asp Arg Asn Val His Leu Trp Ser
                915                 920                 925

Asn Asn Gly Thr Leu Asn Gln Val Trp Lys Phe Val Tyr Asp Ser Asn
                930                 935                 940

Arg Leu Ala Tyr Gln Ile Lys Ser Leu Ser Asp Glu Asn Leu Val Leu
945                 950                 955                 960
```

```
Thr Trp Ala Tyr Tyr Ser Ser Asn Arg Asp Asn Val Ile Val Ala Ser
                965                 970                 975

Asn Gln Asn Ser Asp Glu Gln Tyr Trp Ile Pro Glu Arg Thr Gly Ala
            980                 985                 990

Tyr His Tyr Phe Lys Asn Leu Ile  Asn Pro Ser Gly Ala  Leu Asp Val
        995                 1000                 1005

Ser Gly Ser Gly Thr Thr Asn  Gly Thr Asn Ile Leu  Tyr Trp Ser
    1010             1015                 1020

Tyr Asn Arg Ala Thr Asn Gln  Lys Phe Lys Leu Glu  Glu Val Asn
    1025             1030                 1035

Ile Pro Gly Gly Gln Ala Glu  Gly Val Leu Leu Tyr  Ala Asp Ala
    1040             1045                 1050

Asn Tyr Val Gly Lys Ser Val  Leu Leu Thr Asn Ser  Val Ser Asn
    1055             1060                 1065

Leu Arg Asp Val Gly Met Asn  Asp Ile Ala Ser Ser  Ile Lys Phe
    1070             1075                 1080

Ile Gly Pro Tyr Gln Ala Thr  Leu Tyr Glu His Asp  Asn Phe Thr
    1085             1090                 1095

Gly Ala Ala Phe Thr Leu Thr  Ser Asn Val Ala Asn  Leu Lys Asp
    1100             1105                 1110

Val Gly Met Asn Asp Thr Val  Ser Ser Ile Lys Ile  Thr Lys Thr
    1115             1120                 1125

Ser Gly Gly Arg Ala Thr Gly  Ile Tyr Leu Tyr Ala  Asp Ala Asn
    1130             1135                 1140

Tyr Val Gly Arg Ser Val Trp  Leu Thr Ser Asn Val  Ala Asn Leu
    1145             1150                 1155

Lys Asp Ile Gly Met Asn Asp  Thr Val Ser Ser Val  Glu Ile Val
    1160             1165                 1170

Gly Ala Tyr Gln Ala Thr Leu  Tyr Gly Asp Ala Asn  Tyr Thr Gly
    1175             1180                 1185

Lys Ala Tyr Asn Leu Thr His  Asn Val Thr Asn Leu  Lys Asp Val
    1190             1195                 1200

Gly Met Asn Asp Ile Val Ser  Ser Ile Lys Ile Phe  Ser Val
    1205             1210                 1215

<210> SEQ ID NO 5
<211> LENGTH: 3654
<212> TYPE: DNA
<213> ORGANISM: Bacillus thuringiensis
<220> FEATURE:
<221> NAME/KEY: misc_feature
<222> LOCATION: (1)..(3654)
<223> OTHER INFORMATION: The native nucleotide sequence encoding TIC4904
      toxin protein obtained from Bacillus thuringiensis species
      CFB007432.

<400> SEQUENCE: 5
atggatcaaa agattataaa aatgcgagaa gcagtcaatg ccttgttttc caataatcag      60
ttaaaattga atattactga ttacaatata gatcagattg catacttgt tgatagtatg     120 tctgatgacg catatcgaca agaaaaaatg aggtttctcg atcaaatcaa atttgcaaag    180
cgcttgagtc aaaaacgcaa cctgttgaat tatggagatt ttgaaggatc caattggcca    240
ggtaagaatg gatggaaaag aataattat gtagttgtcg catcggatca tcctatattt     300
aaaggccgat atttcacat accaagtgca acaaccacga tgagtggcgc aatcattccg     360
acttatgtat atcaacgtat agatgaatcg aagttaaaac cgtatacacg ttatttggta    420
```

```
cgagggtatg ttggaaagag tcaagattta gcgttacttg tttcccggta taccaaagaa      480
gtgtacaaga aaatcaatgt accaaatgat gaagattacg atatcacatc gcatataaat      540
agggaagaga atctatggca caatagatat ataagaggca cccaggttca aaattcaatc      600
tctatgtgca acaatccaca tgaatttacg tgtcatattg atataggga actggataga      660 aagaaaggtc ctggtataac catcggtttt caaattggaa caacagatgg gatggcaaca      720
ttagataata tagaagtgat agaagcacat ccgttaactg atcggcctt agcacgtatc       780 gaaaaacgtg aacgtaaatg gaaacaaaaa tggctagaga atcaaataca aatcgaaaag      840
gctgtgcaaa cagtgcaaga ggtgattcga aatttattta catgcccaca acaaaatcaa      900
ttgaactgga tgacaacccg aaacgacatt gcacatgcag aaacattgat aaaagagatt      960
ccatatcggt atagtcaact ttcttgtgga gatttcccca tactaccaga agaggcatat     1020
gacatccttc aacaactttc aactgcagtt gaaaccgcaa aaacgttgta tacacagcga     1080
aatgtggtga agaatgggga ttttcaagct ggattatcaa attggcatag acagatggt      1140 gcagagatac aacaaattca gaatacatcc tctgttctgg taattacaga ctgggctgcg     1200
aatatttcac aagacatgcg tgtagttgaa aaaggtggat atctgttgcg cgtaacagcg     1260
aaaaaagaaa atccgggaga aggttatata actattagtg attgtgccgc attgacagaa     1320
acactgaaat ttacagcggg ggaatctgta gaaagtctga cacattctga tatttattca     1380
aggctccata gcgctctga taaagaacaa ataacaaacc atctttcaaa agaatatgaa      1440
atagaatcgg atcctcattt attaaatagg gcagaacaaa atggttctct ccctttagc      1500 tatgtaacca aaacaattga aatttttccg gaaaccaatc gagtacgcat tgaaattgga     1560
gaaacaggtg aacatttat agtggaaagt gtggaattga ttcaaatgga acaggtaaac      1620
gaaacaaaca atccaactgt agatgttcaa attgtaatga atgatacacc cgctacaaaa     1680
tttaatccag tttcttttac agaatcaacg gtgagtccta gaactgttca ttatgcgtat     1740
tcacatgatt caagtatagg ttatgaaaac cctaactgga tggatgatat ttcaggtgat     1800 actttatta gtgatttatc tctccctggt acacataata caatggctct ttatggagga      1860
gatattacac aatgccaaac gatgtcactg agtacgcaat tacaagtagg aattcgttat     1920
ttagatattc gctgtaggca catagaaaat gttttttgcta ttcatcatgg acctgtgtac    1980
caaaatgcga tgtttggaga tgtttgtatt gccgtaagga atttttttgaa aagcaaccct   2040 agtgaaacag tatttatgcg gattaaagaa gaacatacag cagaaaacaa tacaagatct     2100
ttttcagata catttgcaga ttataagtct caatatagcg acttattttg ggattggaca     2160
ggtgataatc caagattaag tgaaataaga ggaaaagttg ttgttttgca aaattttata     2220
ggtgctaaat ttggtatcca ttacgataca ttgaataaac aagatcaata tcatttaaat    2280
acaaactggg atttatatga taatggata ttcgtcaaag aacatttgta tgccgctgac     2340
aactcttata aaagtggccg taaacaagta tatctgaatt acctaagtgg atcaggtggt     2400
tcatttcctt attttgttgc aagtggacat agtagtccag gtacagatgc tccacaatta    2460
tctacaggtc taacaacacc agcatttgca agctggtatc cggattttcc acggggaagt    2520
tgttttatag gaatttgcac aatttacttt gaaggaacaa atattcttac aagtcagtgg     2580
atagagaaaa atgattttaa atatataggga atcatagctg ctgattttcc aggaagaaca   2640
ttaatttcca atattattag tctgaataaa cttcttagct tagaaattaa aaatggtggt     2700
acctatcaaa ttgtttccgc tttaaataat agtagtgtta tagatatgag tctgagtgga    2760
```

-continued

```
gatcgaaatg ttcacctatg gtccaataac ggtactctta atcaagtatg gaaattcgtg    2820
tatgattcaa atagattagc atatcaaatt aaaagtctat ccgatgaaaa tttagtacta    2880
acttgggctt attatagtag taatcgagat aatgtaattg ttgcttctaa tcaaaatagc    2940
gatgagcaat attggatacc tgagcgcaca ggcgcatatc attattttaa aaatctcatc    3000
aatccctcgg gagcattaga tgtaagcgga tcaggaacaa caaacggaac gaatattttg    3060
tattggagtt ataacagagc aacgaatcaa aaattcaaac tggaagaagt aaatatacct    3120
ggaggtcaag ctgaaggtgt acttttatat gcagatgcta attatgtagg gaaatctgta    3180
ctactaacaa atagtgtctc aaaccttaga gacgttggta tgaatgatat agccagttct    3240
ataaaattta ttggtcctta tcaagctact ctatatgaac atgataattt tacaggtgcg    3300 gttttactc ccacatctaa tgttgcaaat ttaaaagatg ttggcatgaa tgatacagtt    3360
agttccataa aaattacaaa gacatctgga ggccgagcta caggtatata tttatatgca    3420
gatgctaatt atgtaggcag atctgtatgg ttaacatcaa atgttgcaaa tttaaaagat    3480
gttggcatga atgatacagt cagttctgta gaaattgttg cgcgtatca ggccacttta    3540 tatgggatt ccaattatac agggaaggct tataatctca ctcataatgt tgcaaattta    3600
aaagatgttg gcatgaatga tatagtcagt tccataaaaa ttttagtgt gtaa          3654
```

<210> SEQ ID NO 6
<211> LENGTH: 1217
<212> TYPE: PRT
<213> ORGANISM: Bacillus thuringiensis
<220> FEATURE:
<221> NAME/KEY: MISC_FEATURE
<222> LOCATION: (1)..(1217)
<223> OTHER INFORMATION: The amino acid sequence of a TIC4904 protein.

<400> SEQUENCE: 6

```
Met Asp Gln Lys Ile Ile Lys Met Arg Glu Ala Val Asn Ala Leu Phe
1               5                   10                  15

Ser Asn Asn Gln Leu Lys Leu Asn Ile Thr Asp Tyr Asn Ile Asp Gln
            20                  25                  30

Ile Ala Tyr Leu Val Asp Ser Met Ser Asp Asp Ala Tyr Arg Gln Glu
        35                  40                  45

Lys Met Arg Phe Leu Asp Gln Ile Lys Phe Ala Lys Arg Leu Ser Gln
    50                  55                  60

Lys Arg Asn Leu Leu Asn Tyr Gly Asp Phe Glu Gly Ser Asn Trp Pro
65                  70                  75                  80

Gly Lys Asn Gly Trp Lys Arg Asn Asn Tyr Val Val Ala Ser Asp
            85                  90                  95

His Pro Ile Phe Lys Gly Arg Tyr Leu His Ile Pro Ser Ala Thr Thr
            100                 105                 110

Thr Met Ser Gly Ala Ile Ile Pro Thr Tyr Val Tyr Gln Arg Ile Asp
        115                 120                 125

Glu Ser Lys Leu Lys Pro Tyr Thr Arg Tyr Leu Val Arg Gly Tyr Val
    130                 135                 140

Gly Lys Ser Gln Asp Leu Ala Leu Leu Val Ser Arg Tyr Thr Lys Glu
145                 150                 155                 160

Val Tyr Lys Lys Ile Asn Val Pro Asn Asp Glu Asp Tyr Asp Ile Thr
                165                 170                 175

Ser His Ile Asn Arg Glu Glu Asn Leu Trp His Asn Arg Tyr Ile Arg
            180                 185                 190

Gly Thr Gln Val Gln Asn Ser Ile Ser Met Cys Asn Asn Pro His Glu
```

```
            195                 200                 205
Phe Thr Cys His Ile Asp Ile Gly Glu Leu Asp Arg Lys Lys Gly Pro
210                 215                 220
Gly Ile Thr Ile Gly Phe Gln Ile Gly Thr Thr Asp Gly Met Ala Thr
225                 230                 235                 240
Leu Asp Asn Ile Glu Val Ile Glu Ala His Pro Leu Thr Gly Ser Ala
                    245                 250                 255
Leu Ala Arg Ile Glu Lys Arg Glu Arg Lys Trp Lys Gln Lys Trp Leu
                260                 265                 270
Glu Asn Gln Ile Gln Ile Glu Lys Ala Val Gln Thr Val Gln Glu Val
            275                 280                 285
Ile Arg Asn Leu Phe Thr Cys Pro Gln Gln Asn Gln Leu Asn Trp Met
290                 295                 300
Thr Thr Arg Asn Asp Ile Ala His Ala Glu Thr Leu Ile Lys Glu Ile
305                 310                 315                 320
Pro Tyr Arg Tyr Ser Gln Leu Ser Cys Gly Asp Phe Pro Ile Leu Pro
                    325                 330                 335
Glu Glu Ala Tyr Asp Ile Leu Gln Gln Leu Ser Thr Ala Val Glu Thr
                340                 345                 350
Ala Lys Thr Leu Tyr Thr Gln Arg Asn Val Val Lys Asn Gly Asp Phe
            355                 360                 365
Gln Ala Gly Leu Ser Asn Trp His Arg Thr Asp Gly Ala Glu Ile Gln
370                 375                 380
Gln Ile Gln Asn Thr Ser Ser Val Leu Val Ile Thr Asp Trp Ala Ala
385                 390                 395                 400
Asn Ile Ser Gln Asp Met Arg Val Val Glu Lys Gly Gly Tyr Leu Leu
                    405                 410                 415
Arg Val Thr Ala Lys Lys Glu Asn Pro Gly Glu Gly Tyr Ile Thr Ile
                420                 425                 430
Ser Asp Cys Ala Ala Leu Thr Glu Thr Leu Lys Phe Thr Ala Gly Glu
            435                 440                 445
Ser Val Glu Ser Leu Thr His Ser Asp Ile Tyr Ser Arg Leu His Lys
450                 455                 460
Arg Ser Asp Lys Glu Gln Ile Thr Asn His Leu Ser Lys Glu Tyr Glu
465                 470                 475                 480
Ile Glu Ser Asp Pro His Leu Leu Asn Arg Ala Glu Gln Asn Gly Ser
                    485                 490                 495
Leu Pro Phe Ser Tyr Val Thr Lys Thr Ile Glu Ile Phe Pro Glu Thr
                500                 505                 510
Asn Arg Val Arg Ile Glu Ile Gly Glu Thr Gly Gly Thr Phe Ile Val
            515                 520                 525
Glu Ser Val Glu Leu Ile Gln Met Glu Gln Val Glu Thr Asn Asn
530                 535                 540
Pro Thr Val Asp Val Gln Ile Val Met Asn Asp Thr Pro Ala Thr Lys
545                 550                 555                 560
Phe Asn Pro Val Ser Phe Thr Glu Ser Thr Val Ser Pro Arg Thr Val
                    565                 570                 575
His Tyr Ala Tyr Ser His Asp Ser Ser Ile Gly Tyr Glu Asn Pro Asn
                580                 585                 590
Trp Met Asp Asp Ile Ser Gly Asp Thr Leu Phe Ser Asp Leu Ser Leu
            595                 600                 605
Pro Gly Thr His Asn Thr Met Ala Leu Tyr Gly Gly Asp Ile Thr Gln
610                 615                 620
```

```
Cys Gln Thr Met Ser Leu Ser Thr Gln Leu Gln Val Gly Ile Arg Tyr
625                 630                 635                 640

Leu Asp Ile Arg Cys Arg His Ile Glu Asn Val Phe Ala Ile His His
            645                 650                 655

Gly Pro Val Tyr Gln Asn Ala Met Phe Gly Asp Val Cys Ile Ala Val
                660                 665                 670

Arg Asn Phe Leu Lys Ser Asn Pro Ser Glu Thr Val Phe Met Arg Ile
                675                 680                 685

Lys Glu Glu His Thr Ala Glu Asn Asn Thr Arg Ser Phe Ser Asp Thr
690                 695                 700

Phe Ala Asp Tyr Lys Ser Gln Tyr Ser Asp Leu Phe Trp Asp Trp Thr
705                 710                 715                 720

Gly Asp Asn Pro Arg Leu Ser Glu Ile Arg Gly Lys Val Val Leu
                725                 730                 735

Gln Asn Phe Ile Gly Ala Lys Phe Gly Ile His Tyr Asp Thr Leu Asn
                740                 745                 750

Lys Gln Asp Gln Tyr His Leu Asn Thr Asn Trp Asp Leu Tyr Asp Lys
                755                 760                 765

Trp Ile Phe Val Lys Glu His Leu Tyr Ala Ala Asp Asn Ser Tyr Lys
770                 775                 780

Ser Gly Arg Lys Gln Val Tyr Leu Asn Tyr Leu Ser Gly Ser Gly Gly
785                 790                 795                 800

Ser Phe Pro Tyr Phe Val Ala Ser Gly His Ser Ser Pro Gly Thr Asp
                805                 810                 815

Ala Pro Gln Leu Ser Thr Gly Leu Thr Thr Pro Ala Phe Ala Ser Trp
                820                 825                 830

Tyr Pro Asp Phe Pro Arg Gly Ser Cys Phe Gly Ile Cys Thr Ile
                835                 840                 845

Tyr Phe Glu Gly Thr Asn Ile Leu Thr Ser Gln Trp Ile Glu Lys Asn
850                 855                 860

Asp Phe Lys Tyr Ile Gly Ile Ile Ala Ala Asp Phe Pro Gly Arg Thr
865                 870                 875                 880

Leu Ile Ser Asn Ile Ile Ser Leu Asn Lys Leu Leu Ser Leu Glu Ile
                885                 890                 895

Lys Asn Gly Gly Thr Tyr Gln Ile Val Ser Ala Leu Asn Asn Ser Ser
                900                 905                 910

Val Ile Asp Met Ser Leu Ser Gly Asp Arg Asn Val His Leu Trp Ser
                915                 920                 925

Asn Asn Gly Thr Leu Asn Gln Val Trp Lys Phe Val Tyr Asp Ser Asn
                930                 935                 940

Arg Leu Ala Tyr Gln Ile Lys Ser Leu Ser Asp Glu Asn Leu Val Leu
945                 950                 955                 960

Thr Trp Ala Tyr Tyr Ser Ser Asn Arg Asp Asn Val Ile Val Ala Ser
                965                 970                 975

Asn Gln Asn Ser Asp Glu Gln Tyr Trp Ile Pro Glu Arg Thr Gly Ala
                980                 985                 990

Tyr His Tyr Phe Lys Asn Leu Ile Asn Pro Ser Gly Ala Leu Asp Val
                995                 1000                1005

Ser Gly Ser Gly Thr Thr Asn Gly Thr Asn Ile Leu Tyr Trp Ser
        1010                1015                1020

Tyr Asn Arg Ala Thr Asn Gln Lys Phe Lys Leu Glu Glu Val Asn
        1025                1030                1035
```

```
Ile Pro Gly Gly Gln Ala Glu Gly Val Leu Leu Tyr Ala Asp Ala
    1040            1045                1050

Asn Tyr Val Gly Lys Ser Val Leu Leu Thr Asn Ser Val Ser Asn
    1055            1060                1065

Leu Arg Asp Val Gly Met Asn Asp Ile Ala Ser Ser Ile Lys Phe
    1070            1075                1080

Ile Gly Pro Tyr Gln Ala Thr Leu Tyr Glu His Asp Asn Phe Thr
    1085            1090                1095

Gly Ala Val Phe Thr Pro Thr Ser Asn Val Ala Asn Leu Lys Asp
    1100            1105                1110

Val Gly Met Asn Asp Thr Val Ser Ser Ile Lys Ile Thr Lys Thr
    1115            1120                1125

Ser Gly Gly Arg Ala Thr Gly Ile Tyr Leu Tyr Ala Asp Ala Asn
    1130            1135                1140

Tyr Val Gly Arg Ser Val Trp Leu Thr Ser Asn Val Ala Asn Leu
    1145            1150                1155

Lys Asp Val Gly Met Asn Asp Thr Val Ser Ser Val Glu Ile Val
    1160            1165                1170

Gly Ala Tyr Gln Ala Thr Leu Tyr Gly Asp Ser Asn Tyr Thr Gly
    1175            1180                1185

Lys Ala Tyr Asn Leu Thr His Asn Val Ala Asn Leu Lys Asp Val
    1190            1195                1200

Gly Met Asn Asp Ile Val Ser Ser Ile Lys Ile Phe Ser Val
    1205            1210                1215

<210> SEQ ID NO 7
<211> LENGTH: 3636
<212> TYPE: DNA
<213> ORGANISM: Bacillus thuringiensis
<220> FEATURE:
<221> NAME/KEY: misc_feature
<222> LOCATION: (1)..(3636)
<223> OTHER INFORMATION: The native nucleotide sequence encoding TIC6547
      toxin protein obtained from Bacillus thuringiensis species
      CFB231019.

<400> SEQUENCE: 7
atggatcaaa agattataaa aatgcgagaa gcagtcaatg ccttgttttc caataatcag      60
ttaaaattga atattactga ttacaatata gatcagattg cataccttgt tgatagtatg     120
tctgatgacg catatcgaca agaaaaaatg aggtttctcg atcaaatcaa atttgcaaag     180
cgcttgagtc aaaaacgcaa cctgttgaat tatggagatt ttgaaggatc caattggcca     240
ggtaagaatg gatggaaaag aaataattat gtagttgtcg catcggatca tcctatattt     300
aaaggccgat atttacacat accaagtgca acaaccacga tgagtggcgc aatcattccg     360
acttatgtat atcaacgtat agatgaatcg aagttaaaac cgtatacacg ttatttggta     420
cgagggtatg ttggaaagag tcaagattta gcgttacttg tttcccggta taccaaagaa     480
gtgtacaaga aaatcaatgt accaaatgat gaggattacg atatcacatc gcatataaat     540
agggaagaga atttatggca aatagatat ataagaggca cccaagttca aaattcaatc     600
tctatgtgca acaatccaca tgaatttacg tgtcatattg atataggaga actggataga     660
aagaaaggtc ctggtataac catcggtttt caaattggaa caacagatgg gatggcaaca     720
ttagataata tagaagtgat agaagcacat ccgttaactg gatcggcctt agcacgtatc     780
caaaaacgtg aacgtaaatg gaaacaaaaa tggatagaga atcgaatgca aatcgaaaag     840
gctgtacaaa cagcgcaaga ggtgattcga aatttattta catgcccaca acaaaatcaa     900
```

```
ttgaactgga tgacaactcg aaacgacatt acacatgcag aaacattgat aaaagagatt    960
ccatatcggt atagccaact ttcttgtgga gatttcccca cactaccaga agaggcgtat   1020
gacatccttc aacaactttc aactgcagtt gaaaccgcaa aagcgttata tgcacaacga   1080
aatgtggtga ataatgggga ttttcaagct ggattatcga attggtatac gacagatggt   1140
gcagagatac aacaaataca gaattcgtcc tctgttctag taattaaaga ctgggctaca   1200
aatatttcac aggacatgcg tgtggttgaa aaggtggct atctgctacg cgtaacagcg    1260
aaaaagaag ataccggaga aggttatata acaattagtg attgtgcagc attggtagaa    1320
aaattgacat ttacaacggg ggaagctgta gaaagtctgg cacattctga tagtcgttca   1380
aggctccata agcgctatga taaaaaatca aaggatatg aaatagaatc ggatcctcat    1440
ttatttaata gggcgaaaca aaacggttct cttccttcta gctatgtaac caaaacgatt   1500
gaaatctttc cggaaaccaa tcgagtacgc attgagattg agaaacagg tggaaagttt    1560
atggtggaaa gtgtggaatt gattcgaatg aacagatga acgaaacaaa taatccagct    1620
gtagatgttc aaactgtaat gaatgataca cctgctacac aatttgatcc agtttctttt   1680
acagaatcaa cggtgagtcc cagaaatgct cagtatgcgt attctcatga tacaaatata   1740
ggctatgaaa tcctaactg gatggctgat atttcaggtg atactttatt tagtgattta    1800
tctatccctg gtacacataa tacaatggct cttcatggag gagatattac acaatgtcaa   1860
acgatgtcac tgaatacaca attacatgta ggaattcgtt atttagatat tcgctgtagg   1920
catatcgata atgtttttgc gattcatcat gggcctgtgt accaaaatac gatgtttgga   1980
gatgtttgta tagccgtaag ggattttttg aggaacaacc ctagtgaaac agtatttatg   2040
cggataaaag aagaacatac accagaaaat aatacaagat ctttttcgga tacatttgca   2100
gattataagt ctcaatatag cgacttattt tggaattgga caggtgataa cccaagatta   2160
agtgaaataa gaggaaaagt tgttgttttg caaaacttttt cagggatag gtttggtatc   2220
tactacaata cactgaatac acaagatcaa tatcatttag atacaaactg ggatttatat   2280
gataaatggc tatttgtaaa agagcatttg tataaagctg acgacgctta taaaagtggt   2340
ggtaaacaag catatctgaa ttatctaagt gggtcaggtg gttcttttcc ttattttgtt   2400
gcaagtggac atagtagtcc tggtacagat gctccacaat tatctacagg tctaacaaca   2460
ccagcatttg caagctggta tccggatttt ccacggggaa gttgttttat aggaatttgc   2520
acaatttact ttgaaggaac aaatattctt acaagtcagt ggatagagaa aaatgatttt   2580
aaatatatag gaatcatagc tgctgatttt ccaggaagaa cattaatttc caatattatt   2640
agtttgaata aacttcttag cttagaaatt aaaaatggtg gtacctatca aattgtttcc   2700
gctttaaata atagtagtgt tatagatatg agtctgagtg gagatcgaaa tgctcaccta   2760
tggtccaata acggtactcc taatcaagta tggaaattcg tgtatgattc aaatagatta   2820
gcataccaaa ttaaaagttt atccgatgaa aatttagtac taacttgggc ttattatagt   2880
agtaatcgag ataatgtaat tgtcgcttct aatcaaaata gcgatgagca atattggata   2940
cctgagcgca caggcgcata tcattatttt aaaaatctca tcaatccctc aggagcatta   3000
gatgtaagcg atcaggaac aacaaacgga acgaatattt gtattggag ttataacaga     3060
gcaacgaatc aaaaattcaa actggaagaa gtaaatatat ctggaggtca aactgaaggt   3120
gtacttttat atgcagaggc taattatgta gggaaatctg tactactaac aaatagtgtc   3180
tccaacctta gagacgttgg tatgaatgat atagctagtt ctataaaatt tattggtcct   3240
```

-continued

```
tatcaagcta ctctatatga acatgatgat tttacaggtg cggtttttac tcccacatct   3300
aatgttgcaa atttaaaaga tgttggcatg aatgatacag ttagttctat aaaaattaca   3360
aagacatctg gaggccgagc tacaggtata tatttatatg cagatgctaa ttatgtaggc   3420
agatctgtat ggttaacatc taatgttgca aatttaaaag atgttggcat gaatgataca   3480
gtcagttctg tagaaattgt tggcgcgtat caggccactt tatatgggga ttccaattat   3540
acagggaagg cttataatct cactcataat gttgcaaatt taaaagatgt tggcatgaat   3600
gatatagtca gttccataaa aatttttagt gtgtaa                             3636

<210> SEQ ID NO 8
<211> LENGTH: 1211
<212> TYPE: PRT
<213> ORGANISM: Bacillus thuringiensis
<220> FEATURE:
<221> NAME/KEY: MISC_FEATURE
<222> LOCATION: (1)..(1211)
<223> OTHER INFORMATION: The amino acid sequence of a TIC6547 protein.

<400> SEQUENCE: 8

Met Asp Gln Lys Ile Ile Lys Met Arg Glu Ala Val Asn Ala Leu Phe
1               5                   10                  15

Ser Asn Asn Gln Leu Lys Leu Asn Ile Thr Asp Tyr Asn Ile Asp Gln
            20                  25                  30

Ile Ala Tyr Leu Val Asp Ser Met Ser Asp Asp Ala Tyr Arg Gln Glu
        35                  40                  45

Lys Met Arg Phe Leu Asp Gln Ile Lys Phe Ala Lys Arg Leu Ser Gln
    50                  55                  60

Lys Arg Asn Leu Leu Asn Tyr Gly Asp Phe Glu Gly Ser Asn Trp Pro
65                  70                  75                  80

Gly Lys Asn Gly Trp Lys Arg Asn Asn Tyr Val Val Val Ala Ser Asp
                85                  90                  95

His Pro Ile Phe Lys Gly Arg Tyr Leu His Ile Pro Ser Ala Thr Thr
            100                 105                 110

Thr Met Ser Gly Ala Ile Ile Pro Thr Tyr Val Tyr Gln Arg Ile Asp
        115                 120                 125

Glu Ser Lys Leu Lys Pro Tyr Thr Arg Tyr Leu Val Arg Gly Tyr Val
    130                 135                 140

Gly Lys Ser Gln Asp Leu Ala Leu Leu Val Ser Arg Tyr Thr Lys Glu
145                 150                 155                 160

Val Tyr Lys Lys Ile Asn Val Pro Asn Asp Glu Asp Tyr Asp Ile Thr
                165                 170                 175

Ser His Ile Asn Arg Glu Glu Asn Leu Trp His Asn Arg Tyr Ile Arg
            180                 185                 190

Gly Thr Gln Val Gln Asn Ser Ile Ser Met Cys Asn Asn Pro His Glu
        195                 200                 205

Phe Thr Cys His Ile Asp Ile Gly Glu Leu Asp Arg Lys Lys Gly Pro
    210                 215                 220

Gly Ile Thr Ile Gly Phe Gln Ile Gly Thr Thr Asp Gly Met Ala Thr
225                 230                 235                 240

Leu Asp Asn Ile Glu Val Ile Glu Ala His Pro Leu Thr Gly Ser Ala
                245                 250                 255

Leu Ala Arg Ile Gln Lys Arg Glu Arg Lys Trp Lys Gln Lys Trp Ile
            260                 265                 270

Glu Asn Arg Met Gln Ile Glu Lys Ala Val Gln Thr Ala Gln Glu Val
        275                 280                 285
```

```
Ile Arg Asn Leu Phe Thr Cys Pro Gln Gln Asn Gln Leu Asn Trp Met
    290                 295                 300

Thr Thr Arg Asn Asp Ile Thr His Ala Glu Thr Leu Ile Lys Glu Ile
305                 310                 315                 320

Pro Tyr Arg Tyr Ser Gln Leu Ser Cys Gly Asp Phe Pro Thr Leu Pro
                325                 330                 335

Glu Glu Ala Tyr Asp Ile Leu Gln Gln Leu Ser Thr Ala Val Glu Thr
                340                 345                 350

Ala Lys Ala Leu Tyr Ala Gln Arg Asn Val Val Asn Asn Gly Asp Phe
                355                 360                 365

Gln Ala Gly Leu Ser Asn Trp Tyr Thr Thr Asp Gly Ala Glu Ile Gln
    370                 375                 380

Gln Ile Gln Asn Ser Ser Ser Val Leu Val Ile Lys Asp Trp Ala Thr
385                 390                 395                 400

Asn Ile Ser Gln Asp Met Arg Val Val Glu Lys Gly Gly Tyr Leu Leu
                405                 410                 415

Arg Val Thr Ala Lys Lys Glu Asp Thr Gly Glu Gly Tyr Ile Thr Ile
                420                 425                 430

Ser Asp Cys Ala Ala Leu Val Glu Lys Leu Thr Phe Thr Thr Gly Glu
                435                 440                 445

Ala Val Glu Ser Leu Ala His Ser Asp Ser Arg Ser Arg Leu His Lys
                450                 455                 460

Arg Tyr Asp Lys Lys Ser Glu Gly Tyr Glu Ile Glu Ser Asp Pro His
465                 470                 475                 480

Leu Phe Asn Arg Ala Lys Gln Asn Gly Ser Leu Pro Ser Ser Tyr Val
                485                 490                 495

Thr Lys Thr Ile Glu Ile Phe Pro Glu Thr Asn Arg Val Arg Ile Glu
                500                 505                 510

Ile Gly Glu Thr Gly Gly Lys Phe Met Val Glu Ser Val Glu Leu Ile
                515                 520                 525

Arg Met Glu Gln Met Asn Glu Thr Asn Asn Pro Ala Val Asp Val Gln
                530                 535                 540

Thr Val Met Asn Asp Thr Pro Ala Thr Gln Phe Asp Pro Val Ser Phe
545                 550                 555                 560

Thr Glu Ser Thr Val Ser Pro Arg Asn Ala Gln Tyr Ala Tyr Ser His
                565                 570                 575

Asp Thr Asn Ile Gly Tyr Glu Asn Pro Asn Trp Met Ala Asp Ile Ser
                580                 585                 590

Gly Asp Thr Leu Phe Ser Asp Leu Ser Ile Pro Gly Thr His Asn Thr
                595                 600                 605

Met Ala Leu His Gly Gly Asp Ile Thr Gln Cys Gln Thr Met Ser Leu
610                 615                 620

Asn Thr Gln Leu His Val Gly Ile Arg Tyr Leu Asp Ile Arg Cys Arg
625                 630                 635                 640

His Ile Asp Asn Val Phe Ala Ile His His Gly Pro Val Tyr Gln Asn
                645                 650                 655

Thr Met Phe Gly Asp Val Cys Ile Ala Val Arg Asp Phe Leu Arg Asn
                660                 665                 670

Asn Pro Ser Glu Thr Val Phe Met Arg Ile Lys Glu Glu His Thr Pro
                675                 680                 685

Glu Asn Asn Thr Arg Ser Phe Ser Asp Thr Phe Ala Asp Tyr Lys Ser
690                 695                 700
```

```
Gln Tyr Ser Asp Leu Phe Trp Asn Trp Thr Gly Asp Asn Pro Arg Leu
705                 710                 715                 720

Ser Glu Ile Arg Gly Lys Val Val Leu Gln Asn Phe Ser Gly Asp
            725                 730                 735

Arg Phe Gly Ile Tyr Tyr Asn Thr Leu Asn Thr Gln Asp Gln Tyr His
                740                 745                 750

Leu Asp Thr Asn Trp Asp Leu Tyr Asp Lys Trp Leu Phe Val Lys Glu
        755                 760                 765

His Leu Tyr Lys Ala Asp Asp Ala Tyr Lys Ser Gly Gly Lys Gln Ala
    770                 775                 780

Tyr Leu Asn Tyr Leu Ser Gly Ser Gly Gly Ser Phe Pro Tyr Phe Val
785                 790                 795                 800

Ala Ser Gly His Ser Ser Pro Gly Thr Asp Ala Pro Gln Leu Ser Thr
                805                 810                 815

Gly Leu Thr Thr Pro Ala Phe Ala Ser Trp Tyr Pro Asp Phe Pro Arg
                820                 825                 830

Gly Ser Cys Phe Ile Gly Ile Cys Thr Ile Tyr Phe Glu Gly Thr Asn
                835                 840                 845

Ile Leu Thr Ser Gln Trp Ile Glu Lys Asn Asp Phe Lys Tyr Ile Gly
850                 855                 860

Ile Ile Ala Ala Asp Phe Pro Gly Arg Thr Leu Ile Ser Asn Ile Ile
865                 870                 875                 880

Ser Leu Asn Lys Leu Leu Ser Leu Glu Ile Lys Asn Gly Gly Thr Tyr
                885                 890                 895

Gln Ile Val Ser Ala Leu Asn Asn Ser Ser Val Ile Asp Met Ser Leu
                900                 905                 910

Ser Gly Asp Arg Asn Ala His Leu Trp Ser Asn Asn Gly Thr Pro Asn
            915                 920                 925

Gln Val Trp Lys Phe Val Tyr Asp Ser Asn Arg Leu Ala Tyr Gln Ile
            930                 935                 940

Lys Ser Leu Ser Asp Glu Asn Leu Val Leu Thr Trp Ala Tyr Tyr Ser
945                 950                 955                 960

Ser Asn Arg Asp Asn Val Ile Val Ala Ser Gln Asn Ser Asp Glu
            965                 970                 975

Gln Tyr Trp Ile Pro Glu Arg Thr Gly Ala Tyr His Tyr Phe Lys Asn
            980                 985                 990

Leu Ile Asn Pro Ser Gly Ala Leu Asp Val Ser Gly Ser Gly Thr Thr
                995                 1000                1005

Asn Gly Thr Asn Ile Leu Tyr Trp Ser Tyr Asn Arg Ala Thr Asn
    1010                1015                1020

Gln Lys Phe Lys Leu Glu Glu Val Asn Ile Ser Gly Gly Gln Thr
    1025                1030                1035

Glu Gly Val Leu Leu Tyr Ala Glu Ala Asn Tyr Val Gly Lys Ser
    1040                1045                1050

Val Leu Leu Thr Asn Ser Val Ser Asn Leu Arg Asp Val Gly Met
    1055                1060                1065

Asn Asp Ile Ala Ser Ser Ile Lys Phe Ile Gly Pro Tyr Gln Ala
    1070                1075                1080

Thr Leu Tyr Glu His Asp Asp Phe Thr Gly Ala Val Phe Thr Pro
    1085                1090                1095

Thr Ser Asn Val Ala Asn Leu Lys Asp Val Gly Met Asn Asp Thr
    1100                1105                1110

Val Ser Ser Ile Lys Ile Thr Lys Thr Ser Gly Gly Arg Ala Thr
```

```
                1115                1120                1125
Gly Ile Tyr Leu Tyr Ala Asp Ala Asn Tyr Val Gly Arg Ser Val
            1130                1135                1140
Trp Leu Thr Ser Asn Val Ala Asn Leu Lys Asp Val Gly Met Asn
            1145                1150                1155
Asp Thr Val Ser Ser Val Glu Ile Val Gly Ala Tyr Gln Ala Thr
            1160                1165                1170
Leu Tyr Gly Asp Ser Asn Tyr Thr Gly Lys Ala Tyr Asn Leu Thr
            1175                1180                1185
His Asn Val Ala Asn Leu Lys Asp Val Gly Met Asn Asp Ile Val
            1190                1195                1200
Ser Ser Ile Lys Ile Phe Ser Val
            1205                1210
```

<210> SEQ ID NO 9
<211> LENGTH: 3642
<212> TYPE: DNA
<213> ORGANISM: Bacillus thuringiensis
<220> FEATURE:
<221> NAME/KEY: misc_feature
<222> LOCATION: (1)..(3642)
<223> OTHER INFORMATION: The native nucleotide sequence encoding TIC4006 toxin protein obtained from Bacillus thuringiensis species WC12466.

<400> SEQUENCE: 9

```
atgaatcaat atgttacaac agtgcaaaag gcagttaatg cattattttc aaataatacc      60
ttacccttaa acattactga ttataatata gaccagacag catatcttgt agaacgtata     120
tctaatgata gatattctaa agacaagatg atgttactca atcaagtcaa atttgcgaaa     180
cgtttgagtc gagcgcgtaa cttattgaaa ggtggcgctt ttgaattatc agataagaat     240
agatggaaga caaacaatta tgcgaatatt ttatcaggtt ctctcctatc caaaggccaa     300
tctttaaaca ttctaagcgc aagccctaca gtaagtagtc aaattattcc gactcatgta     360
tatcaaagaa tagatgaatc aaagttaaaa ccatatacac gttatttagt aagagggttc     420
gttgaaaaga gtcgagattt agaactattt gtgctcagat ataacaaaga ggtgtataaa     480
agaatcaatg tacccaagaa tgaggattat catatcacat cgcatttaaa tgaagaagag     540
aatccatggc acaataaata tatccaaaac actccggttc aaaattcaat ctctatgcgc     600
aagaattcac atgagtttac gtgtcatatt gatataggg aactggatat aaagaaagga     660
cctggtataa ccatcggttt tcaaattagc acaacagatg ggatggcaac attagataat     720
atagaagtga tagaagcaca tccgttaact ggagacgatt taacacgtat ccaaaggcgt     780
gaacgtaaat ggaaacaaaa atggctagag aatcaaatac aaatcgaaaa agctgcacaa     840
acagcgaaag aggcgattaa aaatttattt acatgcccac aacaaaatca attgacctgg     900
atgcaacccc taaacgacat tatacaggca gaaaaattga tacaagagat tccatattgg     960
tatagccgac ttttaggtga ggatttcccc atactaccag aagaggcata tgacacccct    1020
caacaacttt caactgcagt tgaaaccgca aaattgttgt atgcacaacg aaatgtggtg    1080
aataatgggg attttcaagc tggattttca aattggaata cgaccgatgg tgcagagata    1140
aaacaaattc aggattcatc ttctgttcta gtaattacgg actgggctgc aaatatttca    1200
caggacatgc gtgtggttga aaaaggtggc tatctgctgc gcgtaacagc gaaaaagaa    1260
gatgccggag aaggttatat aacaattagt gattgttccg tagtgatgga aaaattgaca    1320
tttacaacag gggattctgt agagagtctg gcacattctg atatttattc aaggatccat    1380
```

```
aagcgctatg ctaaaaaaca aataacaaat catctttcag aaagatatga aatagaatcg    1440
aatcctcatt taattaatag agcggaacaa aatgcttccc tcccttctag ctatgtaacc    1500
aaaacgattg aagtctttcc ggaaaccaat cgagtacgcg ttgaaattgg agaaacaggt    1560
ggaacattta tcgtggaaag tgtcgaattg attcgaatgg aacagatgaa cgaaacaaac    1620
aatccagctg tagatattca aactgtaatg aatgatacac ccgctacaca atttgatcca    1680
gtttctttta cagaatcaac ggtgagtccc agaaatactc aatatgcata ttctcatgat    1740
tcaaatatag gttatgaaaa tcctaactgg atggctgata tttcaggtga tactttattt    1800
agtgatttat ctatccctgg tacacataat acaatggctt tttatggagg agatattaca    1860
caatgtcaaa cgatgtcact gaatacgcaa ttacatgtag gaattcgtta tttagatatt    1920
cgctgtaggc atatcgaaaa tattttttgcg attcatcatg gaattgtgta ccaaaatgcg    1980
acgtttacag atgtttgtat agccgtaaga gattttttga ggaacaaccc tagtgagaca    2040
gtatttatgc ggataaaaga agaacataca gcagaaaata atacaagatc ttttggggag    2100
acatttgcag actataagtc tcaatatagc gacttatttt ggaattggac gggtgataac    2160
ccaagattaa gtgaaataag aggaaaagtt gttgttttgc aaaattttt tggggataaa    2220 tttggtatcg attacaatac actgaataaa caagatcaat atcatttaaa tacaaactgg    2280
gatttatatg ataaatggct atttgtaaaa gaacatttgt atgccgctga cgattcttat    2340
aaaaatggtc gtaaacaagc atatctaaat tatctaagcg ggtcaggtgg ttcttttcct    2400
tattttgttg caagtggaca cagtagtcct ggtacaaatg cttcaaatct atctacaggg    2460
ctaacaacac cggcatttga aagctggtat ccggattttc cacggggaag ttgttttata    2520
ggaatttgca caatttattt tgaaggaaca aatattctta caagtgagtg gatacagaaa    2580
agtgatttta aatatgtagg aatcatagct gctgattttc caggaagaac attaatttcc    2640
aatattatta gtctgaataa tcttcttagt ttagaaatta aaaatggtgg tacctatcaa    2700
attgtttccg ctttaaataa tagtagtgtt gtagatatga atccaggaga ccaaaatatt    2760
cacttatgga acaataacgg tactgctaat caattatgga aattcgtata taattcaaat    2820
gaattagcat accaaattaa aagtttatct aatgaaaatt tagtattaac ctgggcttac    2880
aatagtagta atccagataa tgtaattgct gcttccaatc aaaataggtc tgagcaatat    2940 tggataccctg agcgtacggg agcatatcat tatttttaaaa atctaagcaa tcgttcggga    3000
gcattagatg taagcggctc agagacaaaa aacggaacaa acattctgta ctggagttat    3060
aaaaaagcaa caaatcaaaa attcaaactg acagaagtaa atgtatctgg aggtcaagct    3120
gaaggtgtat atttatatgc agatgccaat tatgtagggc aatctgtagg gctaacaaat    3180
agtgtcgcag accttagcga agttggtatg aatgatatag ctagttctat aaaatttatt    3240
ggtccttatc aagctactct atatgagcat gctgatttta aaggtgcggt ttttactccc    3300
acaactaata ttgcaaattt aaaagatgtt ggcatgaatg atacaatcag ctctataaaa    3360
attacaaaga catctggagg ccgagctgca ggtatatatt tatattcgga tgccaattat    3420
gtgggaaggt ctatatggtt aacgtctaat gttgcaaatt taaaagatgt tggcatgaat    3480
gatacaatca gttccgtaga aattgttggc gcatatggag tcactttata tggggatgcc    3540
aattatacag gtaaggctta tgctctcaca tctaatgttg caaatttaaa agatgttggc    3600
atgaatgata tagtcagttc tataaaaaatt tttagtgtat aa                     3642
```

<210> SEQ ID NO 10

```
<211> LENGTH: 1213
<212> TYPE: PRT
<213> ORGANISM: Bacillus thuringiensis
<220> FEATURE:
<221> NAME/KEY: MISC_F -continued Phe Ser Asn Trp Asn Thr Thr Asp Gly Ala Glu Ile Lys Gln Ile Gln
    370                 375                 380

Asp Ser Ser Ser Val Leu Val Ile Thr Asp Trp Ala Ala Asn Ile Ser
385                 390                 395                 400

Gln Asp Met Arg Val Val Glu Lys Gly Gly Tyr Leu Leu Arg Val Thr
                405                 410                 415

Ala Lys Lys Glu Asp Ala Gly Glu Gly Tyr Ile Thr Ile Ser Asp Cys
            420                 425                 430

Ser Val Val Met Glu Lys Leu Thr Phe Thr Thr Gly Asp Ser Val Glu
                435                 440                 445

Ser Leu Ala His Ser Asp Ile Tyr Ser Arg Ile His Lys Arg Tyr Ala
    450                 455                 460

Lys Lys Gln Ile Thr Asn His Leu Ser Glu Arg Tyr Glu Ile Glu Ser
465                 470                 475                 480

Asn Pro His Leu Ile Asn Arg Ala Glu Gln Asn Ala Ser Leu Pro Ser
                485                 490                 495

Ser Tyr Val Thr Lys Thr Ile Glu Val Phe Pro Glu Thr Asn Arg Val
            500                 505                 510

Arg Val Glu Ile Gly Glu Thr Gly Gly Thr Phe Ile Val Glu Ser Val
                515                 520                 525

Glu Leu Ile Arg Met Glu Gln Met Asn Glu Thr Asn Asn Pro Ala Val
    530                 535                 540

Asp Ile Gln Thr Val Met Asn Asp Thr Pro Ala Thr Gln Phe Asp Pro
545                 550                 555                 560

Val Ser Phe Thr Glu Ser Thr Val Ser Pro Arg Asn Thr Gln Tyr Ala
                565                 570                 575

Tyr Ser His Asp Ser Asn Ile Gly Tyr Glu Asn Pro Asn Trp Met Ala
            580                 585                 590

Asp Ile Ser Gly Asp Thr Leu Phe Ser Asp Leu Ser Ile Pro Gly Thr
                595                 600                 605

His Asn Thr Met Ala Phe Tyr Gly Gly Asp Ile Thr Gln Cys Gln Thr
    610                 615                 620

Met Ser Leu Asn Thr Gln Leu His Val Gly Ile Arg Tyr Leu Asp Ile
625                 630                 635                 640

Arg Cys Arg His Ile Glu Asn Ile Phe Ala Ile His His Gly Ile Val
                645                 650                 655

Tyr Gln Asn Ala Thr Phe Thr Asp Val Cys Ile Ala Val Arg Asp Phe
            660                 665                 670

Leu Arg Asn Asn Pro Ser Glu Thr Val Phe Met Arg Ile Lys Glu Glu
                675                 680                 685

His Thr Ala Glu Asn Asn Thr Arg Ser Phe Gly Glu Thr Phe Ala Asp
    690                 695                 700

Tyr Lys Ser Gln Tyr Ser Asp Leu Phe Trp Asn Trp Thr Gly Asp Asn
705                 710                 715                 720

Pro Arg Leu Ser Glu Ile Arg Gly Lys Val Val Leu Gln Asn Phe
                725                 730                 735

Phe Gly Asp Lys Phe Gly Ile Asp Tyr Asn Thr Leu Asn Lys Gln Asp
            740                 745                 750

Gln Tyr His Leu Asn Thr Asn Trp Asp Leu Tyr Asp Lys Trp Leu Phe
                755                 760                 765

Val Lys Glu His Leu Tyr Ala Ala Asp Asp Ser Tyr Lys Asn Gly Arg
    770                 775                 780

Lys Gln Ala Tyr Leu Asn Tyr Leu Ser Gly Ser Gly Gly Ser Phe Pro

-continued

```
            785                 790                 795                 800
        Tyr Phe Val Ala Ser Gly His Ser Ser Pro Gly Thr Asn Ala Ser Asn
                        805                 810                 815
        Leu Ser Thr Gly Leu Thr Thr Pro Ala Phe Glu Ser Trp Tyr Pro Asp
                        820                 825                 830
        Phe Pro Arg Gly Ser Cys Phe Ile Gly Ile Cys Thr Ile Tyr Phe Glu
                        835                 840                 845
        Gly Thr Asn Ile Leu Thr Ser Glu Trp Ile Gln Lys Ser Asp Phe Lys
                        850                 855                 860
        Tyr Val Gly Ile Ile Ala Ala Asp Phe Pro Gly Arg Thr Leu Ile Ser
        865                 870                 875                 880
        Asn Ile Ile Ser Leu Asn Asn Leu Leu Ser Leu Glu Ile Lys Asn Gly
                        885                 890                 895
        Gly Thr Tyr Gln Ile Val Ser Ala Leu Asn Asn Ser Ser Val Val Asp
                        900                 905                 910
        Met Asn Pro Gly Asp Gln Asn Ile His Leu Trp Asn Asn Gly Thr
                        915                 920                 925
        Ala Asn Gln Leu Trp Lys Phe Val Tyr Asn Ser Asn Glu Leu Ala Tyr
        930                 935                 940
        Gln Ile Lys Ser Leu Ser Asn Glu Asn Leu Val Leu Thr Trp Ala Tyr
        945                 950                 955                 960
        Asn Ser Ser Asn Pro Asp Asn Val Ile Ala Ala Ser Asn Gln Asn Arg
                        965                 970                 975
        Ser Glu Gln Tyr Trp Ile Pro Glu Arg Thr Gly Ala Tyr His Tyr Phe
                        980                 985                 990
        Lys Asn Leu Ser Asn Arg Ser Gly Ala Leu Asp Val Ser Gly Ser Glu
                        995                 1000                1005
        Thr Lys Asn Gly Thr Asn Ile Leu Tyr Trp Ser Tyr Lys Lys Ala
                1010                1015                1020
        Thr Asn Gln Lys Phe Lys Leu Thr Glu Val Asn Val Ser Gly Gly
                1025                1030                1035
        Gln Ala Glu Gly Val Tyr Leu Tyr Ala Asp Ala Asn Tyr Val Gly
                1040                1045                1050
        Gln Ser Val Gly Leu Thr Asn Ser Val Ala Asp Leu Ser Glu Val
                1055                1060                1065
        Gly Met Asn Asp Ile Ala Ser Ser Ile Lys Phe Ile Gly Pro Tyr
                1070                1075                1080
        Gln Ala Thr Leu Tyr Glu His Ala Asp Phe Lys Gly Ala Val Phe
                1085                1090                1095
        Thr Pro Thr Thr Asn Ile Ala Asn Leu Lys Asp Val Gly Met Asn
                1100                1105                1110
        Asp Thr Ile Ser Ser Ile Lys Ile Thr Lys Thr Ser Gly Gly Arg
                1115                1120                1125
        Ala Ala Gly Ile Tyr Leu Tyr Ser Asp Ala Asn Tyr Val Gly Arg
                1130                1135                1140
        Ser Ile Trp Leu Thr Ser Asn Val Ala Asn Leu Lys Asp Val Gly
                1145                1150                1155
        Met Asn Asp Thr Ile Ser Ser Val Glu Ile Val Gly Ala Tyr Gly
                1160                1165                1170
        Val Thr Leu Tyr Gly Asp Ala Asn Tyr Thr Gly Lys Ala Tyr Ala
                1175                1180                1185
        Leu Thr Ser Asn Val Ala Asn Leu Lys Asp Val Gly Met Asn Asp
                1190                1195                1200
```

Ile Val Ser Ser Ile Lys Ile Phe Ser Val
1205 1210

<210> SEQ ID NO 11
<211> LENGTH: 3657
<212> TYPE: DNA
<213> ORGANISM: Artificial
<220> FEATURE:
<223> OTHER INFORMATION: A synthetic coding sequence encoding a TIC4747PL pesticidal protein designed for expression in a plant cell wherein an additional alanine codon is inserted immediately following the initiating methionine codon.

<400> SEQUENCE: 11
atggctgacc agaagatcat taagatgcgg gaggcggtga acgccctgtt ctccaacaat 60
catcttaaac tcaacataac ggactacaac atcgaccaaa cggcctacct ggttgacagc 120
atgagcgacg acgcctaccg ccaggagaag atgatgttcc tcgaccagat aaagtttgcg 180
aagcggttaa gccagaagcg caatctcctg aatcatggcg acttcgaggg tagcaattgg 240
acgggcaaga acggatggaa gcggaataac tacgtggtcg tggcctccga ccatcccatc 300
ttcaagggcc gctatctcca catccctggc gcgacaacgg ccatgtccgg agccatcatc 360
ccgacctatg tgtaccagtc cattgatgag agtaaactca agccatacac acgctacctt 420
gtgcgcgggt tcgttggcaa gagccaggac ttagcgctgc tggtgtctcg gtacacgaag 480
gaggtgtaca agaagatcaa cgtaccgaac gacaaggact acgacatgac ttctcacatc 540
aaccgggagg agaacctgtg gcataaccgc tacatcaagg acacttcggt tcagaactcc 600
atctccatgt gcaagaaccc gcatgagttc acctgccaca ttgacatcgg cgaactcgac 660
cggaagaagg gccctggcat tacaatcggc ttccagattg gcacgacaga cggcatggca 720
acactggaca acatcgaggt gatcgaggcc cacccgctca ccggttacgc gctggcacgg 780
atcgagaagc gcgagcgcaa gtggaagcag aagtggctgg agcaccgaat ccagatcgag 840
aaggctgtgc agaccgccca ggaagtcatc aggaacctct tcacctgtcc acagcagaac 900
cagcttaact ggatgaccac ccggaacgac atcgcccacg ccgagaccct catcaaggag 960
atttcctacc gatactccca actatcctgc ggtgacttcc cgatcttacc cgaggaggcg 1020
tacgacatac tccagcagct ttccacggcg gtcgagacgg cgaaggcact ctacacacaa 1080
cgtaacgtcg tcaacaatgg cgacttccag gcgggcttga gtaattggca cagaaccgac 1140
ggtgccgaga tacagcaaat ccagaacgca tcgtcggtgc tcatcatcac ggactgggcc 1200
gccaacatct ctcaagacat gagagtagtc gagaagggtt cttatctcct aagggtcacc 1260
gctaagaagg aggacgctgg cgaagggtac attaccataa gcgactgcgc cgccctcatt 1320
gagaccctta ccttcaccac gggcgaatcg gttgagtcct taactcattc cgacattcac 1380
tcccgtctcc acaagcgcta caacaagaaa cacattaaga accacccatc cgaggagtac 1440
gaaatagaga gcgacctcca cctctttaac cgtgcggagc agaatggctc gttgccatca 1500
tcctacgtca ctaagacgat ggaaatcttc ccggagacca acagggtgcg aattgaaatc 1560
ggcgagacgg gcggaacctt catcgtggag tctgtagaac tcatccgcat ggaacagatg 1620
aacgagacaa acaatcccga tgtggatgtt cagatcgtga tgaatgacac gccagcaacc 1680
cagtttgatc cggtgtcgtt taccgagagc accgtccggc cgcgcaatgc ccagtacgcc 1740
tactctcatg attccaacat cgggtacgag aaccctaatt ggatggccga catcagcggc 1800
gacactctgt tcactgactt gtccatccct ggtacgcata acactatggc tctttacggc 1860

```
ggcgacatta cccaatgtca gacaatgtcg ctgaacaccc agttgcacgt gggaatccgc    1920
tacctggaca tccgctgccg ccacatcgag aacgctttcg ccatccacca cggcccggtg    1980
taccagaacg ccatgttcgg cgatgtgtgc atagccgttc gcaactttct ccggagtaac    2040
ccgagtgaga ctgtgttcat gcgtatcaag gaggagcaca ctgctgagaa caacacaagg    2100
tctttctcag acacattcgc cgattacaag tcacagtaca gcgacctgtt ctgggactgg    2160
actggcgaca tccgaggct cagcgagatc agaggcaaag tagtggtgct ccagaacttc    2220
tctggcggga aattcgggat aaactacaac accctcaaca cacaggatca gtaccaccta    2280
aataccaatt gggatctcta cgataaatgg ctgttcgtca aggagcatct gtacgctgct    2340
gacaacagct acaagtccgg taggaagcaa gtgtacttaa attacctgtc gggatctggc    2400
ggttccttcc cgtactttgt ggcgtcaggc cattcaagtc cggcactga cgcgccgcaa    2460 ctttctactg gccttaccac gcccgccttc gcctcgtggt atcctgactt cccacgcggt    2520
agctgcttca tcggcatctg cactatctac ttcgagggca ccaacattct gacaagccag    2580
tggatcgaga agaatgactt caagtacatt gggatcatcg cggccgactt ccgggtcgc    2640 accctcatct caaacattat ttccctgaac aaactcctgt ccctggagat taagaacggc    2700
ggcacttatc agatagtatc cgcgctcaat aacagctcgg tcattgacat gagccttcg    2760 ggcgaccgga acgtgcacct gtggtcgaat aacggcacac tgaaccaggt gtggaagttc    2820
gtctatgact caaaccggct ggcataccag atcaagagtc tttctgacga gaatttggtc    2880
ctcacctggg cctattactc ctccaacaga gacaacgtca tagtggccag caaccagaac    2940
tcggacgagc agtattggat ccagagcgt actggagctt accattactt taagaaccctc   3000 atcaacccga gtggcgcgct cgacgtcagt ggttccggca ccactaacgg gaccaacata    3060
ctctactggt cgtacaacag ggcgaccaac cagaaattca gctagagga ggtgaacatc    3120 cctggcggac aggcggaagg agttctgctg tacgccgatg ccaactatgt gggcaagtca    3180
gtcctcttga cgaactcagt atccaacctc cgcgacgtcg gcatgaacga catcgcaagt    3240
tccatcaaat tcatcgggcc gtaccaggcg accctctacg agcatgataa cttaccggc    3300 gcggctttca ccctgacatc gaatgtggcg aatctcaaag acgtcggtat gaacgacacg    3360
gtttcctcca tcaagatcac caagaccagt ggcgggcgcg ccacgggcat ctatctgtac    3420
gcggacgcca actacgtcgg gaggagcgtg tggctcacta gcaacgtggc caacctcaag    3480
gacatcggaa tgaacgatac cgtgtcctcc gtcgagatcg tgggtgcgta tcaggcgacc    3540
ctctacggcg acgcaaatta cacgggcaag gcgtacaacc tcacgcacaa tgtcacgaac    3600
ctgaaagacg tgggcatgaa cgacatcgtc tccagtatca agatcttcag cgtgtga     3657
```

<210> SEQ ID NO 12
<211> LENGTH: 1218
<212> TYPE: PRT
<213> ORGANISM: Artificial
<220> FEATURE:
<223> OTHER INFORMATION: The amino acid sequence of TIC4747PL encoded by a synthetic coding sequence designed for expression in a plant cell, and wherein an additional alanine amino acid is inserted immediately following the initiating methionine.

<400> SEQUENCE: 12

```
Met Ala Asp Gln Lys Ile Ile Lys Met Arg Glu Ala Val Asn Ala Leu
1               5                   10                  15

Phe Ser Asn Asn His Leu Lys Leu Asn Ile Thr Asp Tyr Asn Ile Asp
            20                  25                  30
```

Gln Thr Ala Tyr Leu Val Asp Ser Met Ser Asp Ala Tyr Arg Gln
                35                  40                  45

Glu Lys Met Met Phe Leu Asp Gln Ile Lys Phe Ala Lys Arg Leu Ser
 50                  55                  60

Gln Lys Arg Asn Leu Leu Asn His Gly Asp Phe Glu Gly Ser Asn Trp
 65                  70                  75                  80

Thr Gly Lys Asn Gly Trp Lys Arg Asn Asn Tyr Val Val Ala Ser
                 85                  90                  95

Asp His Pro Ile Phe Lys Gly Arg Tyr Leu His Ile Pro Gly Ala Thr
                100                 105                 110

Thr Ala Met Ser Gly Ala Ile Ile Pro Thr Tyr Val Tyr Gln Ser Ile
                115                 120                 125

Asp Glu Ser Lys Leu Lys Pro Tyr Thr Arg Tyr Leu Val Arg Gly Phe
130                 135                 140

Val Gly Lys Ser Gln Asp Leu Ala Leu Leu Val Ser Arg Tyr Thr Lys
145                 150                 155                 160

Glu Val Tyr Lys Lys Ile Asn Val Pro Asn Asp Lys Asp Tyr Asp Met
                165                 170                 175

Thr Ser His Ile Asn Arg Glu Glu Asn Leu Trp His Asn Arg Tyr Ile
                180                 185                 190

Lys Asp Thr Ser Val Gln Asn Ser Ile Ser Met Cys Lys Asn Pro His
                195                 200                 205

Glu Phe Thr Cys His Ile Asp Ile Gly Glu Leu Asp Arg Lys Lys Gly
210                 215                 220

Pro Gly Ile Thr Ile Gly Phe Gln Ile Gly Thr Thr Asp Gly Met Ala
225                 230                 235                 240

Thr Leu Asp Asn Ile Glu Val Ile Glu Ala His Pro Leu Thr Gly Tyr
                245                 250                 255

Ala Leu Ala Arg Ile Glu Lys Arg Glu Arg Lys Trp Lys Gln Lys Trp
                260                 265                 270

Leu Glu His Arg Ile Gln Ile Glu Lys Ala Val Gln Thr Ala Gln Glu
                275                 280                 285

Val Ile Arg Asn Leu Phe Thr Cys Pro Gln Gln Asn Gln Leu Asn Trp
290                 295                 300

Met Thr Thr Arg Asn Asp Ile Ala His Ala Glu Thr Leu Ile Lys Glu
305                 310                 315                 320

Ile Ser Tyr Arg Tyr Ser Gln Leu Ser Cys Gly Asp Phe Pro Ile Leu
                325                 330                 335

Pro Glu Glu Ala Tyr Asp Ile Leu Gln Gln Leu Ser Thr Ala Val Glu
                340                 345                 350

Thr Ala Lys Ala Leu Tyr Thr Gln Arg Asn Val Val Asn Asn Gly Asp
                355                 360                 365

Phe Gln Ala Gly Leu Ser Asn Trp His Arg Thr Asp Gly Ala Glu Ile
370                 375                 380

Gln Gln Ile Gln Asn Ala Ser Ser Val Leu Ile Ile Thr Asp Trp Ala
385                 390                 395                 400

Ala Asn Ile Ser Gln Asp Met Arg Val Val Glu Lys Gly Ser Tyr Leu
                405                 410                 415

Leu Arg Val Thr Ala Lys Lys Glu Asp Ala Gly Glu Gly Tyr Ile Thr
                420                 425                 430

Ile Ser Asp Cys Ala Ala Leu Ile Glu Thr Leu Thr Phe Thr Thr Gly
                435                 440                 445

Glu Ser Val Glu Ser Leu Thr His Ser Asp Ile His Ser Arg Leu His

```
              450                 455                 460
Lys Arg Tyr Asn Lys Lys His Ile Lys Asn His Pro Ser Glu Glu Tyr
465                 470                 475                 480

Glu Ile Glu Ser Asp Leu His Leu Phe Asn Arg Ala Glu Gln Asn Gly
                    485                 490                 495

Ser Leu Pro Ser Ser Tyr Val Thr Lys Thr Met Glu Ile Phe Pro Glu
                500                 505                 510

Thr Asn Arg Val Arg Ile Glu Ile Gly Glu Thr Gly Gly Thr Phe Ile
                515                 520                 525

Val Glu Ser Val Glu Leu Ile Arg Met Glu Gln Met Asn Glu Thr Asn
            530                 535                 540

Asn Pro Asp Val Asp Val Gln Ile Val Met Asn Asp Thr Pro Ala Thr
545                 550                 555                 560

Gln Phe Asp Pro Val Ser Phe Thr Glu Ser Thr Val Arg Pro Arg Asn
                565                 570                 575

Ala Gln Tyr Ala Tyr Ser His Asp Ser Asn Ile Gly Tyr Glu Asn Pro
                580                 585                 590

Asn Trp Met Ala Asp Ile Ser Gly Asp Thr Leu Phe Thr Asp Leu Ser
            595                 600                 605

Ile Pro Gly Thr His Asn Thr Met Ala Leu Tyr Gly Gly Asp Ile Thr
            610                 615                 620

Gln Cys Gln Thr Met Ser Leu Asn Thr Gln Leu His Val Gly Ile Arg
625                 630                 635                 640

Tyr Leu Asp Ile Arg Cys Arg His Ile Glu Asn Ala Phe Ala Ile His
                645                 650                 655

His Gly Pro Val Tyr Gln Asn Ala Met Phe Gly Asp Val Cys Ile Ala
                660                 665                 670

Val Arg Asn Phe Leu Arg Ser Asn Pro Ser Glu Thr Val Phe Met Arg
            675                 680                 685

Ile Lys Glu Glu His Thr Ala Glu Asn Asn Thr Arg Ser Phe Ser Asp
            690                 695                 700

Thr Phe Ala Asp Tyr Lys Ser Gln Tyr Ser Asp Leu Phe Trp Asp Trp
705                 710                 715                 720

Thr Gly Asp Asn Pro Arg Leu Ser Glu Ile Arg Gly Lys Val Val Val
                725                 730                 735

Leu Gln Asn Phe Ser Gly Gly Lys Phe Gly Ile Asn Tyr Asn Thr Leu
                740                 745                 750

Asn Thr Gln Asp Gln Tyr His Leu Asn Thr Asn Trp Asp Leu Tyr Asp
            755                 760                 765

Lys Trp Leu Phe Val Lys Glu His Leu Tyr Ala Ala Asp Asn Ser Tyr
770                 775                 780

Lys Ser Gly Arg Lys Gln Val Tyr Leu Asn Tyr Leu Ser Gly Ser Gly
785                 790                 795                 800

Gly Ser Phe Pro Tyr Phe Val Ala Ser Gly His Ser Ser Pro Gly Thr
                805                 810                 815

Asp Ala Pro Gln Leu Ser Thr Gly Leu Thr Thr Pro Ala Phe Ala Ser
                820                 825                 830

Trp Tyr Pro Asp Phe Pro Arg Gly Ser Cys Phe Ile Gly Ile Cys Thr
            835                 840                 845

Ile Tyr Phe Glu Gly Thr Asn Ile Leu Thr Ser Gln Trp Ile Glu Lys
            850                 855                 860

Asn Asp Phe Lys Tyr Ile Gly Ile Ile Ala Ala Asp Phe Pro Gly Arg
865                 870                 875                 880
```

Thr Leu Ile Ser Asn Ile Ile Ser Leu Asn Lys Leu Leu Ser Leu Glu
                885                 890                 895

Ile Lys Asn Gly Gly Thr Tyr Gln Ile Val Ser Ala Leu Asn Asn Ser
            900                 905                 910

Ser Val Ile Asp Met Ser Leu Ser Gly Asp Arg Asn Val His Leu Trp
        915                 920                 925

Ser Asn Asn Gly Thr Leu Asn Gln Val Trp Lys Phe Val Tyr Asp Ser
    930                 935                 940

Asn Arg Leu Ala Tyr Gln Ile Lys Ser Leu Ser Asp Glu Asn Leu Val
945                 950                 955                 960

Leu Thr Trp Ala Tyr Tyr Ser Ser Asn Arg Asp Asn Val Ile Val Ala
                965                 970                 975

Ser Asn Gln Asn Ser Asp Glu Gln Tyr Trp Ile Pro Glu Arg Thr Gly
            980                 985                 990

Ala Tyr His Tyr Phe Lys Asn Leu Ile Asn Pro Ser Gly Ala Leu Asp
        995                 1000                1005

Val Ser Gly Ser Gly Thr Thr Asn Gly Thr Asn Ile Leu Tyr Trp
    1010                1015                1020

Ser Tyr Asn Arg Ala Thr Asn Gln Lys Phe Lys Leu Glu Glu Val
    1025                1030                1035

Asn Ile Pro Gly Gly Gln Ala Glu Gly Val Leu Leu Tyr Ala Asp
    1040                1045                1050

Ala Asn Tyr Val Gly Lys Ser Val Leu Leu Thr Asn Ser Val Ser
    1055                1060                1065

Asn Leu Arg Asp Val Gly Met Asn Asp Ile Ala Ser Ser Ile Lys
    1070                1075                1080

Phe Ile Gly Pro Tyr Gln Ala Thr Leu Tyr Glu His Asp Asn Phe
    1085                1090                1095

Thr Gly Ala Ala Phe Thr Leu Thr Ser Asn Val Ala Asn Leu Lys
    1100                1105                1110

Asp Val Gly Met Asn Asp Thr Val Ser Ser Ile Lys Ile Thr Lys
    1115                1120                1125

Thr Ser Gly Gly Arg Ala Thr Gly Ile Tyr Leu Tyr Ala Asp Ala
    1130                1135                1140

Asn Tyr Val Gly Arg Ser Val Trp Leu Thr Ser Asn Val Ala Asn
    1145                1150                1155

Leu Lys Asp Ile Gly Met Asn Asp Thr Val Ser Ser Val Glu Ile
    1160                1165                1170

Val Gly Ala Tyr Gln Ala Thr Leu Tyr Gly Asp Ala Asn Tyr Thr
    1175                1180                1185

Gly Lys Ala Tyr Asn Leu Thr His Asn Val Thr Asn Leu Lys Asp
    1190                1195                1200

Val Gly Met Asn Asp Ile Val Ser Ser Ile Lys Ile Phe Ser Val
    1205                1210                1215

<210> SEQ ID NO 13
<211> LENGTH: 3657
<212> TYPE: DNA
<213> ORGANISM: Artificial
<220> FEATURE:
<223> OTHER INFORMATION: A synthetic coding sequence encoding a
      TIC7181PL pesticidal protein designed for expression in a plant cell wherein an additional alanine codon is inserted immediately following the initiating methionine codon.

<400> SEQUENCE: 13

```
atggctgacc agaagattat caagatgcgt gaggcagtga atcgctgtt cagcaacaac      60
catctcaagc tgaacatcac cgactacaac atcgaccaga ccgcgtacct agtggacagc    120
atgtccgacg acgcctaccg tcaggagaag atgatgttcc tggatcagat caagtttgca    180
aagcgcctgt cccagaagcg caacctgctg aaccacggcg acttcgaggg ttcgaactgg    240
acgggcaaga acggctggaa gcggaacaac tacgtggtgg tggcgtccga ccacccgatc    300
ttcaaaggcc gctacctcca catccctggc gcgaccacgg ccatgtcggg tgcaattatc    360
cctacctatg tgtaccagag cattgatgag agtaagctca agccctacac acgctacctt    420
gtgcgcggtt tcgttggaaa gagccaggat ctcgccctgc tcgtgagcag atacacgaaa    480
gaggtgtaca agaagatcaa cgtgccgaac gacaaggact atgacatgac ctcccacatc    540
aaccgcgagg agaacctctg gcacaatcgc tacatcaagg cacctcggtt ccagaacagc    600
atctccatgt gcaagaaccc gcacgagttc acctgccaca ttgacattgg tgagctcgac    660
cgcaagaagg gtccgggcat taccattggt ttccagattg ggactactga cggcatggca    720
acgctcgata acatcgaagt tatcgaagcc atcctctta ctggatacgc ccttgctcgc    780
atcgagaagc gtgaacgcaa gtggaagcag aaatggctcg agcaccggat acagattgag    840
aaggctgttc aaacagcaca ggaggtgatt cggaacctgt tcacctgtcc gcagcagaac    900
cagctgaact ggatgacaac tcggaacgat atcgctcacg ctgagaccct gatcaaggaa    960
atctcttacc ggtactctca gctgtcgtgc ggcgactttc ccatactccc ggaggaggcg   1020
tatgacatct tgcagcaact ttcgactgcc gtcgagactg caaaggccct ctacactcag   1080
cggaacgtcg tgaacaacgg cgacttccag gctggcttat cgaactggca ccgcactgac   1140
ggagctgaga tccagcagat ccagaacgca tcatctgtcc tgataataac tgactgggcg   1200
gcgaacatct cccaagacat gcgggtggtt gagaagggca gctatctcct gagggtcaca   1260
gccaagaagg aggacgccgg tgaaggctac atcaccatct tgactgcgc ggcactgatc   1320
gagaccctca ctttcactac aggcgaaagc gtggagtcct taacgcactc agacattcac   1380
agtaggctac acaaacgcta caacaagaag cacatcaaga atcacccatc cgaggagtac   1440
gagattgagt ccgacctcca cctgtttaac cgcgcggagc agaacggttc ccttccctcg   1500
agctacgtga ccaagacgat ggagatcttc ccggagacca accggatccg cattgaaatc   1560
ggagagacgg gcgaacgtt catagtcgag agcgtcgaat tgatccggat ggagcagatg   1620
aacgagacca caacccgga tgtcgacgtc caaatcgtga tgaacgacac gcccgcaacc   1680
cagtttgacc cggtcagctt caccgagagc actgttcgcc cgcgcaatgc ccagtacgcc   1740
tacagccacg atagtaacat tggctacgag aacccgaact ggatggccga cattagcgga   1800
gacacctgt tcacggacct ctcgatccct gggactcata acacaatggc actttacggt   1860
ggcgatatca ctcagtgcca gacaatgagc ctcaacactc agctccacgt gggcattcgg   1920
tatttggaca ttcgttgtcg ccacattgag aacgccttcg cgatccatca cgggcctgtg   1980
taccagaacg ccatgttcgg cgacgtctgc atagcagtgc gcaactttct taggtcaaac   2040
ccatccgaga ctgtgttcat gcgtatcaag gaggagcaca cggctgagaa taacacccgt   2100
tccttctctg atacgttcgc cgattacaaa tcccaatact ccgacctctt ctgggattgg   2160
accggtgaca acccaagact ctccgagatt cgcggcaaag ttgttgtctt acagaatttc   2220
tccgcggca aattcgggat aaactacaac cccctcaaca cccaggacca gtatcatctg   2280
aacacaaatt gggacttgta cgacaagtgg ctgttcgtca aggaacacct ctacgccgct   2340
```

```
gacaattcgt acaaatccgg tcgcaaacaa gtttatctga actacctgtc cggctcgggc    2400
ggttcctttc cttacttcgt cgctagcggg cacagcagtc ctgggactga tgcgccgcaa    2460
ctatcgaccg gtctcacaac gccagcgttc gccagctggt atccggattt ccgcgcggc    2520 tcctgcttca tcgggatctg caccatctat ttcgagggca cgaacatcct gacaagccaa    2580
tggatcgaga agaacgactt caagtacatt ggaatcatag cggccgactt ccctggacgt    2640
accctcatct cgaacatcat ctcccttaac aagcttctgt cactggagat caagaatggc    2700
ggcacctacc aaatcgttag cgcgcttaat aacagcagcg tgatcgacat gtccctcagc    2760
ggcgacagaa cgttcatct gtggtccaac aacggaacac tcaatcaagt gtggaaattc    2820
gtgtacgaca gcaaccgact ggcataccag atcaagtccc tgtcagacga aatctcgtg    2880 ctcacgtggg cttattacag ctccaaccgt gataacgtca tcgtggctag taaccagaac    2940
tccgacgagc aatactggat tccagaacga acgggcgcat accactactt caagaatctg    3000
atcaacccat ccggagccct tgacgtgagt ggcagcggta cgacgaacgg aacgaacatc    3060
ctctactggt cttacaatcg ggccaccaac cagaagttca agctcgagga ggtgaacatt    3120
ccgggaggtc aggccgaggg cgtgctactg tacgccgacg caaactacgt cggcaagtcc    3180
gtcctactga ccaactccgt gagcaacctg agggacgtcg gtatgaacga cattgcgtcc    3240
agcatcaagt tcattgggcc ctaccaggcc acactgtacg agcacgacaa tttcaccggc    3300
gcggcgttca ctctcacctc aaacgtggcc aacttgaaag acgtgggcat gaacgacacg    3360
gtgtcctcca ttaagataac gaagacctct ggtggtcgcg ctacgggcat ctacctctac    3420
gccgacgcga actacgtcgg tcggtcggtg tggctcacat ccaacgtggc taaccctcaag    3480 gacattggaa tgaacgacac ggtctccagc gtagagatcg taggcgccta ccaagccacc    3540
ctctacggcg atgcaaacta cactggcaag gcgtacaacc taacccacaa cgtgacgaac    3600
ctcaaggacg ttggtatgaa cgacattgtg tccagtatta agatcttcag cgtctga       3657
```

<210> SEQ ID NO 14
<211> LENGTH: 1218
<212> TYPE: PRT
<213> ORGANISM: Artificial
<220> FEATURE:
<223> OTHER INFORMATION: The amino acid sequence of TIC7181PL encoded by a synthetic coding sequence designed for expression in a plant cell, and wherein an additional alanine amino acid is inserted immediately following the initiating methionine.

<400> SEQUENCE: 14

```
Met Ala Asp Gln Lys Ile Ile Lys Met Arg Glu Ala Val Asn Ala Leu
1               5                   10                  15

Phe Ser Asn Asn His Leu Lys Leu Asn Ile Thr Asp Tyr Asn Ile Asp
                20                  25                  30

Gln Thr Ala Tyr Leu Val Asp Ser Met Ser Asp Asp Ala Tyr Arg Gln
            35                  40                  45

Glu Lys Met Met Phe Leu Asp Gln Ile Lys Phe Ala Lys Arg Leu Ser
        50                  55                  60

Gln Lys Arg Asn Leu Leu Asn His Gly Asp Phe Glu Gly Ser Asn Trp
65                  70                  75                  80

Thr Gly Lys Asn Gly Trp Lys Arg Asn Asn Tyr Val Val Val Ala Ser
                85                  90                  95

Asp His Pro Ile Phe Lys Gly Arg Tyr Leu His Ile Pro Gly Ala Thr
            100                 105                 110

Thr Ala Met Ser Gly Ala Ile Ile Pro Thr Tyr Val Tyr Gln Ser Ile
```

```
            115                 120                 125
Asp Glu Ser Lys Leu Lys Pro Tyr Thr Arg Tyr Leu Val Arg Gly Phe
            130                 135                 140

Val Gly Lys Ser Gln Asp Leu Ala Leu Leu Val Ser Arg Tyr Thr Lys
145                 150                 155                 160

Glu Val Tyr Lys Lys Ile Asn Val Pro Asn Asp Lys Asp Tyr Asp Met
                165                 170                 175

Thr Ser His Ile Asn Arg Glu Glu Asn Leu Trp His Asn Arg Tyr Ile
            180                 185                 190

Lys Asp Thr Ser Val Gln Asn Ser Ile Ser Met Cys Lys Asn Pro His
            195                 200                 205

Glu Phe Thr Cys His Ile Asp Ile Gly Glu Leu Asp Arg Lys Lys Gly
            210                 215                 220

Pro Gly Ile Thr Ile Gly Phe Gln Ile Gly Thr Thr Asp Gly Met Ala
225                 230                 235                 240

Thr Leu Asp Asn Ile Glu Val Ile Glu Ala His Pro Leu Thr Gly Tyr
                245                 250                 255

Ala Leu Ala Arg Ile Glu Lys Arg Glu Arg Lys Trp Lys Gln Lys Trp
            260                 265                 270

Leu Glu His Arg Ile Gln Ile Glu Lys Ala Val Gln Thr Ala Gln Glu
            275                 280                 285

Val Ile Arg Asn Leu Phe Thr Cys Pro Gln Gln Asn Gln Leu Asn Trp
290                 295                 300

Met Thr Thr Arg Asn Asp Ile Ala His Ala Glu Thr Leu Ile Lys Glu
305                 310                 315                 320

Ile Ser Tyr Arg Tyr Ser Gln Leu Ser Cys Gly Asp Phe Pro Ile Leu
                325                 330                 335

Pro Glu Glu Ala Tyr Asp Ile Leu Gln Gln Leu Ser Thr Ala Val Glu
            340                 345                 350

Thr Ala Lys Ala Leu Tyr Thr Gln Arg Asn Val Val Asn Asn Gly Asp
            355                 360                 365

Phe Gln Ala Gly Leu Ser Asn Trp His Arg Thr Asp Gly Ala Glu Ile
            370                 375                 380

Gln Gln Ile Gln Asn Ala Ser Ser Val Leu Ile Ile Thr Asp Trp Ala
385                 390                 395                 400

Ala Asn Ile Ser Gln Asp Met Arg Val Val Glu Lys Gly Ser Tyr Leu
                405                 410                 415

Leu Arg Val Thr Ala Lys Lys Glu Asp Ala Gly Glu Gly Tyr Ile Thr
            420                 425                 430

Ile Ser Asp Cys Ala Ala Leu Ile Glu Thr Leu Thr Phe Thr Thr Gly
            435                 440                 445

Glu Ser Val Glu Ser Leu Thr His Ser Asp Ile His Ser Arg Leu His
            450                 455                 460

Lys Arg Tyr Asn Lys Lys His Ile Lys Asn His Pro Ser Glu Glu Tyr
465                 470                 475                 480

Glu Ile Glu Ser Asp Leu His Leu Phe Asn Arg Ala Glu Gln Asn Gly
                485                 490                 495

Ser Leu Pro Ser Ser Tyr Val Thr Lys Thr Met Glu Ile Phe Pro Glu
            500                 505                 510

Thr Asn Arg Ile Arg Ile Glu Ile Gly Glu Thr Gly Gly Thr Phe Ile
            515                 520                 525

Val Glu Ser Val Glu Leu Ile Arg Met Glu Gln Met Asn Glu Thr Asn
            530                 535                 540
```

```
Asn Pro Asp Val Asp Val Gln Ile Val Met Asn Asp Thr Pro Ala Thr
545                 550                 555                 560

Gln Phe Asp Pro Val Ser Phe Thr Glu Ser Thr Val Arg Pro Arg Asn
                565                 570                 575

Ala Gln Tyr Ala Tyr Ser His Asp Ser Asn Ile Gly Tyr Glu Asn Pro
            580                 585                 590

Asn Trp Met Ala Asp Ile Ser Gly Asp Thr Leu Phe Thr Asp Leu Ser
        595                 600                 605

Ile Pro Gly Thr His Asn Thr Met Ala Leu Tyr Gly Gly Asp Ile Thr
    610                 615                 620

Gln Cys Gln Thr Met Ser Leu Asn Thr Gln Leu His Val Gly Ile Arg
625                 630                 635                 640

Tyr Leu Asp Ile Arg Cys Arg His Ile Glu Asn Ala Phe Ala Ile His
                645                 650                 655

His Gly Pro Val Tyr Gln Asn Ala Met Phe Gly Asp Val Cys Ile Ala
            660                 665                 670

Val Arg Asn Phe Leu Arg Ser Asn Pro Ser Glu Thr Val Phe Met Arg
        675                 680                 685

Ile Lys Glu Glu His Thr Ala Glu Asn Asn Thr Arg Ser Phe Ser Asp
    690                 695                 700

Thr Phe Ala Asp Tyr Lys Ser Gln Tyr Ser Asp Leu Phe Trp Asp Trp
705                 710                 715                 720

Thr Gly Asp Asn Pro Arg Leu Ser Glu Ile Arg Gly Lys Val Val Val
                725                 730                 735

Leu Gln Asn Phe Ser Gly Gly Lys Phe Gly Ile Asn Tyr Asn Thr Leu
            740                 745                 750

Asn Thr Gln Asp Gln Tyr His Leu Asn Thr Asn Trp Asp Leu Tyr Asp
        755                 760                 765

Lys Trp Leu Phe Val Lys Glu His Leu Tyr Ala Ala Asp Asn Ser Tyr
    770                 775                 780

Lys Ser Gly Arg Lys Gln Val Tyr Leu Asn Tyr Leu Ser Gly Ser Gly
785                 790                 795                 800

Gly Ser Phe Pro Tyr Phe Val Ala Ser Gly His Ser Ser Pro Gly Thr
                805                 810                 815

Asp Ala Pro Gln Leu Ser Thr Gly Leu Thr Thr Pro Ala Phe Ala Ser
            820                 825                 830

Trp Tyr Pro Asp Phe Pro Arg Gly Ser Cys Phe Ile Gly Ile Cys Thr
        835                 840                 845

Ile Tyr Phe Glu Gly Thr Asn Ile Leu Thr Ser Gln Trp Ile Glu Lys
    850                 855                 860

Asn Asp Phe Lys Tyr Ile Gly Ile Ile Ala Ala Asp Phe Pro Gly Arg
865                 870                 875                 880

Thr Leu Ile Ser Asn Ile Ile Ser Leu Asn Lys Leu Leu Ser Leu Glu
                885                 890                 895

Ile Lys Asn Gly Gly Thr Tyr Gln Ile Val Ser Ala Leu Asn Asn Ser
            900                 905                 910

Ser Val Ile Asp Met Ser Leu Ser Gly Asp Arg Asn Val His Leu Trp
        915                 920                 925

Ser Asn Asn Gly Thr Leu Asn Gln Val Trp Lys Phe Val Tyr Asp Ser
    930                 935                 940

Asn Arg Leu Ala Tyr Gln Ile Lys Ser Leu Ser Asp Glu Asn Leu Val
945                 950                 955                 960
```

```
Leu Thr Trp Ala Tyr Tyr Ser Ser Asn Arg Asp Asn Val Ile Val Ala
                965                 970                 975

Ser Asn Gln Asn Ser Asp Glu Gln Tyr Trp Ile Pro Glu Arg Thr Gly
        980                 985                 990

Ala Tyr His Tyr Phe Lys Asn Leu  Ile Asn Pro Ser Gly  Ala Leu Asp
        995                 1000                1005

Val Ser  Gly Ser Gly Thr Thr  Asn Gly Thr Asn Ile  Leu Tyr Trp
    1010                1015                1020

Ser Tyr  Asn Arg Ala Thr Asn  Gln Lys Phe Lys Leu  Glu Glu Val
    1025                1030                1035

Asn Ile  Pro Gly Gly Gln Ala  Glu Gly Val Leu Leu  Tyr Ala Asp
    1040                1045                1050

Ala Asn  Tyr Val Gly Lys Ser  Val Leu Leu Thr Asn  Ser Val Ser
    1055                1060                1065

Asn Leu  Arg Asp Val Gly Met  Asn Asp Ile Ala Ser  Ser Ile Lys
    1070                1075                1080

Phe Ile  Gly Pro Tyr Gln Ala  Thr Leu Tyr Glu His  Asp Asn Phe
    1085                1090                1095

Thr Gly  Ala Ala Phe Thr Leu  Thr Ser Asn Val Ala  Asn Leu Lys
    1100                1105                1110

Asp Val  Gly Met Asn Asp Thr  Val Ser Ser Ile Lys  Ile Thr Lys
    1115                1120                1125

Thr Ser  Gly Gly Arg Ala Thr  Gly Ile Tyr Leu Tyr  Ala Asp Ala
    1130                1135                1140

Asn Tyr  Val Gly Arg Ser Val  Trp Leu Thr Ser Asn  Val Ala Asn
    1145                1150                1155

Leu Lys  Asp Ile Gly Met Asn  Asp Thr Val Ser Ser  Val Glu Ile
    1160                1165                1170

Val Gly  Ala Tyr Gln Ala Thr  Leu Tyr Gly Asp Ala  Asn Tyr Thr
    1175                1180                1185

Gly Lys  Ala Tyr Asn Leu Thr  His Asn Val Thr Asn  Leu Lys Asp
    1190                1195                1200

Val Gly  Met Asn Asp Ile Val  Ser Ser Ile Lys Ile  Phe Ser Val
    1205                1210                1215

<210> SEQ ID NO 15
<211> LENGTH: 3657
<212> TYPE: DNA
<213> ORGANISM: Artificial
<220> FEATURE:
<223> OTHER INFORMATION: A synthetic coding sequence encoding a
      TIC4904PL pesticidal protein designed for expression in a plant
      cell wherein an additional alanine codon is inserted immediately
      following the initiating methionine codon.

<400> SEQUENCE: 15
atggctgacc agaagatcat taagatgcgc gaggcggtca acgccctctt ctcaaacaat      60
cagctgaaac tgaacattac cgactacaac atcgaccaga ttgcctacct ggtggattca     120
atgtcggacg acgcctaccg ccaggagaag atgcggttcc tggaccagat caagttcgcc     180
aaacgcctgt cccagaagcg gaacttgctg aactacggcg acttcgaagg cagcaactgg     240
cccggcaaga tggctggaa gcaacaat tatgtggtcg tggcctccga tcacccgatc        300
ttcaagggcc gctatctcca catcccgtcg gccacaacta ccatgagcgg cgccatcatt     360
cccacgtact tttaccaacg cattgatgag tctaagctaa agccgtacac tcgctacttg     420
gtccgaggct acgttggcaa gagtcaggat cttgccctcc tggtttcacg atacaccaag     480
```

```
gaggtgtaca agaagatcaa tgtcccgaac gacgaggact acgacatcac ttcccacatc    540
aaccgggagg agaacctctg gcacaaccgc tacattcgcg gcacgcaagt gcagaactct    600
atttcaatgt gcaacaatcc tcatgagttt acctgccaca ttgacatcgg cgagctggac    660
aggaagaagg gccctgggat cacgataggc ttccagattg gcaccacgga cgggatggca    720
acccttgaca acatcgaggt gatcgaagcg caccctctga ccgggagcgc gctggcgaga    780
atcgagaaac gggagcgcaa gtggaagcag aagtggctcg agaaccagat acaaatcgag    840
aaggcggtcc agacagtcca ggaagtcatc cgtaacctct ttacctgccc gcagcagaac    900
cagttgaatt ggatgaccac aagaaatgac atcgcgcacg cggagaccct gatcaaggag    960
attccctacc gctacagcca actctcctgc ggcgacttcc cgatcctccc ggaggaggcg   1020
tacgacattc tccagcagct cagcactgca gtcgagaccg cgaagactct gtacacccag   1080
aggaacgtgg tcaagaacgg cgacttccaa gcgggtcttt ccaactggca tcgaaccgac   1140
ggagcagaga tacagcaaat ccagaacact agcagcgtcc ttgtcatcac ggactgggcc   1200
gccaacatca gccaggacat gcgcgttgtc gagaagggcg gatacctgct gcgcgtaaca   1260
gctaagaagg agaaccctgg cgagggttac atcacaatct cagactgcgc ggcattaaca   1320
gagacgttga aattcaccgc tggcgagtca gtcgagtcac tcactcactc cgacatctat   1380
tcccggcttc acaagaggtc ggacaaggaa cagatcacga accatctgag caaggagtac   1440
gagattgaga gcgacccgca tctcctgaat cgggccgagc agaacggctc ccttcctttc   1500
tcctacgtga cgaagaccat cgagatcttc cctgagacca atcgcgtccg gattgaaatc   1560
ggcgagacag gcgggacttt cattgtggag tcggtggagc tcatccagat ggagcaagtc   1620
aacgagacca caaacccgac cgtggacgtt caaatagtca tgaatgacac accggcaact   1680
aagttcaatc cagtcagttt cacagagtcg acagtctcgc caaggacagt gcattacgcc   1740
tactcacatg actcatccat tggttacgag aacccgaact ggatggacga tatcagcgga   1800
gacaccctct tctcggatct tagcctccca gggactcaca atacgatggc cctgtacggt   1860
ggcgacatta cccaatgcca gacgatgagc cttagcacac agctccaagt cggaatccgc   1920
tacctggaca ttcgttgccg ccacatcgag aacgtcttcg ccattcatca cggcccggtc   1980
tatcagaacg ctatgttcgg cgacgtctgc atagcagtcc ggaacttctt aaagtctaat   2040
ccctcagaga ccgtgttcat gcgcatcaaa gaggaacaca cagcggagaa taacacacgg   2100
tcattctccg atacctttgc cgattacaaa tcccaatact ccgatctgtt ctgggattgg   2160
acgggcgata acccgcgtct gagcgagatc cgtgggaaag tggtggttct ccagaacttc   2220
atcggtgcga agttcggcat tcactacgat accctcaata agcaagacca gtaccatctc   2280
aacactaact gggatctcta cgacaagtgg atcttcgtca aggagcacct gtacgccgcc   2340
gacaattcct acaagagcgg tcggaagcaa gtgtacctca actatctgag tggctccggc   2400
ggttccttcc cgtacttcgt ggcgtcaggc cattccagcc tggtacgga cgcgccacag   2460 ctctcaactg gcctcaccac gcccgcgttc gcctcatggt atccagactt tcctcgaggc   2520
tcctgtttca ttggtatttg cacaatctat ttcgaaggca ccaacatctt aacttcccag   2580
tggatcgaga agaacgactt caagtacatc ggtatcatcg ctgccgattt ccctggtagg   2640
acgctcatct ccaacatcat ctcgctcaac aagctgcttt cactggagat caagaacggc   2700
gggacatacc agatcgttag cgcgctgaat aactccagcg tgatcgacat gagtctctct   2760
ggcgaccgca acgttcatct gtggtcaaac aacggcacgc ttaaccaagt gtggaagttc   2820
```

```
gtctatgaca gcaaccggct tgcctaccag atcaagagcc tctcagacga gaatctggtc   2880
ctgacctggg cgtactattc cagcaaccgt gacaacgtca ttgtcgcttc caaccagaac   2940
tcagatgagc aatactggat acccgagcgg actggcgcct accactattt caagaacctg   3000
attaacccga gcggcgcact tgacgtgagt ggttcgggta ccacaaacgg caccaacatt   3060
ctctactggt cctacaaccg ggccacgaat cagaagttta agctcgagga ggtgaacatc   3120
cctggcggtc aggccgaagg cgtcctgctt tacgccgatg ccaactacgt cggcaagtcg   3180
gtgctcctca caaacagcgt ctccaacctt cgcgacgtcg ggatgaatga catcgcgtct   3240
tccatcaagt ttatcggccc gtaccaggct acccttttacg agcatgataa cttcacgggc   3300
gcggtgttca cgccgacctc caacgtggcg aacctcaaag acgtcggtat gaacgacacg   3360
gtgtcatcca tcaagattac gaagacctcc ggcggccggg ccaccggcat ctacctttac   3420
gccgatgcca attacgttgg aaggtccgta tggctgacct caaatgtggc caacctaaag   3480
gacgtcggta tgaacgacac cgtctccagc gtggagatcg tcggcgcgta tcaggcgacg   3540
ctgtacggtg actccaacta cacgggaaag gcctacaacc tgacgcataa cgtggccaac   3600
cttaaggacg tcggaatgaa tgatatcgtc tctagcatca agatcttcag cgtttag      3657
```

<210> SEQ ID NO 16
<211> LENGTH: 1218
<212> TYPE: PRT
<213> ORGANISM: Artificial
<220> FEATURE:
<223> OTHER INFORMATION: The amino acid sequence of TIC4904PL encoded by
a synthetic coding sequence designed for expression in a plant
cell, and wherein an additional alanine amino acid is inserted
immediately following the initiating methionine.

<400> SEQUENCE: 16

```
Met Ala Asp Gln Lys Ile Ile Lys Met Arg Glu Ala Val Asn Ala Leu
1               5                   10                  15

Phe Ser Asn Asn Gln Leu Lys Leu Asn Ile Thr Asp Tyr Asn Ile Asp
                20                  25                  30

Gln Ile Ala Tyr Leu Val Asp Ser Met Ser Asp Asp Ala Tyr Arg Gln
            35                  40                  45

Glu Lys Met Arg Phe Leu Asp Gln Ile Lys Phe Ala Lys Arg Leu Ser
        50                  55                  60

Gln Lys Arg Asn Leu Leu Asn Tyr Gly Asp Phe Glu Gly Ser Asn Trp
65                  70                  75                  80

Pro Gly Lys Asn Gly Trp Lys Arg Asn Asn Tyr Val Val Ala Ser
                85                  90                  95

Asp His Pro Ile Phe Lys Gly Arg Tyr Leu His Ile Pro Ser Ala Thr
                100                 105                 110

Thr Thr Met Ser Gly Ala Ile Ile Pro Thr Tyr Val Tyr Gln Arg Ile
            115                 120                 125

Asp Glu Ser Lys Leu Lys Pro Tyr Thr Arg Tyr Leu Val Arg Gly Tyr
        130                 135                 140

Val Gly Lys Ser Gln Asp Leu Ala Leu Leu Val Ser Arg Tyr Thr Lys
145                 150                 155                 160

Glu Val Tyr Lys Lys Ile Asn Val Pro Asn Asp Glu Asp Tyr Asp Ile
                165                 170                 175

Thr Ser His Ile Asn Arg Glu Glu Asn Leu Trp His Asn Arg Tyr Ile
            180                 185                 190

Arg Gly Thr Gln Val Gln Asn Ser Ile Ser Met Cys Asn Asn Pro His
        195                 200                 205
```

```
Glu Phe Thr Cys His Ile Asp Ile Gly Glu Leu Asp Arg Lys Lys Gly
    210                 215                 220

Pro Gly Ile Thr Ile Gly Phe Gln Ile Gly Thr Thr Asp Gly Met Ala
225                 230                 235                 240

Thr Leu Asp Asn Ile Glu Val Ile Glu Ala His Pro Leu Thr Gly Ser
                245                 250                 255

Ala Leu Ala Arg Ile Glu Lys Arg Glu Arg Lys Trp Lys Gln Lys Trp
                260                 265                 270

Leu Glu Asn Gln Ile Gln Ile Glu Lys Ala Val Gln Thr Val Gln Glu
            275                 280                 285

Val Ile Arg Asn Leu Phe Thr Cys Pro Gln Gln Asn Gln Leu Asn Trp
        290                 295                 300

Met Thr Thr Arg Asn Asp Ile Ala His Ala Glu Thr Leu Ile Lys Glu
305                 310                 315                 320

Ile Pro Tyr Arg Tyr Ser Gln Leu Ser Cys Gly Asp Phe Pro Ile Leu
                325                 330                 335

Pro Glu Glu Ala Tyr Asp Ile Leu Gln Gln Leu Ser Thr Ala Val Glu
                340                 345                 350

Thr Ala Lys Thr Leu Tyr Thr Gln Arg Asn Val Val Lys Asn Gly Asp
            355                 360                 365

Phe Gln Ala Gly Leu Ser Asn Trp His Arg Thr Asp Gly Ala Glu Ile
        370                 375                 380

Gln Gln Ile Gln Asn Thr Ser Ser Val Leu Val Ile Thr Asp Trp Ala
385                 390                 395                 400

Ala Asn Ile Ser Gln Asp Met Arg Val Val Glu Lys Gly Gly Tyr Leu
                405                 410                 415

Leu Arg Val Thr Ala Lys Lys Glu Asn Pro Gly Glu Gly Tyr Ile Thr
            420                 425                 430

Ile Ser Asp Cys Ala Ala Leu Thr Glu Thr Leu Lys Phe Thr Ala Gly
        435                 440                 445

Glu Ser Val Glu Ser Leu Thr His Ser Asp Ile Tyr Ser Arg Leu His
450                 455                 460

Lys Arg Ser Asp Lys Glu Gln Ile Thr Asn His Leu Ser Lys Glu Tyr
465                 470                 475                 480

Glu Ile Glu Ser Asp Pro His Leu Leu Asn Arg Ala Glu Gln Asn Gly
                485                 490                 495

Ser Leu Pro Phe Ser Tyr Val Thr Lys Thr Ile Glu Ile Phe Pro Glu
            500                 505                 510

Thr Asn Arg Val Arg Ile Glu Ile Gly Glu Thr Gly Thr Phe Ile
        515                 520                 525

Val Glu Ser Val Glu Leu Ile Gln Met Glu Gln Val Asn Glu Thr Asn
530                 535                 540

Asn Pro Thr Val Asp Val Gln Ile Val Met Asn Asp Thr Pro Ala Thr
545                 550                 555                 560

Lys Phe Asn Pro Val Ser Phe Thr Glu Ser Thr Val Ser Pro Arg Thr
                565                 570                 575

Val His Tyr Ala Tyr Ser His Asp Ser Ser Ile Gly Tyr Glu Asn Pro
            580                 585                 590

Asn Trp Met Asp Asp Ile Ser Gly Asp Thr Leu Phe Ser Asp Leu Ser
        595                 600                 605

Leu Pro Gly Thr His Asn Thr Met Ala Leu Tyr Gly Gly Asp Ile Thr
610                 615                 620
```

```
Gln Cys Gln Thr Met Ser Leu Ser Thr Gln Leu Gln Val Gly Ile Arg
625                 630                 635                 640

Tyr Leu Asp Ile Arg Cys Arg His Ile Glu Asn Val Phe Ala Ile His
            645                 650                 655

His Gly Pro Val Tyr Gln Asn Ala Met Phe Gly Asp Val Cys Ile Ala
        660                 665                 670

Val Arg Asn Phe Leu Lys Ser Asn Pro Ser Glu Thr Val Phe Met Arg
    675                 680                 685

Ile Lys Glu Glu His Thr Ala Glu Asn Asn Thr Arg Ser Phe Ser Asp
690                 695                 700

Thr Phe Ala Asp Tyr Lys Ser Gln Tyr Ser Asp Leu Phe Trp Asp Trp
705                 710                 715                 720

Thr Gly Asp Asn Pro Arg Leu Ser Glu Ile Arg Gly Lys Val Val Val
                725                 730                 735

Leu Gln Asn Phe Ile Gly Ala Lys Phe Gly Ile His Tyr Asp Thr Leu
            740                 745                 750

Asn Lys Gln Asp Gln Tyr His Leu Asn Thr Asn Trp Asp Leu Tyr Asp
            755                 760                 765

Lys Trp Ile Phe Val Lys Glu His Leu Tyr Ala Ala Asp Asn Ser Tyr
770                 775                 780

Lys Ser Gly Arg Lys Gln Val Tyr Leu Asn Tyr Leu Ser Gly Ser Gly
785                 790                 795                 800

Gly Ser Phe Pro Tyr Phe Val Ala Ser Gly His Ser Ser Pro Gly Thr
                805                 810                 815

Asp Ala Pro Gln Leu Ser Thr Gly Leu Thr Thr Pro Ala Phe Ala Ser
            820                 825                 830

Trp Tyr Pro Asp Phe Pro Arg Gly Ser Cys Phe Ile Gly Ile Cys Thr
            835                 840                 845

Ile Tyr Phe Glu Gly Thr Asn Ile Leu Thr Ser Gln Trp Ile Glu Lys
850                 855                 860

Asn Asp Phe Lys Tyr Ile Gly Ile Ala Ala Asp Phe Pro Gly Arg
865                 870                 875                 880

Thr Leu Ile Ser Asn Ile Ile Ser Leu Asn Lys Leu Leu Ser Leu Glu
            885                 890                 895

Ile Lys Asn Gly Gly Thr Tyr Gln Ile Val Ser Ala Leu Asn Asn Ser
            900                 905                 910

Ser Val Ile Asp Met Ser Leu Ser Gly Asp Arg Asn Val His Leu Trp
            915                 920                 925

Ser Asn Asn Gly Thr Leu Asn Gln Val Trp Lys Phe Val Tyr Asp Ser
930                 935                 940

Asn Arg Leu Ala Tyr Gln Ile Lys Ser Leu Ser Asp Glu Asn Leu Val
945                 950                 955                 960

Leu Thr Trp Ala Tyr Tyr Ser Ser Asn Arg Asp Asn Val Ile Val Ala
                965                 970                 975

Ser Asn Gln Asn Ser Asp Glu Gly Tyr Trp Ile Pro Glu Arg Thr Gly
            980                 985                 990

Ala Tyr His Tyr Phe Lys Asn Leu Ile Asn Pro Ser Gly Ala Leu Asp
            995                 1000                1005

Val Ser Gly Ser Gly Thr Thr Asn Gly Thr Asn Ile Leu Tyr Trp
    1010                1015                1020

Ser Tyr Asn Arg Ala Thr Asn Gln Lys Phe Lys Leu Glu Glu Val
    1025                1030                1035

Asn Ile Pro Gly Gly Gln Ala Glu Gly Val Leu Leu Tyr Ala Asp
```

```
    1040                1045                1050

Ala Asn  Tyr Val Gly Lys Ser  Val Leu Leu Thr Asn  Ser Val Ser
    1055                1060                1065

Asn Leu  Arg Asp Val Gly Met  Asn Asp Ile Ala Ser  Ser Ile Lys
    1070                1075                1080

Phe Ile  Gly Pro Tyr Gln Ala  Thr Leu Tyr Glu His  Asp Asn Phe
    1085                1090                1095

Thr Gly  Ala Val Phe Thr Pro  Thr Ser Asn Val Ala  Asn Leu Lys
    1100                1105                1110

Asp Val  Gly Met Asn Asp Thr  Val Ser Ser Ile Lys  Ile Thr Lys
    1115                1120                1125

Thr Ser  Gly Gly Arg Ala Thr  Gly Ile Tyr Leu Tyr  Ala Asp Ala
    1130                1135                1140

Asn Tyr  Val Gly Arg Ser Val  Trp Leu Thr Ser Asn  Val Ala Asn
    1145                1150                1155

Leu Lys  Asp Val Gly Met Asn  Asp Thr Val Ser Ser  Val Glu Ile
    1160                1165                1170

Val Gly  Ala Tyr Gln Ala Thr  Leu Tyr Gly Asp Ser  Asn Tyr Thr
    1175                1180                1185

Gly Lys  Ala Tyr Asn Leu Thr  His Asn Val Ala Asn  Leu Lys Asp
    1190                1195                1200

Val Gly  Met Asn Asp Ile Val  Ser Ser Ile Lys Ile  Phe Ser Val
    1205                1210                1215

<210> SEQ ID NO 17
<211> LENGTH: 3639
<212> TYPE: DNA
<213> ORGANISM: Artificial
<220> FEATURE:
<223> OTHER INFORMATION: A synthetic coding sequence encoding a TIC6547PL pesticidal protein designed for expression in a plant cell wherein an additional alanine codon is inserted immediately following the initiating methionine codon.

<400> SEQUENCE: 17

```
atggctgacc agaagatcat caagatgcgt gaggccgtca acgcgctctt ctcaaacaac     60
cagttgaagc tgaacatcac cgactacaac attgatcaga ttgcttacct cgtcgactcc    120
atgtcggacg acgcgtacag acaggagaag atgcgattcc tcgaccagat aaagtttgcc    180
aagcggctgt ctcagaaacg taacctcctt aactacggcg acttcgaggg cagcaactgg    240
cccggcaaga acggctggaa gcgcaacaac tacgttgtgg tcgcgtcaga ccacccgatc    300
tttaagggcc gctaccttca cattccgagc gccactacca ccatgtctgg cgcgattatc    360
ccgacctacg tttaccagag gatcgacgag tcgaagctca aaccctacac tcggtatctg    420
gtgcgcgggt acgtagggaa gtcccaggat ctcgcgcttc tggtctcccg ctacaccaag    480
gaagtgtaca agaagataaa cgtcccgaat gatgaggact acgacatcac ctcacacatc    540
aaccgcgagg agaacctctg gcataaccgg tacatccgcg gcactcaagt acagaactcg    600
atctctatgt gcaacaaccc gcacgagttt acatgccaca ttgacatcgg cgagctggac    660
cgcaagaagg gcccagggat caccatcggt ttccagatcg gaacaacgga tggtatggcg    720
accttggaca acatcgaagt gatcgaggcc cacccactaa ccggctctgc cctcgcgcgc    780
atccagaaac gtgagcgtaa gtggaagcag aagtggattg agaaccggat gcagatcgag    840
aaggcagtcc agacggctca ggaggtgatc aggaacctct tcacctgtcc gcagcagaac    900
cagcttaact ggatgacaac aaggaacgac atcacccatg cagagacgct gataaaggag    960
```

```
atcccgtacc gctacagcca gctgtcgtgc ggtgatttcc cgactttgcc ggaggaggcg      1020
tacgacatcc tacaacagct gagcaccgct gttgaaacag cgaaggctct ttatgctcag      1080
aggaacgtgg tgaacaacgg cgatttccag gctggcctct cgaattggta cactacggac      1140
ggcgcggaga tccagcaaat ccagaacagc agtagcgtct tagtcatcaa ggactgggca      1200
acgaacatct ctcaggacat gcgcgtcgtg gagaagggcg gctacctcct gcgtgtcaca      1260
gcgaagaagg aggatacggg tgaagggtac atcactattt ccgattgcgc tgccctggtg      1320
gagaaactta ccttcactac gggcgaagca gttgaaagcc ttgcccactc ggactcaagg      1380
tctcgcttgc acaaacggta cgataagaaa tcagaaggtt atgagatcga gagcgaccct      1440 cacctctttta accgcgcgaa gcagaacggc tcactgccct caagctacgt caccaagaca      1500
atcgaaatct ccccggaaac gaaccgggtt cgcattgaga tcggtgagac cggtggcaag      1560
ttcatggttg agtcagtaga gctgatccga atggagcaga tgaacgagac gaacaacccg      1620
gcagtggatg ttcagacagt tatgaacgat actcctgcta cccagttcga cccggtctcg      1680
tttaccgaga gcaccgtgtc gccacggaac gctcagtatg cgtactcgca cgacacaaac      1740
attggctacg agaacccgaa ttggatggca gatatcagcg gtgatacgct cttcagcgac      1800
ctgagcattc ccggcacgca caatacgatg gctttgcatg gcggcgatat cacccaatgt      1860
cagactatgt ctctgaacac acagttgcac gtgggaatcc gctacttgga catccgttgc      1920
cgccacatcg acaacgtctt cgccatccat cacggcccgg tgtaccagaa cactatgttc      1980
ggcgacgtct gcatagcagt gcgggacttc ttgcgtaaca cccgagcga accgtcttc       2040 atgcgtatta aggaggaaca cactccggag aacaatacc gctctttcag tgacaccttc      2100
gccgactaca gtctcagta cagcgacctg ttctggaact ggacgggcga caaccctcgc      2160
ctatctgaga tccgtggaaa ggtcgtcgtg ctgcagaact tctccggcga ccgcttcggc      2220
atctactaca atacgctgaa cacccaggac cagtatcacc tcgacactaa ctgggatctt      2280
tatgacaagt ggctcttcgt aaaggagcat ctttacaaag ccgatgatgc gtacaagtcc      2340
ggcggcaaac aggcttacct caactatcta agtggctcgg gcggctcgtt tccctacttt      2400
gtggcctcgg gccactcatc gcctggtact gacgcgcctc agctcagcac cggcctcacc      2460
acgccggcct tcgctagctg gtatccagac ttcccacgcg gttcttgctt catcgggatc      2520
tgtacgatct acttcgaggg cacaaacatt ctgaccagcc agtggatcga agaatgat       2580 ttcaagtaca ttggcataat cgcagccgac ttcccaggcc ggacgctcat ctcaaacatc      2640
atctccctaa acaagcttct cagcttggag atcaagaacg gcggcaccta tcagatagtc      2700
agcgcgctca caatagctc tgtaatcgac atgtcccttt ccggagaccg taatgcacac      2760
ctatggtcaa caacgggac gccaaaccag gtctggaagt tgtgtacga tagcaatcgc       2820 ttagcatacc agatcaagag cctcagcgac gagaacctcg tcctcacatg gcctattac      2880 tcctccaacc gcgataacgt catcgtcgcc tcaaaccaga actcagacga gcagtattgg      2940
attccagagc ggactggcgc ctatcactac tttaagaacc tcatcaatcc gtcgggcgcc      3000
ctggatgttt ccgggagcgg cactaccaat gggaccaaca tcttgtactg gtcgtacaac      3060
agggccacga accagaagtt caagctcgag gaggtgaaca tctccggagg ccagactgag      3120
ggcgtgcttc tgtacgcgga ggccaactat gttggcaaga gtgtcctgct cacgaactcc      3180
gtctccaatc tgcgcgacgt gggcatgaac gacatcgcct ctagcattaa gttcatcggc      3240
ccgtaccaag ctacgctcta cgagcatgac gacttcactg gagccgtctt cacaccgacg      3300
```

```
agtaacgtgg cgaacctcaa agacgttgga atgaacgata cggtcagctc gatcaagatc    3360
accaagacgt cgggcggcag agccacgggc atctacctct acgccgacgc caactacgtg    3420
ggccgctcgg tgtggctgac ctcgaacgta gccaatttga aggacgtggg catgaacgac    3480
accgtgtcga gcgtggaaat tgttggtgcc taccaggcga cactctacgg cgacagcaac    3540
tacaccggca aggcgtacaa cctgacacac aacgtggcca accttaaaga cgtgggcatg    3600
aacgacatcg tgtcttccat caagatcttc agcgtgtga                          3639
```

<210> SEQ ID NO 18
<211> LENGTH: 1212
<212> TYPE: PRT
<213> ORGANISM: Artificial
<220> FEATURE:
<223> OTHER INFORMATION: The amino acid sequence of TIC6547PL encoded by
      a synthetic coding sequence designed for expression in a plant
      cell, and wherein an additional alanine amino acid is inserted
      immediately following the initiating methionine.

<400> SEQUENCE: 18

```
Met Ala Asp Gln Lys Ile Ile Lys Met Arg Glu Ala Val Asn Ala Leu
1               5                   10                  15

Phe Ser Asn Asn Gln Leu Lys Leu Asn Ile Thr Asp Tyr Asn Ile Asp
            20                  25                  30

Gln Ile Ala Tyr Leu Val Asp Ser Met Ser Asp Ala Tyr Arg Gln
        35                  40                  45

Glu Lys Met Arg Phe Leu Asp Gln Ile Lys Phe Ala Lys Arg Leu Ser
    50                  55                  60

Gln Lys Arg Asn Leu Leu Asn Tyr Gly Asp Phe Glu Gly Ser Asn Trp
65                  70                  75                  80

Pro Gly Lys Asn Gly Trp Lys Arg Asn Asn Tyr Val Val Val Ala Ser
                85                  90                  95

Asp His Pro Ile Phe Lys Gly Arg Tyr Leu His Ile Pro Ser Ala Thr
            100                 105                 110

Thr Thr Met Ser Gly Ala Ile Ile Pro Thr Tyr Val Tyr Gln Arg Ile
        115                 120                 125

Asp Glu Ser Lys Leu Lys Pro Tyr Thr Arg Tyr Leu Val Arg Gly Tyr
    130                 135                 140

Val Gly Lys Ser Gln Asp Leu Ala Leu Leu Val Ser Arg Tyr Thr Lys
145                 150                 155                 160

Glu Val Tyr Lys Lys Ile Asn Val Pro Asn Asp Glu Asp Tyr Asp Ile
                165                 170                 175

Thr Ser His Ile Asn Arg Glu Glu Asn Leu Trp His Asn Arg Tyr Ile
            180                 185                 190

Arg Gly Thr Gln Val Gln Asn Ser Ile Ser Met Cys Asn Asn Pro His
        195                 200                 205

Glu Phe Thr Cys His Ile Asp Ile Gly Glu Leu Asp Arg Lys Lys Gly
    210                 215                 220

Pro Gly Ile Thr Ile Gly Phe Gln Ile Gly Thr Thr Asp Gly Met Ala
225                 230                 235                 240

Thr Leu Asp Asn Ile Glu Val Ile Glu Ala His Pro Leu Thr Gly Ser
                245                 250                 255

Ala Leu Ala Arg Ile Gln Lys Arg Glu Arg Lys Trp Lys Gln Lys Trp
            260                 265                 270

Ile Glu Asn Arg Met Gln Ile Glu Lys Ala Val Gln Thr Ala Gln Glu
        275                 280                 285
```

```
Val Ile Arg Asn Leu Phe Thr Cys Pro Gln Gln Asn Gln Leu Asn Trp
    290                 295                 300
Met Thr Thr Arg Asn Asp Ile Thr His Ala Glu Thr Leu Ile Lys Glu
305                 310                 315                 320
Ile Pro Tyr Arg Tyr Ser Gln Leu Ser Cys Gly Asp Phe Pro Thr Leu
                325                 330                 335
Pro Glu Glu Ala Tyr Asp Ile Leu Gln Gln Leu Ser Thr Ala Val Glu
            340                 345                 350
Thr Ala Lys Ala Leu Tyr Ala Gln Arg Asn Val Val Asn Asn Gly Asp
        355                 360                 365
Phe Gln Ala Gly Leu Ser Asn Trp Tyr Thr Thr Asp Gly Ala Glu Ile
370                 375                 380
Gln Gln Ile Gln Asn Ser Ser Val Leu Val Ile Lys Asp Trp Ala
385                 390                 395                 400
Thr Asn Ile Ser Gln Asp Met Arg Val Glu Lys Gly Gly Tyr Leu
                405                 410                 415
Leu Arg Val Thr Ala Lys Lys Glu Asp Thr Gly Glu Gly Tyr Ile Thr
            420                 425                 430
Ile Ser Asp Cys Ala Ala Leu Val Glu Lys Leu Thr Phe Thr Thr Gly
        435                 440                 445
Glu Ala Val Glu Ser Leu Ala His Ser Asp Ser Arg Ser Arg Leu His
450                 455                 460
Lys Arg Tyr Asp Lys Lys Ser Glu Gly Tyr Glu Ile Glu Ser Asp Pro
465                 470                 475                 480
His Leu Phe Asn Arg Ala Lys Gln Asn Gly Ser Leu Pro Ser Ser Tyr
                485                 490                 495
Val Thr Lys Thr Ile Glu Ile Phe Pro Glu Thr Asn Arg Val Arg Ile
            500                 505                 510
Glu Ile Gly Glu Thr Gly Gly Lys Phe Met Val Glu Ser Val Glu Leu
        515                 520                 525
Ile Arg Met Glu Gln Met Asn Glu Thr Asn Pro Ala Val Asp Val
530                 535                 540
Gln Thr Val Met Asn Asp Thr Pro Ala Thr Gln Phe Asp Pro Val Ser
545                 550                 555                 560
Phe Thr Glu Ser Thr Val Ser Pro Arg Asn Ala Gln Tyr Ala Tyr Ser
                565                 570                 575
His Asp Thr Asn Ile Gly Tyr Glu Asn Pro Asn Trp Met Ala Asp Ile
            580                 585                 590
Ser Gly Asp Thr Leu Phe Ser Asp Leu Ser Ile Pro Gly Thr His Asn
        595                 600                 605
Thr Met Ala Leu His Gly Gly Asp Ile Thr Gln Cys Gln Thr Met Ser
610                 615                 620
Leu Asn Thr Gln Leu His Val Gly Ile Arg Tyr Leu Asp Ile Arg Cys
625                 630                 635                 640
Arg His Ile Asp Asn Val Phe Ala Ile His His Gly Pro Val Tyr Gln
                645                 650                 655
Asn Thr Met Phe Gly Asp Val Cys Ile Ala Val Arg Asp Phe Leu Arg
            660                 665                 670
Asn Asn Pro Ser Glu Thr Val Phe Met Arg Ile Lys Glu Glu His Thr
        675                 680                 685
Pro Glu Asn Asn Thr Arg Ser Phe Ser Asp Thr Phe Ala Asp Tyr Lys
690                 695                 700
Ser Gln Tyr Ser Asp Leu Phe Trp Asn Trp Thr Gly Asp Asn Pro Arg
```

```
            705                 710                 715                 720
Leu Ser Glu Ile Arg Gly Lys Val Val Leu Gln Asn Phe Ser Gly
                725                 730                 735

Asp Arg Phe Gly Ile Tyr Tyr Asn Thr Leu Asn Thr Gln Asp Gln Tyr
                740                 745                 750

His Leu Asp Thr Asn Trp Asp Leu Tyr Asp Lys Trp Leu Phe Val Lys
                755                 760                 765

Glu His Leu Tyr Lys Ala Asp Asp Ala Tyr Lys Ser Gly Gly Lys Gln
                770                 775                 780

Ala Tyr Leu Asn Tyr Leu Ser Gly Ser Gly Ser Phe Pro Tyr Phe
785                 790                 795                 800

Val Ala Ser Gly His Ser Ser Pro Gly Thr Asp Ala Pro Gln Leu Ser
                805                 810                 815

Thr Gly Leu Thr Thr Pro Ala Phe Ala Ser Trp Tyr Pro Asp Phe Pro
                820                 825                 830

Arg Gly Ser Cys Phe Ile Gly Ile Cys Thr Ile Tyr Phe Glu Gly Thr
                835                 840                 845

Asn Ile Leu Thr Ser Gln Trp Ile Glu Lys Asn Asp Phe Lys Tyr Ile
                850                 855                 860

Gly Ile Ile Ala Ala Asp Phe Pro Gly Arg Thr Leu Ile Ser Asn Ile
865                 870                 875                 880

Ile Ser Leu Asn Lys Leu Leu Ser Leu Glu Ile Lys Asn Gly Gly Thr
                885                 890                 895

Tyr Gln Ile Val Ser Ala Leu Asn Asn Ser Ser Val Ile Asp Met Ser
                900                 905                 910

Leu Ser Gly Asp Arg Asn Ala His Leu Trp Ser Asn Asn Gly Thr Pro
                915                 920                 925

Asn Gln Val Trp Lys Phe Val Tyr Asp Ser Asn Arg Leu Ala Tyr Gln
                930                 935                 940

Ile Lys Ser Leu Ser Asp Glu Asn Leu Val Leu Thr Trp Ala Tyr Tyr
945                 950                 955                 960

Ser Ser Asn Arg Asp Asn Val Ile Val Ala Ser Asn Gln Asn Ser Asp
                965                 970                 975

Glu Gln Tyr Trp Ile Pro Glu Arg Thr Gly Ala Tyr His Tyr Phe Lys
                980                 985                 990

Asn Leu Ile Asn Pro Ser Gly Ala Leu Asp Val Ser Gly Ser Gly Thr
                995                 1000                1005

Thr Asn Gly Thr Asn Ile Leu Tyr Trp Ser Tyr Asn Arg Ala Thr
                1010                1015                1020

Asn Gln Lys Phe Lys Leu Glu Glu Val Asn Ile Ser Gly Gly Gln
                1025                1030                1035

Thr Glu Gly Val Leu Leu Tyr Ala Glu Ala Asn Tyr Val Gly Lys
                1040                1045                1050

Ser Val Leu Leu Thr Asn Ser Val Ser Asn Leu Arg Asp Val Gly
                1055                1060                1065

Met Asn Asp Ile Ala Ser Ser Ile Lys Phe Ile Gly Pro Tyr Gln
                1070                1075                1080

Ala Thr Leu Tyr Glu His Asp Asp Phe Thr Gly Ala Val Phe Thr
                1085                1090                1095

Pro Thr Ser Asn Val Ala Asn Leu Lys Asp Val Gly Met Asn Asp
                1100                1105                1110

Thr Val Ser Ser Ile Lys Ile Thr Lys Thr Ser Gly Gly Arg Ala
                1115                1120                1125
```

```
Thr Gly Ile Tyr Leu Tyr Ala Asp Ala Asn Tyr Val Gly Arg Ser
    1130            1135            1140

Val Trp Leu Thr Ser Asn Val Ala Asn Leu Lys Asp Val Gly Met
    1145            1150            1155

Asn Asp Thr Val Ser Ser Val Glu Ile Val Gly Ala Tyr Gln Ala
    1160            1165            1170

Thr Leu Tyr Gly Asp Ser Asn Tyr Thr Gly Lys Ala Tyr Asn Leu
    1175            1180            1185

Thr His Asn Val Ala Asn Leu Lys Asp Val Gly Met Asn Asp Ile
    1190            1195            1200

Val Ser Ser Ile Lys Ile Phe Ser Val
    1205            1210
```

<210> SEQ ID NO 19
<211> LENGTH: 3645
<212> TYPE: DNA
<213> ORGANISM: Artificial
<220> FEATURE:
<223> OTHER INFORMATION: A synthetic coding sequence encoding a
      TIC4006PL pesticidal protein designed for expression in a plant
      cell wherein an additional alanine codon is inserted immediately
      following the initiating methionine codon.

<400> SEQUENCE: 19

```
atggctaacc agtatgtgac aacggtccag aaggcggtga atgcgctgtt ctcgaataac      60
acgcttccgc tcaacatcac cgactacaac attgaccaaa ctgcctacct cgttgagcgc     120
atctccaacg accggtactc caaagacaag atgatgctcc tcaaccaggt gaagtttgcg     180
aagcgcctga ccgcgcccg gaacttgctc aagggcggcg cgttcgaact gtccgacaag     240
aaccgctgga gaccaacaa ctacgcaaac atcctgtccg gttccctgct cagcaagggc     300
cagtccctca acatcctgag cgcgagcccg accgtgtctt cgcagattat ccctacgcat     360
gtgtaccagc gcatcgacga gagcaagctc aagccctaca cacgctacct cgtgcgcgga     420
ttcgttgaga gtcccgtga ccttgagctc ttcgttcttc gctacaacaa ggaggtgtac     480
aagaggatca acgtcccgaa gaatgaggac taccacataa cgagccacct gaacgaggag     540
gagaatccgt ggcacaacaa gtacatccag aacactcccg tgcagaactc gatttccatg     600
cgcaagaact cacacgagtt cacatgccac atcgacattg tgaattgga catcaagaag     660
ggtccgggca tcacaatcgg ctttcagatc tccacaacgg acggtatggc cactctcgat     720
aacatcgaag tcattgaggc ccaccctctt accggagatg accttacccg gattcaaaga     780
cgggagcgga agtggaagca gaagtggctc gagaaccaga ttcagattga aaggccgct     840
caaacagcga agaggccat caagaacctc ttcacttgcc ctcaacagaa ccagctcacg     900
tggatgacaa ccttaaacga tatcatccag gcggagaaac ttattcaaga aatcccgtac     960
tggtactcac gtctgcttgg tgaggacttc cctatccttc tgaggaggc ctacgacacc    1020
ttgcagcagt tatccaccgc cgtggagacc gcgaagctgc tgtacgctca ggaacgtc    1080
gtcaacaatg gcgacttcca ggcgggcttc tctaattgga acaccacgga cggtgcggag    1140
ataaagcaaa tccaggactc cagcagcgtt tcgtgatca ccgactgggc tgcgaacatc    1200
tcacaggaca tgcgcgtggt ggagaaggga ggttacctgc tgagagttac agccaagaag    1260
gaggatgcgg cgagggcta cataaccatc tctgactgta gcgtagtgat ggagaagcta    1320
accttcacta ctggtgacag tgtcgagagc ctggcgcact ccgacatcta ctctcgcatc    1380
cacaagcgct acgcgaagaa gcagattacg aaccacctct cagagcgtta tgagatcgag    1440
```

```
tcgaacccgc acttgattaa ccgcgctgag cagaacgcca gccttccatc aagctacgtg   1500
accaagacga tcgaggtctt cccggagaca atcgggtgc gcgtcgagat aggtgagaca    1560
ggcggcacat tcattgtcga gagcgtcgag ctgatccgaa tggagcagat gaatgagacc   1620
aacaatcccg ccgtcgacat tcagaccgtt atgaatgaca cgcctgctac gcagttcgac   1680
cctgtttcct tcactgagtc gacagtgtcg ccaaggaaca cgcaatacgc ctattcacac   1740
gattcgaaca tcggctatga gaaccctaac tggatggctg acatctcagg cgataccttg   1800
ttctcggatc ttagcatccc aggcacacac aacacgatgg ccttctacgg tggcgacatc   1860
acgcagtgcc aaacgatgag cctcaacacc caacttcacg tgggcatccg ctacctagac   1920
atccgctgca gacacattga gaacatcttc gccatccatc acggaattgt gtaccagaac   1980 gcgacctta ctgacgtctg catcgcagtc agggacttcc tcaggaacaa ccctagcgaa    2040
accgtgttta tgaggatcaa ggaggaacat acagcggaga caacaccag atccttcggt    2100 gagacgttcg ccgattacaa gagccaatac tccgacctct tctggaactg acaggcgat    2160 aatccgaggc tgtccgagat ccgcgggaag gtggtggtac ttcagaactt cttcggcgac   2220
aagttcggga tcgactacaa cacgctgaac aaacaggatc aataccacct gaacactaac   2280
tgggatctct acgacaagtg gctcttcgtg aaggagcacc tgtacgcggc tgacgatagc   2340
tacaagaacg ggcgcaagca agcgtacctc aactatctta gtggctccgg aggttcattc   2400
ccgtacttcg tcgcgtccgg ccattccagc cctggtacga atgcgtccaa cctgtccacc   2460
ggtctgacaa caccgcgtt tgagtcttgg tatccagatt ccctcgcgg ctcttgcttc     2520 atagggatct gcaccatcta ctttgagggc acaaacatcc tgacatcaga gtggattcag   2580
aagtcggact tcaaatacgt gggcatcatt gccgcggact tcccagggcg caccctgatc   2640
tccaacataa tctcccttaa taaccttctt tcgctcgaga ttaagaacgg cgggacatac   2700
cagatcgtgt cggctcttaa caattcgagc gtggtggaca tgaatcccgg cgaccagaac   2760
atccacctgt ggaacaataa cggtacggct aaccagctgt ggaagttcgt ttacaacagc   2820
aacgagcttg cctatcagat caagtctctc tcaaacgaga acctcgttct tacgtgggcg   2880
tacaactcct ccaacccgga caacgtgatc gcagcctcga accagaaccg ttctgaacag   2940
tactggatcc ctgagcgcac cggtgcctac cactacttca gaaccttc gaaccgctcg    3000 ggagccttgg atgtcagtgg gtcggaaacg aagaacggga cgaacatcct gtactggtcc   3060
tacaagaagg ctactaatca gaagttcaag ctcaccgagg tgaacgtttc tggcggccaa   3120
gccgaaggcg tgtacctgta cgctgacgcg aactacgtcg gccagtctgt gggcctgacc   3180
aactccgtgg ccgacttgtc ggaggtgggc atgaacgata tcgcttcttc gatcaagttc   3240
atcgggccct accaggccac actctacgag cacgctgact tcaagggtgc ggtcttcact   3300
ccgaccacca acatcgccaa tctcaaggac gtgggcatga acgacaccat ctcgagcatc   3360
aagatcacta agacctccgg cggaagggcg gccggcatct acctctactc cgacgccaac   3420
tacgtcggga ggtctatctg gctgacgagc aacgtcgcga atcttaaaga cgtgggcatg   3480
aacgatacca tctcttccgt cgagatagtc ggcgcgtacg gcgtgaccct ctacggcgac   3540
gcgaactaca cgggcaaggc ctacgcactt acctccaacg tggctaacct caaggatgtc   3600
gggatgaacg acatcgtttc gagcatcaag atcttctcag tttag                  3645
```

<210> SEQ ID NO 20
<211> LENGTH: 1214
<212> TYPE: PRT

<213> ORGANISM: Artificial
<220> FEATURE:
<223> OTHER INFORMATION: The amino acid sequence of TIC4006PL encoded by a synthetic coding sequence designed for expression in a plant cell, and wherein an additional alanine amino acid is inserted immediately following the initiating methionine.

<400> SEQUENCE: 20

```
Met Ala Asn Gln Tyr Val Thr Thr Val Gln Lys Ala Val Asn Ala Leu
1               5                   10                  15

Phe Ser Asn Asn Thr Leu Pro Leu Asn Ile Thr Asp Tyr Asn Ile Asp
            20                  25                  30

Gln Thr Ala Tyr Leu Val Glu Arg Ile Ser Asn Asp Arg Tyr Ser Lys
        35                  40                  45

Asp Lys Met Met Leu Leu Asn Gln Val Lys Phe Ala Lys Arg Leu Ser
50                  55                  60

Arg Ala Arg Asn Leu Leu Lys Gly Gly Ala Phe Glu Leu Ser Asp Lys
65                  70                  75                  80

Asn Arg Trp Lys Thr Asn Asn Tyr Ala Asn Ile Leu Ser Gly Ser Leu
            85                  90                  95

Leu Ser Lys Gly Gln Ser Leu Asn Ile Leu Ser Ala Ser Pro Thr Val
            100                 105                 110

Ser Ser Gln Ile Ile Pro Thr His Val Tyr Gln Arg Ile Asp Glu Ser
            115                 120                 125

Lys Leu Lys Pro Tyr Thr Arg Tyr Leu Val Arg Gly Phe Val Glu Lys
            130                 135                 140

Ser Arg Asp Leu Glu Leu Phe Val Leu Arg Tyr Asn Lys Glu Val Tyr
145                 150                 155                 160

Lys Arg Ile Asn Val Pro Lys Asn Glu Asp Tyr His Ile Thr Ser His
                165                 170                 175

Leu Asn Glu Glu Glu Asn Pro Trp His Asn Lys Tyr Ile Gln Asn Thr
            180                 185                 190

Pro Val Gln Asn Ser Ile Ser Met Arg Lys Asn Ser His Glu Phe Thr
            195                 200                 205

Cys His Ile Asp Ile Gly Glu Leu Asp Ile Lys Lys Gly Pro Gly Ile
210                 215                 220

Thr Ile Gly Phe Gln Ile Ser Thr Thr Asp Gly Met Ala Thr Leu Asp
225                 230                 235                 240

Asn Ile Glu Val Ile Glu Ala His Pro Leu Thr Gly Asp Asp Leu Thr
                245                 250                 255

Arg Ile Gln Arg Arg Glu Arg Lys Trp Lys Gln Lys Trp Leu Glu Asn
            260                 265                 270

Gln Ile Gln Ile Glu Lys Ala Ala Gln Thr Ala Lys Glu Ala Ile Lys
            275                 280                 285

Asn Leu Phe Thr Cys Pro Gln Gln Asn Gln Leu Thr Trp Met Thr Thr
            290                 295                 300

Leu Asn Asp Ile Ile Gln Ala Glu Lys Leu Ile Gln Glu Ile Pro Tyr
305                 310                 315                 320

Trp Tyr Ser Arg Leu Leu Gly Glu Asp Phe Pro Ile Leu Pro Glu Glu
                325                 330                 335

Ala Tyr Asp Thr Leu Gln Gln Leu Ser Thr Ala Val Glu Thr Ala Lys
            340                 345                 350

Leu Leu Tyr Ala Gln Arg Asn Val Val Asn Asn Gly Asp Phe Gln Ala
            355                 360                 365

Gly Phe Ser Asn Trp Asn Thr Thr Asp Gly Ala Glu Ile Lys Gln Ile
```

```
              370                 375                 380
Gln Asp Ser Ser Val Leu Val Ile Thr Asp Trp Ala Ala Asn Ile
385                 390                 395                 400

Ser Gln Asp Met Arg Val Val Glu Lys Gly Gly Tyr Leu Leu Arg Val
                405                 410                 415

Thr Ala Lys Lys Glu Asp Ala Gly Gly Tyr Ile Thr Ile Ser Asp
                420                 425                 430

Cys Ser Val Val Met Glu Lys Leu Thr Phe Thr Thr Gly Asp Ser Val
                435                 440                 445

Glu Ser Leu Ala His Ser Asp Ile Tyr Ser Arg Ile His Lys Arg Tyr
450                 455                 460

Ala Lys Lys Gln Ile Thr Asn His Leu Ser Glu Arg Tyr Glu Ile Glu
465                 470                 475                 480

Ser Asn Pro His Leu Ile Asn Arg Ala Glu Gln Asn Ala Ser Leu Pro
                485                 490                 495

Ser Ser Tyr Val Thr Lys Thr Ile Glu Val Phe Pro Glu Thr Asn Arg
                500                 505                 510

Val Arg Val Glu Ile Gly Glu Thr Gly Gly Thr Phe Ile Val Glu Ser
                515                 520                 525

Val Glu Leu Ile Arg Met Glu Gln Met Asn Glu Thr Asn Asn Pro Ala
                530                 535                 540

Val Asp Ile Gln Thr Val Met Asn Asp Thr Pro Ala Thr Gln Phe Asp
545                 550                 555                 560

Pro Val Ser Phe Thr Glu Ser Thr Val Ser Pro Arg Asn Thr Gln Tyr
                565                 570                 575

Ala Tyr Ser His Asp Ser Asn Ile Gly Tyr Glu Asn Pro Asn Trp Met
                580                 585                 590

Ala Asp Ile Ser Gly Asp Thr Leu Phe Ser Asp Leu Ser Ile Pro Gly
                595                 600                 605

Thr His Asn Thr Met Ala Phe Tyr Gly Gly Asp Ile Thr Gln Cys Gln
                610                 615                 620

Thr Met Ser Leu Asn Thr Gln Leu His Val Gly Ile Arg Tyr Leu Asp
625                 630                 635                 640

Ile Arg Cys Arg His Ile Glu Asn Ile Phe Ala Ile His His Gly Ile
                645                 650                 655

Val Tyr Gln Asn Ala Thr Phe Thr Asp Val Cys Ile Ala Val Arg Asp
                660                 665                 670

Phe Leu Arg Asn Asn Pro Ser Glu Thr Val Phe Met Arg Ile Lys Glu
                675                 680                 685

Glu His Thr Ala Glu Asn Asn Thr Arg Ser Phe Gly Glu Thr Phe Ala
                690                 695                 700

Asp Tyr Lys Ser Gln Tyr Ser Asp Leu Phe Trp Asn Trp Thr Gly Asp
705                 710                 715                 720

Asn Pro Arg Leu Ser Glu Ile Arg Gly Lys Val Val Leu Gln Asn
                725                 730                 735

Phe Phe Gly Asp Lys Phe Gly Ile Asp Tyr Asn Thr Leu Asn Lys Gln
                740                 745                 750

Asp Gln Tyr His Leu Asn Thr Asn Trp Asp Leu Tyr Asp Lys Trp Leu
                755                 760                 765

Phe Val Lys Glu His Leu Tyr Ala Ala Asp Asp Ser Tyr Lys Asn Gly
                770                 775                 780

Arg Lys Gln Ala Tyr Leu Asn Tyr Leu Ser Gly Ser Gly Gly Ser Phe
785                 790                 795                 800
```

```
Pro Tyr Phe Val Ala Ser Gly His Ser Ser Pro Gly Thr Asn Ala Ser
            805                 810                 815

Asn Leu Ser Thr Gly Leu Thr Thr Pro Ala Phe Glu Ser Trp Tyr Pro
            820                 825                 830

Asp Phe Pro Arg Gly Ser Cys Phe Ile Gly Ile Cys Thr Ile Tyr Phe
            835                 840                 845

Glu Gly Thr Asn Ile Leu Thr Ser Glu Trp Ile Gln Lys Ser Asp Phe
            850                 855                 860

Lys Tyr Val Gly Ile Ile Ala Ala Asp Phe Pro Gly Arg Thr Leu Ile
865                 870                 875                 880

Ser Asn Ile Ile Ser Leu Asn Asn Leu Ser Leu Glu Ile Lys Asn
            885                 890                 895

Gly Gly Thr Tyr Gln Ile Val Ser Ala Leu Asn Asn Ser Ser Val Val
            900                 905                 910

Asp Met Asn Pro Gly Asp Gln Asn Ile His Leu Trp Asn Asn Asn Gly
            915                 920                 925

Thr Ala Asn Gln Leu Trp Lys Phe Val Tyr Asn Ser Asn Glu Leu Ala
            930                 935                 940

Tyr Gln Ile Lys Ser Leu Ser Asn Glu Asn Leu Val Leu Thr Trp Ala
945                 950                 955                 960

Tyr Asn Ser Ser Asn Pro Asp Asn Val Ile Ala Ala Ser Asn Gln Asn
            965                 970                 975

Arg Ser Glu Gln Tyr Trp Ile Pro Gly Arg Thr Gly Ala Tyr His Tyr
            980                 985                 990

Phe Lys Asn Leu Ser Asn Arg Ser  Gly Ala Leu Asp Val  Ser Gly Ser
            995                  1000                 1005

Glu Thr Lys Asn Gly Thr Asn  Ile Leu Tyr Trp Ser  Tyr Lys Lys
     1010                1015                1020

Ala Thr Asn Gln Lys Phe Lys  Leu Thr Glu Val Asn  Val Ser Gly
     1025                1030                1035

Gly Gln Ala Glu Gly Val Tyr  Leu Tyr Ala Asp Ala  Asn Tyr Val
     1040                1045                1050

Gly Gln Ser Val Gly Leu Thr  Asn Ser Val Ala Asp  Leu Ser Glu
     1055                1060                1065

Val Gly Met Asn Asp Ile Ala  Ser Ser Ile Lys Phe  Ile Gly Pro
     1070                1075                1080

Tyr Gln Ala Thr Leu Tyr Glu  His Ala Asp Phe Lys  Gly Ala Val
     1085                1090                1095

Phe Thr Pro Thr Thr Asn Ile  Ala Asn Leu Lys Asp  Val Gly Met
     1100                1105                1110

Asn Asp Thr Ile Ser Ser Ile  Lys Ile Thr Lys Thr  Ser Gly Gly
     1115                1120                1125

Arg Ala Ala Gly Ile Tyr Leu  Tyr Ser Asp Ala Asn  Tyr Val Gly
     1130                1135                1140

Arg Ser Ile Trp Leu Thr Ser  Asn Val Ala Asn Leu  Lys Asp Val
     1145                1150                1155

Gly Met Asn Asp Thr Ile Ser  Ser Val Glu Ile Val  Gly Ala Tyr
     1160                1165                1170

Gly Val Thr Leu Tyr Gly Asp  Ala Asn Tyr Thr Gly  Lys Ala Tyr
     1175                1180                1185

Ala Leu Thr Ser Asn Val Ala  Asn Leu Lys Asp Val  Gly Met Asn
     1190                1195                1200
```

Asp Ile Val Ser Ser Ile Lys Ile Phe Ser Val
    1205                1210

<210> SEQ ID NO 21
<211> LENGTH: 3678
<212> TYPE: DNA
<213> ORGANISM: Artificial
<220> FEATURE:
<223> OTHER INFORMATION: A nucleotide sequence encoding TIC4747_His
      comprised of a histidine tag coding sequence operably linked 3' to
      the TIC4747 coding sequence.

<400> SEQUENCE: 21

| | | | | | |
|---|---|---|---|---|---|
| atggatcaaa | agattataaa | aatgcgagaa | gcagtcaatg | ccttgttttc | caataatcat | 60 |
| ttaaaattga | atattactga | ttacaatata | gatcagactg | cataccttgt | tgatagtatg | 120 |
| tctgatgacg | catatcgaca | agaaaaaatg | atgtttctcg | atcaaatcaa | atttgcaaag | 180 |
| cgcttgagcc | aaaaacgcaa | cctgttgaat | catggagatt | ttgaaggatc | caattggaca | 240 |
| ggtaagaatg | gatggaaaag | aataattat | gtagttgtcg | catcggatca | tcctatattt | 300 |
| aaaggccgat | atttacacat | accaggtgca | acaaccgcga | tgagtggcgc | aatcattccg | 360 |
| acttatgtat | atcaaagtat | agatgaatcg | aagttaaaac | cgtatacacg | ttatttggta | 420 |
| cgagggtttg | ttggaaagag | tcaagattta | gcgttacttg | tttcccggta | taccaaagaa | 480 |
| gtgtacaaga | aaatcaatgt | accaaatgat | aaagactacg | atatgacatc | gcatataaat | 540 |
| agggaagaga | atctatggca | caatagatat | ataaaagaca | cttcggttca | aaattcaatc | 600 |
| tctatgtgca | aaaatccaca | tgaatttacg | tgtcatattg | atataggga | actggataga | 660 |
| aagaaaggtc | ctggtataac | catcggtttt | caaattggaa | caacagatgg | gatggcaaca | 720 |
| ttagataata | tagaagtgat | agaagcacat | ccgttaaccg | atacgccttt | agcacgtatc | 780 |
| gaaaaacgtg | aacgtaaatg | gaaacaaaaa | tggctagagc | atcgaataca | aatcgaaaag | 840 |
| gctgtgcaaa | cagcgcaaga | ggtgattcga | aatttatta | catgcccaca | acaaaatcaa | 900 |
| ttgaactgga | tgacaacccg | aaacgacatt | gcacatgcag | aaacattgat | aaaagagatt | 960 |
| tcatatcggt | atagccaact | ttcttgtgga | gatttcccca | tactaccaga | agaggcgtat | 1020 |
| gacatccttc | aacaactttc | aactgcagtt | gaaaccgcaa | aagcgttgta | tacacaacga | 1080 |
| aacgtggtga | ataatgggga | ttttcaagct | ggattatcga | attggcatag | gacagatggt | 1140 |
| gcagagatac | aacaaattca | gaatgcatcc | tctgttctaa | taattacaga | ctgggctgcg | 1200 |
| aatatttcac | aagacatgcg | tgtagttgaa | aaaggtagct | atctgttgcg | cgtaacagcg | 1260 |
| aaaaaagaag | atgccggaga | aggttatatt | acaattagtg | attgtgccgc | attgatagaa | 1320 |
| acattgacat | ttacaacggg | ggaatctgtg | gaaagtctga | cacattctga | tattcattca | 1380 |
| aggctccata | aacgctataa | taaaaaacac | ataaaaaacc | atccttcaga | agaatatgaa | 1440 |
| atagaatcgg | atcttcattt | atttaatagg | gcggaacaaa | acggttctct | ccctctagc | 1500 |
| tatgtaacca | aaacgatgga | aatctttccg | gaaaccaatc | gagtacgcat | gaaattgga | 1560 |
| gaaacaggtg | aacatttat | agtggaaagt | gtggaattaa | ttcgaatgga | acagatgaac | 1620 |
| gaaacaaaca | atccagatgt | agatgttcaa | attgtaatga | atgatacacc | cgctacacaa | 1680 |
| tttgatccag | tttcttttac | agaatccacg | gtgaggccca | gaaatgctca | gtatgcatat | 1740 |
| tctcatgatt | caaatatagg | ttatgaaaat | cctaactgga | tggctgatat | ttcaggtgat | 1800 |
| actttattta | ctgatttatc | tatccctggt | acacataata | caatggctct | ttatggagga | 1860 |
| gatattacac | aatgtcaaac | gatgtcactg | aatacgcaat | tacatgtagg | aattcgttat | 1920 |

| | | |
|---|---|---|
| ttagatattc gctgtaggca catagaaaat gcttttgcga ttcatcatgg acctgtgtac | 1980 | |
| caaaatgcga tgtttggaga tgtttgtatt gccgtaagga atttttttgag aagcaaccct | 2040 | |
| agtgaaacag tatttatgcg gataaaagaa gaacatacag cagaaaacaa tacaagatct | 2100 | |
| ttttcagata catttgcaga ttataagtct caatatagcg acttattttg ggattggaca | 2160 | |
| ggtgataacc caagattaag tgaaataaga ggaaaagttg ttgttttaca aaattttca | 2220 | |
| ggtggtaaat ttggtatcaa ttacaataca ttgaatactc aagatcaata tcatttaaat | 2280 | |
| acaaactggg atttatatga taaatggcta ttcgtcaaag aacatttgta tgccgctgac | 2340 | |
| aactcttata aaagtggccg taaacaagta tatctgaatt acctaagtgg atcaggtggt | 2400 | |
| tcatttcctt attttgttgc aagtggacat agtagtccag gtacagatgc tccacaatta | 2460 | |
| tctacaggtc taacaacacc agcatttgca agctggtatc cggattttcc acggggaagt | 2520 | |
| tgttttatag gaatttgcac aatttacttt gaaggaacaa atattcttac aagtcagtgg | 2580 | |
| atagagaaaa atgattttaa atatatagga atcatagctg ctgattttcc aggaagaaca | 2640 | |
| ttaatttcca atattattag tctgaataaa cttcttagct tagaaattaa aaatggtggt | 2700 | |
| acctatcaaa ttgtttccgc tttaaataat agtagtgtta tagatatgag tctgagtgga | 2760 | |
| gatcgaaatg ttcacctatg gtccaataac ggtactctta tcaagtatg gaaattcgtg | 2820 | |
| tatgattcaa atagattggc ataccaaatt aaaagtctat ccgatgaaaa tttagtacta | 2880 | |
| acttgggctt attatagtag taatcgagat aatgtaattg ttgcttctaa tcaaaatagc | 2940 | |
| gatgagcaat attggatacc tgagcgcaca ggcgcatatc attatttttaa aaatctcatc | 3000 | |
| aatccctcgg gagcattaga tgtaagcgga tcaggaacaa caaacggaac gaatattttg | 3060 | |
| tattggagtt ataacagagc aacgaatcaa aaattcaaac tggaagaagt aaatatacct | 3120 | |
| ggaggtcaag ctgaaggtgt acttttatat gcagatgcta attatgtagg gaaatctgta | 3180 | |
| ctactaacaa atagtgtctc aaaccttaga gacgttggta tgaatgatat agccagttct | 3240 | |
| ataaaattta ttggtcctta tcaagctact ctatatgaac atgataattt tacaggtgcg | 3300 | |
| gcttttactc tcacatctaa tgttgcaaat ttaaagatg ttggcatgaa tgatacagtt | 3360 | |
| agttctataa aaattacaaa gacatctgga ggccgagcta caggtatata tttatatgca | 3420 | |
| gatgctaatt atgtaggcag atctgtatgg ttaacatcta atgttgcaaa tttaaaagat | 3480 | |
| attggcatga atgatacagt cagttctgta gaaattgttg gcgcatatca agccacttta | 3540 | |
| tatggggatg ccaattatac agggaaggct tataatctca ctcataatgt tacaaattta | 3600 | |
| aaagatgttg gcatgaatga tatagtcagt tccataaaaa ttttagtgt gcaccaccat | 3660 | |
| cacgctcacc atcactga | 3678 | |

<210> SEQ ID NO 22
<211> LENGTH: 1225
<212> TYPE: PRT
<213> ORGANISM: Artificial
<220> FEATURE:
<223> OTHER INFORMATION: The amino acid sequence of TIC4747_His.

<400> SEQUENCE: 22

Met Asp Gln Lys Ile Ile Lys Met Arg Glu Ala Val Asn Ala Leu Phe
1               5                   10                  15

Ser Asn Asn His Leu Lys Leu Asn Ile Thr Asp Tyr Asn Ile Asp Gln
                20                  25                  30

Thr Ala Tyr Leu Val Asp Ser Met Ser Asp Asp Ala Tyr Arg Gln Glu
        35                  40                  45

```
Lys Met Met Phe Leu Asp Gln Ile Lys Phe Ala Lys Arg Leu Ser Gln
    50                  55                  60

Lys Arg Asn Leu Leu Asn His Gly Asp Phe Glu Gly Ser Asn Trp Thr
65                  70                  75                  80

Gly Lys Asn Gly Trp Lys Arg Asn Asn Tyr Val Val Ala Ser Asp
                85                  90                  95

His Pro Ile Phe Lys Gly Arg Tyr Leu His Ile Pro Gly Ala Thr Thr
            100                 105                 110

Ala Met Ser Gly Ala Ile Ile Pro Thr Tyr Val Tyr Gln Ser Ile Asp
        115                 120                 125

Glu Ser Lys Leu Lys Pro Tyr Thr Arg Tyr Leu Val Arg Gly Phe Val
130                 135                 140

Gly Lys Ser Gln Asp Leu Ala Leu Leu Val Ser Arg Tyr Thr Lys Glu
145                 150                 155                 160

Val Tyr Lys Lys Ile Asn Val Pro Asn Asp Lys Asp Tyr Asp Met Thr
                165                 170                 175

Ser His Ile Asn Arg Glu Glu Asn Leu Trp His Asn Arg Tyr Ile Lys
            180                 185                 190

Asp Thr Ser Val Gln Asn Ser Ile Ser Met Cys Lys Asn Pro His Glu
        195                 200                 205

Phe Thr Cys His Ile Asp Ile Gly Glu Leu Asp Arg Lys Lys Gly Pro
210                 215                 220

Gly Ile Thr Ile Gly Phe Gln Ile Gly Thr Thr Asp Gly Met Ala Thr
225                 230                 235                 240

Leu Asp Asn Ile Glu Val Ile Glu Ala His Pro Leu Thr Gly Tyr Ala
                245                 250                 255

Leu Ala Arg Ile Glu Lys Arg Glu Arg Lys Trp Lys Gln Lys Trp Leu
            260                 265                 270

Glu His Arg Ile Gln Ile Glu Lys Ala Val Gln Thr Ala Gln Glu Val
        275                 280                 285

Ile Arg Asn Leu Phe Thr Cys Pro Gln Gln Asn Gln Leu Asn Trp Met
290                 295                 300

Thr Thr Arg Asn Asp Ile Ala His Ala Glu Thr Leu Ile Lys Glu Ile
305                 310                 315                 320

Ser Tyr Arg Tyr Ser Gln Leu Ser Cys Gly Asp Phe Pro Ile Leu Pro
                325                 330                 335

Glu Glu Ala Tyr Asp Ile Leu Gln Gln Leu Ser Thr Ala Val Glu Thr
            340                 345                 350

Ala Lys Ala Leu Tyr Thr Gln Arg Asn Val Val Asn Asn Gly Asp Phe
        355                 360                 365

Gln Ala Gly Leu Ser Asn Trp His Arg Thr Asp Gly Ala Glu Ile Gln
370                 375                 380

Gln Ile Gln Asn Ala Ser Ser Val Leu Ile Ile Thr Asp Trp Ala Ala
385                 390                 395                 400

Asn Ile Ser Gln Asp Met Arg Val Val Glu Lys Gly Ser Tyr Leu Leu
                405                 410                 415

Arg Val Thr Ala Lys Lys Glu Asp Ala Gly Glu Gly Tyr Ile Thr Ile
            420                 425                 430

Ser Asp Cys Ala Ala Leu Ile Glu Thr Leu Thr Phe Thr Thr Gly Glu
        435                 440                 445

Ser Val Glu Ser Leu Thr His Ser Asp Ile His Ser Arg Leu His Lys
450                 455                 460

Arg Tyr Asn Lys Lys His Ile Lys Asn His Pro Ser Glu Glu Tyr Glu
```

-continued

```
465                 470                 475                 480
Ile Glu Ser Asp Leu His Leu Phe Asn Arg Ala Glu Gln Asn Gly Ser
                485                 490                 495
Leu Pro Ser Ser Tyr Val Thr Lys Thr Met Glu Ile Phe Pro Glu Thr
                500                 505                 510
Asn Arg Val Arg Ile Glu Ile Gly Glu Thr Gly Gly Thr Phe Ile Val
                515                 520                 525
Glu Ser Val Glu Leu Ile Arg Met Glu Gln Met Asn Glu Thr Asn Asn
530                 535                 540
Pro Asp Val Asp Val Gln Ile Val Met Asn Asp Thr Pro Ala Thr Gln
545                 550                 555                 560
Phe Asp Pro Val Ser Phe Thr Glu Ser Thr Val Arg Pro Arg Asn Ala
                565                 570                 575
Gln Tyr Ala Tyr Ser His Asp Ser Asn Ile Gly Tyr Glu Asn Pro Asn
                580                 585                 590
Trp Met Ala Asp Ile Ser Gly Asp Thr Leu Phe Thr Asp Leu Ser Ile
                595                 600                 605
Pro Gly Thr His Asn Thr Met Ala Leu Tyr Gly Gly Asp Ile Thr Gln
                610                 615                 620
Cys Gln Thr Met Ser Leu Asn Thr Gln Leu His Val Gly Ile Arg Tyr
625                 630                 635                 640
Leu Asp Ile Arg Cys Arg His Ile Glu Asn Ala Phe Ala Ile His His
                645                 650                 655
Gly Pro Val Tyr Gln Asn Ala Met Phe Gly Asp Val Cys Ile Ala Val
                660                 665                 670
Arg Asn Phe Leu Arg Ser Asn Pro Ser Glu Thr Val Phe Met Arg Ile
                675                 680                 685
Lys Glu Glu His Thr Ala Glu Asn Asn Thr Arg Ser Phe Ser Asp Thr
                690                 695                 700
Phe Ala Asp Tyr Lys Ser Gln Tyr Ser Asp Leu Phe Trp Asp Trp Thr
705                 710                 715                 720
Gly Asp Asn Pro Arg Leu Ser Glu Ile Arg Gly Lys Val Val Leu
                725                 730                 735
Gln Asn Phe Ser Gly Gly Lys Phe Gly Ile Asn Tyr Asn Thr Leu Asn
                740                 745                 750
Thr Gln Asp Gln Tyr His Leu Asn Thr Asn Trp Asp Leu Tyr Asp Lys
                755                 760                 765
Trp Leu Phe Val Lys Glu His Leu Tyr Ala Ala Asp Asn Ser Tyr Lys
770                 775                 780
Ser Gly Arg Lys Gln Val Tyr Leu Asn Tyr Leu Ser Gly Ser Gly Gly
785                 790                 795                 800
Ser Phe Pro Tyr Phe Val Ala Ser Gly His Ser Ser Pro Gly Thr Asp
                805                 810                 815
Ala Pro Gln Leu Ser Thr Gly Leu Thr Thr Pro Ala Phe Ala Ser Trp
                820                 825                 830
Tyr Pro Asp Phe Pro Arg Gly Ser Cys Phe Ile Gly Ile Cys Thr Ile
                835                 840                 845
Tyr Phe Glu Gly Thr Asn Ile Leu Thr Ser Gln Trp Ile Glu Lys Asn
                850                 855                 860
Asp Phe Lys Tyr Ile Gly Ile Ile Ala Ala Asp Phe Pro Gly Arg Thr
865                 870                 875                 880
Leu Ile Ser Asn Ile Ile Ser Leu Asn Lys Leu Leu Ser Leu Glu Ile
                885                 890                 895
```

Lys Asn Gly Gly Thr Tyr Gln Ile Val Ser Ala Leu Asn Asn Ser Ser
            900                 905                 910

Val Ile Asp Met Ser Leu Ser Gly Asp Arg Asn Val His Leu Trp Ser
        915                 920                 925

Asn Asn Gly Thr Leu Asn Gln Val Trp Lys Phe Val Tyr Asp Ser Asn
    930                 935                 940

Arg Leu Ala Tyr Gln Ile Lys Ser Leu Ser Asp Glu Asn Leu Val Leu
945                 950                 955                 960

Thr Trp Ala Tyr Tyr Ser Ser Asn Arg Asp Asn Val Ile Val Ala Ser
                965                 970                 975

Asn Gln Asn Ser Asp Glu Gln Tyr Trp Ile Pro Glu Arg Thr Gly Ala
            980                 985                 990

Tyr His Tyr Phe Lys Asn Leu Ile Asn Pro Ser Gly Ala Leu Asp Val
        995                 1000                1005

Ser Gly Ser Gly Thr Thr Asn Gly Thr Asn Ile Leu Tyr Trp Ser
    1010                1015                1020

Tyr Asn Arg Ala Thr Asn Gln Lys Phe Lys Leu Glu Glu Val Asn
    1025                1030                1035

Ile Pro Gly Gly Gln Ala Glu Gly Val Leu Leu Tyr Ala Asp Ala
    1040                1045                1050

Asn Tyr Val Gly Lys Ser Val Leu Leu Thr Asn Ser Val Ser Asn
    1055                1060                1065

Leu Arg Asp Val Gly Met Asn Asp Ile Ala Ser Ser Ile Lys Phe
    1070                1075                1080

Ile Gly Pro Tyr Gln Ala Thr Leu Tyr Glu His Asp Asn Phe Thr
    1085                1090                1095

Gly Ala Ala Phe Thr Leu Thr Ser Asn Val Ala Asn Leu Lys Asp
    1100                1105                1110

Val Gly Met Asn Asp Thr Val Ser Ser Ile Lys Ile Thr Lys Thr
    1115                1120                1125

Ser Gly Gly Arg Ala Thr Gly Ile Tyr Leu Tyr Ala Asp Ala Asn
    1130                1135                1140

Tyr Val Gly Arg Ser Val Trp Leu Thr Ser Asn Val Ala Asn Leu
    1145                1150                1155

Lys Asp Ile Gly Met Asn Asp Thr Val Ser Ser Val Glu Ile Val
    1160                1165                1170

Gly Ala Tyr Gln Ala Thr Leu Tyr Gly Asp Ala Asn Tyr Thr Gly
    1175                1180                1185

Lys Ala Tyr Asn Leu Thr His Asn Val Thr Asn Leu Lys Asp Val
    1190                1195                1200

Gly Met Asn Asp Ile Val Ser Ser Ile Lys Ile Phe Ser Val His
    1205                1210                1215

His His His Ala His His His
    1220                1225

<210> SEQ ID NO 23
<211> LENGTH: 3714
<212> TYPE: DNA
<213> ORGANISM: Artificial
<220> FEATURE:
<223> OTHER INFORMATION: A nucleotide sequence encoding TIC4904_His
      comprised of a histidine tag coding sequence operably linked 5' to
      the TIC4904 coding sequence.

<400> SEQUENCE: 23

-continued

```
atgcatcacc atcaccatca ccatcaccat cacggtaccg agaccgtccg cttccaatcc    60
atggatcaaa agattataaa aatgcgagaa gcagtcaatg ccttgttttc caataatcag   120
ttaaaattga atattactga ttacaatata gatcagattg cataccttgt tgatagtatg   180
tctgatgacg catatcgaca agaaaaaatg aggtttctcg atcaaatcaa atttgcaaag   240
cgcttgagtc aaaaacgcaa cctgttgaat tatggagatt ttgaaggatc caattggcca   300
ggtaagaatg gatggaaaag aataattat gtagttgtcg catcggatca tcctatattt   360
aaaggccgat atttacacat accaagtgca acaaccacga tgagtggcgc aatcattccg   420
acttatgtat atcaacgtat agatgaatcg aagttaaaac cgtatacacg ttatttggta   480
cgagggtatg ttggaaagag tcaagattta gcgttacttg tttcccggta taccaaagaa   540
gtgtacaaga aaatcaatgt accaaatgat gaagattacg atatcacatc gcatataaat   600
agggaagaga atctatggca caatagatat ataagaggca cccaggttca aaattcaatc   660
tctatgtgca acaatccaca tgaatttacg tgtcatattg atataggga actggataga   720 aagaaaggtc ctggtataac catcggtttt caaattggaa caacagatgg gatggcaaca   780
ttagataata tagaagtgat agaagcacat ccgttaactg gatcggcctt agcacgtatc   840
gaaaaacgtg aacgtaaatg gaaacaaaaa tggctagaga atcaaataca aatcgaaaag   900
gctgtgcaaa cagtgcaaga ggtgattcga aatttattta catgcccaca acaaaatcaa   960
ttgaactgga tgacaacccg aaacgacatt gcacatgcag aaacattgat aaaagagatt  1020
ccatatcggt atagtcaact ttcttgtgga gatttcccca tactaccaga gaggcatat  1080 gacatccttc aacaactttc aactgcagtt gaaaccgcaa aaacgttgta tacacagcga  1140
aatgtggtga agaatgggga ttttcaagct ggattatcaa attggcatag gacagatggt  1200
gcagagatac aacaaattca gaatacatcc tctgttctgg taattacaga ctgggctgcg  1260
aatatttcac aagacatgcg tgtagttgaa aaaggtggat atctgttgcg cgtaacagcg  1320
aaaaaagaaa atccgggaga aggttatata actattagtg attgtgccgc attgacagaa  1380
acactgaaat ttacagcggg ggaatctgta gaaagtctga cacattctga tatttattca  1440
aggctccata agcgctctga taagaacaa ataacaaacc atctttcaaa agaatatgaa  1500
atagaatcgg atcctcattt attaaatagg gcagaacaaa atggttctct ccctttttagc  1560 tatgtaacca aaacaattga aattttccg gaaaccaatc gagtacgcat tgaaattgga  1620
gaaacaggtg gaacatttat agtggaaagt gtggaattga ttcaaatgga acaggtaaac  1680
gaaacaaaca atccaactgt agatgttcaa attgtaatga atgatacacc cgctacaaaa  1740
tttaatccag tttcttttac agaatcaacg gtgagtccta gaactgttca ttatgcgtat  1800
tcacatgatt caagtatagg ttatgaaaac cctaactgga tggatgatat ttcaggtgat  1860 actttatta gtgatttatc tctccctggt acacataata caatggctct ttatggagga  1920
gatattacac aatgccaaac gatgtcactg agtacgcaat tacaagtagg aattcgttat  1980
ttagatattc gctgtaggca catagaaaat gttttgcta ttcatcatgg acctgtgtac  2040
caaaatgcga tgtttggaga tgtttgtatt gccgtaagga attttttgaa aagcaaccct  2100
agtgaaacag tatttatgcg gattaaagaa gaacatacag cagaaaacaa tacaagatct  2160
ttttcagata catttgcaga ttataagtct caatatagcg acttatttg ggattggaca  2220 ggtgataatc caagattaag tgaaataaga ggaaagttg ttgttttgca aaatttata  2280 ggtgctaaat ttggtatcca ttacgataca ttgaataaac aagatcaata tcatttaaat  2340
acaaactggg atttatatga taatggata ttcgtcaaag aacatttgta tgccgctgac  2400
```

```
aactcttata aaagtggccg taaacaagta tatctgaatt acctaagtgg atcaggtggt   2460
tcatttcctt attttgttgc aagtggacat agtagtccag gtacagatgc tccacaatta   2520
tctacaggtc taacaacacc agcatttgca agctggtatc cggattttcc acggggaagt   2580
tgttttatag gaatttgcac aatttacttt gaaggaacaa atattcttac aagtcagtgg   2640
atagagaaaa atgattttaa atatatagga atcatagctg ctgattttcc aggaagaaca   2700
ttaatttcca atattattag tctgaataaa cttcttagct tagaaattaa aaatggtggt   2760
acctatcaaa ttgtttccgc tttaaataat agtagtgtta tagatatgag tctgagtgga   2820
gatcgaaatg ttcacctatg gtccaataac ggtactctta atcaagtatg gaaattcgtg   2880
tatgattcaa atagattagc atatcaaatt aaaagtctat ccgatgaaaa tttagtacta   2940
acttgggctt attatagtag taatcgagat aatgtaattg ttgcttctaa tcaaaatagc   3000
gatgagcaat attggatacc tgagcgcaca ggcgcatatc attattttaa aaatctcatc   3060
aatccctcgg gagcattaga tgtaagcgga tcaggaacaa caaacggaac gaatattttg   3120
tattggagtt ataacagagc aacgaatcaa aaattcaaac tggaagaagt aaatatacct   3180
ggaggtcaag ctgaaggtgt acttttatat gcagatgcta attatgtagg gaaatctgta   3240
ctactaacaa atagtgtctc aaaccttaga gacgttggta tgaatgatat agccagttct   3300
ataaaattta ttggtcctta tcaagctact ctatatgaac atgataattt tacaggtgcg   3360 gttttactc ccacatctaa tgttgcaaat ttaaaagatg ttggcatgaa tgatacagtt   3420
agttccataa aaattacaaa gacatctgga ggccgagcta caggtatata tttatatgca   3480
gatgctaatt atgtaggcag atctgtatgg ttaacatcaa atgttgcaaa tttaaaagat   3540
gttggcatga atgatacagt cagttctgta gaaattgttg gcgcgtatca ggccacttta   3600 tatgggatt ccaattatac agggaaggct tataatctca ctcataatgt tgcaaattta   3660
aaagatgttg gcatgaatga tatagtcagt tccataaaaa ttttagtgt gtaa          3714
```

<210> SEQ ID NO 24
<211> LENGTH: 1237
<212> TYPE: PRT
<213> ORGANISM: Artificial
<220> FEATURE:
<223> OTHER INFORMATION: The amino acid sequence of TIC4904_His.

<400> SEQUENCE: 24

```
Met His His His His His His His His Gly Thr Glu Thr Val
1               5                   10                  15

Arg Phe Gln Ser Met Asp Gln Lys Ile Ile Lys Met Arg Glu Ala Val
            20                  25                  30

Asn Ala Leu Phe Ser Asn Asn Gln Leu Lys Leu Asn Ile Thr Asp Tyr
        35                  40                  45

Asn Ile Asp Gln Ile Ala Tyr Leu Val Asp Ser Met Ser Asp Asp Ala
    50                  55                  60

Tyr Arg Gln Glu Lys Met Arg Phe Leu Asp Gln Ile Lys Phe Ala Lys
65                  70                  75                  80

Arg Leu Ser Gln Lys Arg Asn Leu Leu Asn Tyr Gly Asp Phe Glu Gly
                85                  90                  95

Ser Asn Trp Pro Gly Lys Asn Gly Trp Lys Arg Asn Asn Tyr Val Val
            100                 105                 110

Val Ala Ser Asp His Pro Ile Phe Lys Gly Arg Tyr Leu His Ile Pro
        115                 120                 125
```

```
Ser Ala Thr Thr Thr Met Ser Gly Ala Ile Ile Pro Thr Tyr Val Tyr
    130                 135                 140
Gln Arg Ile Asp Glu Ser Lys Leu Lys Pro Tyr Thr Arg Tyr Leu Val
145                 150                 155                 160
Arg Gly Tyr Val Gly Lys Ser Gln Asp Leu Ala Leu Leu Val Ser Arg
                165                 170                 175
Tyr Thr Lys Glu Val Tyr Lys Lys Ile Asn Val Pro Asn Asp Glu Asp
            180                 185                 190
Tyr Asp Ile Thr Ser His Ile Asn Arg Glu Glu Asn Leu Trp His Asn
        195                 200                 205
Arg Tyr Ile Arg Gly Thr Gln Val Gln Asn Ser Ile Ser Met Cys Asn
    210                 215                 220
Asn Pro His Glu Phe Thr Cys His Ile Asp Ile Gly Glu Leu Asp Arg
225                 230                 235                 240
Lys Lys Gly Pro Gly Ile Thr Ile Gly Phe Gln Ile Gly Thr Thr Asp
                245                 250                 255
Gly Met Ala Thr Leu Asp Asn Ile Glu Val Ile Glu Ala His Pro Leu
            260                 265                 270
Thr Gly Ser Ala Leu Ala Arg Ile Glu Lys Arg Glu Arg Lys Trp Lys
        275                 280                 285
Gln Lys Trp Leu Glu Asn Gln Ile Gln Ile Glu Lys Ala Val Gln Thr
    290                 295                 300
Val Gln Glu Val Ile Arg Asn Leu Phe Thr Cys Pro Gln Gln Asn Gln
305                 310                 315                 320
Leu Asn Trp Met Thr Thr Arg Asn Asp Ile Ala His Ala Glu Thr Leu
                325                 330                 335
Ile Lys Glu Ile Pro Tyr Arg Tyr Ser Gln Leu Ser Cys Gly Asp Phe
            340                 345                 350
Pro Ile Leu Pro Glu Glu Ala Tyr Asp Ile Leu Gln Gln Leu Ser Thr
        355                 360                 365
Ala Val Glu Thr Ala Lys Thr Leu Tyr Thr Gln Arg Asn Val Val Lys
    370                 375                 380
Asn Gly Asp Phe Gln Ala Gly Leu Ser Asn Trp His Arg Thr Asp Gly
385                 390                 395                 400
Ala Glu Ile Gln Gln Ile Gln Asn Thr Ser Ser Val Leu Val Ile Thr
                405                 410                 415
Asp Trp Ala Ala Asn Ile Ser Gln Asp Met Arg Val Val Glu Lys Gly
            420                 425                 430
Gly Tyr Leu Leu Arg Val Thr Ala Lys Lys Glu Asn Pro Gly Glu Gly
        435                 440                 445
Tyr Ile Thr Ile Ser Asp Cys Ala Ala Leu Thr Glu Thr Leu Lys Phe
    450                 455                 460
Thr Ala Gly Glu Ser Val Glu Ser Leu Thr His Ser Asp Ile Tyr Ser
465                 470                 475                 480
Arg Leu His Lys Arg Ser Asp Lys Glu Gln Ile Thr Asn His Leu Ser
                485                 490                 495
Lys Glu Tyr Glu Ile Glu Ser Asp Pro His Leu Leu Asn Arg Ala Glu
            500                 505                 510
Gln Asn Gly Ser Leu Pro Phe Ser Tyr Val Thr Lys Thr Ile Glu Ile
        515                 520                 525
Phe Pro Glu Thr Asn Arg Val Arg Ile Glu Ile Gly Glu Thr Gly Gly
530                 535                 540
Thr Phe Ile Val Glu Ser Val Glu Leu Ile Gln Met Glu Gln Val Asn
```

```
545                 550                 555                 560
Glu Thr Asn Asn Pro Thr Val Asp Val Gln Ile Val Met Asn Asp Thr
                565                 570                 575

Pro Ala Thr Lys Phe Asn Pro Val Ser Phe Thr Glu Ser Thr Val Ser
                580                 585                 590

Pro Arg Thr Val His Tyr Ala Tyr Ser His Asp Ser Ser Ile Gly Tyr
                595                 600                 605

Glu Asn Pro Asn Trp Met Asp Asp Ile Ser Gly Asp Thr Leu Phe Ser
610                 615                 620

Asp Leu Ser Leu Pro Gly Thr His Asn Thr Met Ala Leu Tyr Gly Gly
625                 630                 635                 640

Asp Ile Thr Gln Cys Gln Thr Met Ser Leu Ser Thr Gln Leu Gln Val
                645                 650                 655

Gly Ile Arg Tyr Leu Asp Ile Arg Cys Arg His Ile Glu Asn Val Phe
                660                 665                 670

Ala Ile His His Gly Pro Val Tyr Gln Asn Ala Met Phe Gly Asp Val
                675                 680                 685

Cys Ile Ala Val Arg Asn Phe Leu Lys Ser Asn Pro Ser Glu Thr Val
                690                 695                 700

Phe Met Arg Ile Lys Glu Glu His Thr Ala Glu Asn Asn Thr Arg Ser
705                 710                 715                 720

Phe Ser Asp Thr Phe Ala Asp Tyr Lys Ser Gln Tyr Ser Asp Leu Phe
                725                 730                 735

Trp Asp Trp Thr Gly Asp Asn Pro Arg Leu Ser Glu Ile Arg Gly Lys
                740                 745                 750

Val Val Val Leu Gln Asn Phe Ile Gly Ala Lys Phe Gly Ile His Tyr
                755                 760                 765

Asp Thr Leu Asn Lys Gln Asp Gln Tyr His Leu Asn Thr Asn Trp Asp
                770                 775                 780

Leu Tyr Asp Lys Trp Ile Phe Val Lys Glu His Leu Tyr Ala Ala Asp
785                 790                 795                 800

Asn Ser Tyr Lys Ser Gly Arg Lys Gln Val Tyr Leu Asn Tyr Leu Ser
                805                 810                 815

Gly Ser Gly Gly Ser Phe Pro Tyr Phe Val Ala Ser Gly His Ser Ser
                820                 825                 830

Pro Gly Thr Asp Ala Pro Gln Leu Ser Thr Gly Leu Thr Thr Pro Ala
                835                 840                 845

Phe Ala Ser Trp Tyr Pro Asp Phe Pro Arg Gly Ser Cys Phe Ile Gly
                850                 855                 860

Ile Cys Thr Ile Tyr Phe Glu Gly Thr Asn Ile Leu Thr Ser Gln Trp
865                 870                 875                 880

Ile Glu Lys Asn Asp Phe Lys Tyr Ile Gly Ile Ala Ala Asp Phe
                885                 890                 895

Pro Gly Arg Thr Leu Ile Ser Asn Ile Ser Leu Asn Lys Leu Leu
                900                 905                 910

Ser Leu Glu Ile Lys Asn Gly Gly Thr Tyr Gln Ile Val Ser Ala Leu
                915                 920                 925

Asn Asn Ser Ser Val Ile Asp Met Ser Leu Ser Gly Asp Arg Asn Val
                930                 935                 940

His Leu Trp Ser Asn Asn Gly Thr Leu Asn Gln Val Trp Lys Phe Val
945                 950                 955                 960

Tyr Asp Ser Asn Arg Leu Ala Tyr Gln Ile Lys Ser Leu Ser Asp Glu
                965                 970                 975
```

```
Asn Leu Val Leu Thr Trp Ala Tyr Tyr Ser Ser Asn Arg Asp Asn Val
            980                 985                 990

Ile Val Ala Ser Asn Gln Asn Ser Asp Glu Gln Tyr Trp Ile Pro Glu
        995                1000                1005

Arg Thr Gly Ala Tyr His Tyr Phe Lys Asn Leu Ile Asn Pro Ser
    1010                1015                1020

Gly Ala Leu Asp Val Ser Gly Ser Gly Thr Thr Asn Gly Thr Asn
    1025                1030                1035

Ile Leu Tyr Trp Ser Tyr Asn Arg Ala Thr Asn Gln Lys Phe Lys
    1040                1045                1050

Leu Glu Glu Val Asn Ile Pro Gly Gly Gln Ala Glu Gly Val Leu
    1055                1060                1065

Leu Tyr Ala Asp Ala Asn Tyr Val Gly Lys Ser Val Leu Leu Thr
    1070                1075                1080

Asn Ser Val Ser Asn Leu Arg Asp Val Gly Met Asn Asp Ile Ala
    1085                1090                1095

Ser Ser Ile Lys Phe Ile Gly Pro Tyr Gln Ala Thr Leu Tyr Glu
    1100                1105                1110

His Asp Asn Phe Thr Gly Ala Val Phe Thr Pro Thr Ser Asn Val
    1115                1120                1125

Ala Asn Leu Lys Asp Val Gly Met Asn Asp Thr Val Ser Ser Ile
    1130                1135                1140

Lys Ile Thr Lys Thr Ser Gly Gly Arg Ala Thr Gly Ile Tyr Leu
    1145                1150                1155

Tyr Ala Asp Ala Asn Tyr Val Gly Arg Ser Val Trp Leu Thr Ser
    1160                1165                1170

Asn Val Ala Asn Leu Lys Asp Val Gly Met Asn Asp Thr Val Ser
    1175                1180                1185

Ser Val Glu Ile Val Gly Ala Tyr Gln Ala Thr Leu Tyr Gly Asp
    1190                1195                1200

Ser Asn Tyr Thr Gly Lys Ala Tyr Asn Leu Thr His Asn Val Ala
    1205                1210                1215

Asn Leu Lys Asp Val Gly Met Asn Asp Ile Val Ser Ser Ile Lys
    1220                1225                1230

Ile Phe Ser Val
    1235

<210> SEQ ID NO 25
<211> LENGTH: 3696
<212> TYPE: DNA
<213> ORGANISM: Artificial
<220> FEATURE:
<223> OTHER INFORMATION: A nucleotide sequence encoding TIC6547_His
      comprised of a histidine tag coding sequence operably linked 5' to
      the TIC6547 coding sequence.

<400> SEQUENCE: 25
atgcatcacc atcaccatca ccatcaccat cacggtaccg agaccgtccg cttccaatcc      60
atggatcaaa agattataaa aatgcgagaa gcagtcaatg ccttgttttc caataatcag     120
ttaaaattga atattactga ttacaatata gatcagattg cataccttgt tgatagtatg     180
tctgatgacg catatcgaca agaaaaaatg aggtttctcg atcaaatcaa atttgcaaag    240
cgcttgagtc aaaaacgcaa cctgttgaat tatggagatt ttgaaggatc caattggcca    300
ggtaagaatg gatggaaaag aaataattat gtagttgtcg catcggatca tcctatattt    360
```

```
aaaggccgat atttacacat accaagtgca acaaccacga tgagtggcgc aatcattccg    420
acttatgtat atcaacgtat agatgaatcg aagttaaaac cgtatacacg ttatttggta    480
cgagggtatg ttggaaagag tcaagattta gcgttacttg tttcccggta taccaaagaa    540
gtgtacaaga aaatcaatgt accaaatgat gaggattacg atatcacatc gcatataaat    600
agggaagaga atttatggca caatagatat ataagaggca cccaagttca aaattcaatc    660
tctatgtgca acaatccaca tgaatttacg tgtcatattg ataggaga actggatga      720 aagaaaggtc ctggtataac catcggtttt caaattggaa caacagatgg gatggcaaca    780
ttagataata tagaagtgat agaagcacat ccgttaactg atcggcctt agcacgtatc     840 caaaaacgtg aacgtaaatg aaacaaaaa tggatagaga atcgaatgca aatcgaaaag    900
gctgtacaaa cagcgcaaga ggtgattcga aatttattta catgcccaca acaaaatcaa    960
ttgaactgga tgacaactcg aaacgacatt acacatgcag aaacattgat aaaagagatt   1020
ccatatcggt atagccaact ttcttgtgga gatttcccca cactaccaga agaggcgtat   1080
gacatccttc aacaactttc aactgcagtt gaaaccgcaa aagcgttata tgcacaacga   1140
aatgtggtga ataatgggga ttttcaagct ggattatcga attggtatac gacagatggt   1200
gcagagatac aacaaataca gaattcgtcc tctgttctag taattaaaga ctgggctaca   1260
aatatttcac aggacatgcg tgtggttgaa aaggtggct atctgctacg cgtaacagcg    1320 aaaaagaag ataccggaga aggttatata acaattagtg attgtgcagc attggtagaa    1380
aaattgacat ttacaacggg ggaagctgta gaaagtctgg cacattctga tagtcgttca   1440
aggctccata agcgctatga taaaaaatca gaaggatatg aaatagaatc ggatcctcat   1500
ttatttaata gggcgaaaca aaacggttct cttccttcta gctatgtaac caaaacgatt   1560
gaaatctttc cggaaaccaa tcgagtacgc attgagattg gagaaacagg tggaaagttt   1620
atggtggaaa gtgtggaatt gattcgaatg gaacagatga acgaaacaaa taatccagct   1680
gtagatgttc aaactgtaat gaatgataca cctgctacac aatttgatcc agtttctttt   1740
acagaatcaa cggtgagtcc cagaaatgct cagtatgcgt attctcatga tacaaatata   1800
ggctatgaaa atcctaactg gatggctgat atttcaggtg atactttatt tagtgattta   1860
tctatccctg gtacacataa tacaatggct cttcatggag gagatattac acaatgtcaa   1920
acgatgtcac tgaatacaca attacatgta ggaattcgtt atttagatat tcgctgtagg   1980
catatcgata atgttttgc gattcatcat gggcctgtgt accaaaatac gatgtttgga   2040
gatgtttgta tagccgtaag ggatttttg aggaacaacc ctagtgaaac agtatttatg   2100
cggataaaag aagaacatac accagaaaat aatacaagat cttttcgga tacatttgca   2160 gattataagt ctcaatatag cgacttattt tggaattgga caggtgataa cccaagatta   2220
agtgaaataa gaggaaaagt tgttgttttg caaaactttt caggggatag gtttggtatc   2280
tactacaata cactgaatac acaagatcaa tatcatttag atacaaactg ggatttatat   2340
gataaatggc tatttgtaaa agagcatttg tataagctg acgacgctta taaaagtggt   2400
ggtaaacaag catatctgaa ttatctaagt gggtcaggtg gttctttcc ttattttgtt    2460 gcaagtggac atagtagtcc tggtacagat gctccacaat tatctacagg tctaacaaca   2520
ccagcatttg caagctggta tccggatttt ccacggggaa gttgttttat aggaatttgc   2580
acaatttact ttgaaggaac aaatattctt acaagtcagt ggatagagaa aaatgatttt   2640
aaatatatag gaatcatagc tgctgatttt ccaggaagaa cattaatttc caatattatt   2700
agtttgaata aacttcttag cttagaaatt aaaaatggtg gtacctatca aattgtttcc   2760
```

-continued

```
gctttaaata atagtagtgt tatagatatg agtctgagtg gagatcgaaa tgctcaccta    2820
tggtccaata acggtactcc taatcaagta tggaaattcg tgtatgattc aaatagatta    2880
gcataccaaa ttaaaagttt atccgatgaa aatttagtac taacttgggc ttattatagt    2940
agtaatcgag ataatgtaat tgtcgcttct aatcaaaata gcgatgagca atattggata    3000
cctgagcgca caggcgcata tcattatttt aaaaatctca tcaatccctc aggagcatta    3060
gatgtaagcg gatcaggaac aacaaacgga acgaatattt tgtattggag ttataacaga    3120
gcaacgaatc aaaaattcaa actggaagaa gtaaatatat ctggaggtca aactgaaggt    3180
gtacttttat atgcagaggc taattatgta gggaaatctg tactactaac aaatagtgtc    3240 tccaaccta gagacgttgg tatgaatgat atagctagtt ctataaaatt tattggtcct    3300
tatcaagcta ctctatatga acatgatgat tttacaggtg cggtttttac tcccacatct    3360
aatgttgcaa atttaaaaga tgttggcatg aatgatacag ttagttctat aaaaattaca    3420
aagacatctg gaggccgagc tacaggtata tatttatatg cagatgctaa ttatgtaggc    3480
agatctgtat ggttaacatc taatgttgca aatttaaaag atgttggcat gaatgataca    3540
gtcagttctg tagaaattgt tggcgcgtat caggccactt tatatgggga ttccaattat    3600
acagggaagg cttataatct cactcataat gttgcaaatt taaaagatgt tggcatgaat    3660
gatatagtca gttccataaa aatttttagt gtgtaa                               3696
```

<210> SEQ ID NO 26
<211> LENGTH: 1231
<212> TYPE: PRT
<213> ORGANISM: Artificial
<220> FEATURE:
<223> OTHER INFORMATION: The amino acid sequence of TIC6547_His.

<400> SEQUENCE: 26

```
Met His His His His His His His His Gly Thr Glu Thr Val
1               5                   10                  15

Arg Phe Gln Ser Met Asp Gln Lys Ile Ile Lys Met Arg Glu Ala Val
            20                  25                  30

Asn Ala Leu Phe Ser Asn Asn Gln Leu Lys Leu Asn Ile Thr Asp Tyr
        35                  40                  45

Asn Ile Asp Gln Ile Ala Tyr Leu Val Asp Ser Met Ser Asp Asp Ala
    50                  55                  60

Tyr Arg Gln Glu Lys Met Arg Phe Leu Asp Gln Ile Lys Phe Ala Lys
65                  70                  75                  80

Arg Leu Ser Gln Lys Arg Asn Leu Leu Asn Tyr Gly Asp Phe Glu Gly
                85                  90                  95

Ser Asn Trp Pro Gly Lys Asn Gly Trp Lys Arg Asn Asn Tyr Val Val
            100                 105                 110

Val Ala Ser Asp His Pro Ile Phe Lys Gly Arg Tyr Leu His Ile Pro
        115                 120                 125

Ser Ala Thr Thr Thr Met Ser Gly Ala Ile Ile Pro Thr Tyr Val Tyr
    130                 135                 140

Gln Arg Ile Asp Glu Ser Lys Leu Lys Pro Tyr Thr Arg Tyr Leu Val
145                 150                 155                 160

Arg Gly Tyr Val Gly Lys Ser Gln Asp Leu Ala Leu Leu Val Ser Arg
                165                 170                 175

Tyr Thr Lys Glu Val Tyr Lys Lys Ile Asn Val Pro Asn Asp Glu Asp
            180                 185                 190
```

```
Tyr Asp Ile Thr Ser His Ile Asn Arg Glu Glu Asn Leu Trp His Asn
        195                 200                 205

Arg Tyr Ile Arg Gly Thr Gln Val Gln Asn Ser Ile Ser Met Cys Asn
    210                 215                 220

Asn Pro His Glu Phe Thr Cys His Ile Asp Ile Gly Glu Leu Asp Arg
225                 230                 235                 240

Lys Lys Gly Pro Gly Ile Thr Ile Gly Phe Gln Ile Gly Thr Thr Asp
                245                 250                 255

Gly Met Ala Thr Leu Asp Asn Ile Glu Val Ile Glu Ala His Pro Leu
            260                 265                 270

Thr Gly Ser Ala Leu Ala Arg Ile Gln Lys Arg Glu Arg Lys Trp Lys
        275                 280                 285

Gln Lys Trp Ile Glu Asn Arg Met Gln Ile Glu Lys Ala Val Gln Thr
    290                 295                 300

Ala Gln Glu Val Ile Arg Asn Leu Phe Thr Cys Pro Gln Gln Asn Gln
305                 310                 315                 320

Leu Asn Trp Met Thr Thr Arg Asn Asp Ile Thr His Ala Glu Thr Leu
                325                 330                 335

Ile Lys Glu Ile Pro Tyr Arg Tyr Ser Gln Leu Ser Cys Gly Asp Phe
            340                 345                 350

Pro Thr Leu Pro Glu Glu Ala Tyr Asp Ile Leu Gln Gln Leu Ser Thr
        355                 360                 365

Ala Val Glu Thr Ala Lys Ala Leu Tyr Ala Gln Arg Asn Val Val Asn
    370                 375                 380

Asn Gly Asp Phe Gln Ala Gly Leu Ser Asn Trp Tyr Thr Thr Asp Gly
385                 390                 395                 400

Ala Glu Ile Gln Gln Ile Gln Asn Ser Ser Val Leu Val Ile Lys
                405                 410                 415

Asp Trp Ala Thr Asn Ile Ser Gln Asp Met Arg Val Val Glu Lys Gly
            420                 425                 430

Gly Tyr Leu Leu Arg Val Thr Ala Lys Lys Glu Asp Thr Gly Glu Gly
        435                 440                 445

Tyr Ile Thr Ile Ser Asp Cys Ala Ala Leu Val Glu Lys Leu Thr Phe
    450                 455                 460

Thr Thr Gly Glu Ala Val Glu Ser Leu Ala His Ser Asp Ser Arg Ser
465                 470                 475                 480

Arg Leu His Lys Arg Tyr Asp Lys Lys Ser Glu Gly Tyr Glu Ile Glu
                485                 490                 495

Ser Asp Pro His Leu Phe Asn Arg Ala Lys Gln Asn Gly Ser Leu Pro
            500                 505                 510

Ser Ser Tyr Val Thr Lys Thr Ile Glu Ile Phe Pro Glu Thr Asn Arg
        515                 520                 525

Val Arg Ile Glu Ile Gly Glu Thr Gly Gly Lys Phe Met Val Glu Ser
    530                 535                 540

Val Glu Leu Ile Arg Met Glu Gln Met Asn Glu Thr Asn Asn Pro Ala
545                 550                 555                 560

Val Asp Val Gln Thr Val Met Asn Asp Thr Pro Ala Thr Gln Phe Asp
                565                 570                 575

Pro Val Ser Phe Thr Glu Ser Thr Val Ser Pro Arg Asn Ala Gln Tyr
            580                 585                 590

Ala Tyr Ser His Asp Thr Asn Ile Gly Tyr Glu Asn Pro Asn Trp Met
        595                 600                 605

Ala Asp Ile Ser Gly Asp Thr Leu Phe Ser Asp Leu Ser Ile Pro Gly
```

```
            610                 615                 620
Thr His Asn Thr Met Ala Leu His Gly Gly Asp Ile Thr Gln Cys Gln
625                 630                 635                 640

Thr Met Ser Leu Asn Thr Gln Leu His Val Gly Ile Arg Tyr Leu Asp
                645                 650                 655

Ile Arg Cys Arg His Ile Asp Asn Val Phe Ala Ile His His Gly Pro
                660                 665                 670

Val Tyr Gln Asn Thr Met Phe Gly Asp Val Cys Ile Ala Val Arg Asp
                675                 680                 685

Phe Leu Arg Asn Asn Pro Ser Glu Thr Val Phe Met Arg Ile Lys Glu
            690                 695                 700

Glu His Thr Pro Glu Asn Asn Thr Arg Ser Phe Ser Asp Thr Phe Ala
705                 710                 715                 720

Asp Tyr Lys Ser Gln Tyr Ser Asp Leu Phe Trp Asn Trp Thr Gly Asp
                725                 730                 735

Asn Pro Arg Leu Ser Glu Ile Arg Gly Lys Val Val Leu Gln Asn
                740                 745                 750

Phe Ser Gly Asp Arg Phe Gly Ile Tyr Tyr Asn Thr Leu Asn Thr Gln
            755                 760                 765

Asp Gln Tyr His Leu Asp Thr Asn Trp Asp Leu Tyr Asp Lys Trp Leu
770                 775                 780

Phe Val Lys Glu His Leu Tyr Lys Ala Asp Asp Ala Tyr Lys Ser Gly
785                 790                 795                 800

Gly Lys Gln Ala Tyr Leu Asn Tyr Leu Ser Gly Ser Gly Ser Phe
                805                 810                 815

Pro Tyr Phe Val Ala Ser Gly His Ser Ser Pro Gly Thr Asp Ala Pro
                820                 825                 830

Gln Leu Ser Thr Gly Leu Thr Thr Pro Ala Phe Ala Ser Trp Tyr Pro
            835                 840                 845

Asp Phe Pro Arg Gly Ser Cys Phe Ile Gly Ile Cys Thr Ile Tyr Phe
850                 855                 860

Glu Gly Thr Asn Ile Leu Thr Ser Gln Trp Ile Glu Lys Asn Asp Phe
865                 870                 875                 880

Lys Tyr Ile Gly Ile Ile Ala Ala Asp Phe Pro Gly Arg Thr Leu Ile
                885                 890                 895

Ser Asn Ile Ile Ser Leu Asn Lys Leu Leu Ser Leu Glu Ile Lys Asn
                900                 905                 910

Gly Gly Thr Tyr Gln Ile Val Ser Ala Leu Asn Asn Ser Ser Val Ile
                915                 920                 925

Asp Met Ser Leu Ser Gly Asp Arg Asn Ala His Leu Trp Ser Asn Asn
930                 935                 940

Gly Thr Pro Asn Gln Val Trp Lys Phe Val Tyr Asp Ser Asn Arg Leu
945                 950                 955                 960

Ala Tyr Gln Ile Lys Ser Leu Ser Asp Glu Asn Leu Val Leu Thr Trp
                965                 970                 975

Ala Tyr Tyr Ser Ser Asn Arg Asp Asn Val Ile Val Ala Ser Asn Gln
                980                 985                 990

Asn Ser Asp Glu Gln Tyr Trp Ile Pro Glu Arg Thr Gly Ala Tyr His
            995                 1000                1005

Tyr Phe Lys Asn Leu Ile Asn Pro Ser Gly Ala Leu Asp Val Ser
    1010                1015                1020

Gly Ser Gly Thr Thr Asn Gly Thr Asn Ile Leu Tyr Trp Ser Tyr
    1025                1030                1035
```

| Asn | Arg | Ala | Thr | Asn | Gln | Lys | Phe | Lys | Leu | Glu | Glu | Val | Asn | Ile |
|---|---|---|---|---|---|---|---|---|---|---|---|---|---|---|
| | 1040 | | | | 1045 | | | | 1050 | | | | | |

| Ser | Gly | Gly | Gln | Thr | Glu | Gly | Val | Leu | Leu | Tyr | Ala | Glu | Ala | Asn |
|---|---|---|---|---|---|---|---|---|---|---|---|---|---|---|
| 1055 | | | | | 1060 | | | | | 1065 | | | | |

| Tyr | Val | Gly | Lys | Ser | Val | Leu | Leu | Thr | Asn | Ser | Val | Ser | Asn | Leu |
|---|---|---|---|---|---|---|---|---|---|---|---|---|---|---|
| 1070 | | | | | 1075 | | | | | 1080 | | | | |

| Arg | Asp | Val | Gly | Met | Asn | Asp | Ile | Ala | Ser | Ser | Ile | Lys | Phe | Ile |
|---|---|---|---|---|---|---|---|---|---|---|---|---|---|---|
| 1085 | | | | | 1090 | | | | | 1095 | | | | |

| Gly | Pro | Tyr | Gln | Ala | Thr | Leu | Tyr | Glu | His | Asp | Asp | Phe | Thr | Gly |
|---|---|---|---|---|---|---|---|---|---|---|---|---|---|---|
| 1100 | | | | | 1105 | | | | | 1110 | | | | |

| Ala | Val | Phe | Thr | Pro | Thr | Ser | Asn | Val | Ala | Asn | Leu | Lys | Asp | Val |
|---|---|---|---|---|---|---|---|---|---|---|---|---|---|---|
| 1115 | | | | | 1120 | | | | | 1125 | | | | |

| Gly | Met | Asn | Asp | Thr | Val | Ser | Ser | Ile | Lys | Ile | Thr | Lys | Thr | Ser |
|---|---|---|---|---|---|---|---|---|---|---|---|---|---|---|
| 1130 | | | | | 1135 | | | | | 1140 | | | | |

| Gly | Gly | Arg | Ala | Thr | Gly | Ile | Tyr | Leu | Tyr | Ala | Asp | Ala | Asn | Tyr |
|---|---|---|---|---|---|---|---|---|---|---|---|---|---|---|
| 1145 | | | | | 1150 | | | | | 1155 | | | | |

| Val | Gly | Arg | Ser | Val | Trp | Leu | Thr | Ser | Asn | Val | Ala | Asn | Leu | Lys |
|---|---|---|---|---|---|---|---|---|---|---|---|---|---|---|
| 1160 | | | | | 1165 | | | | | 1170 | | | | |

| Asp | Val | Gly | Met | Asn | Asp | Thr | Val | Ser | Ser | Val | Glu | Ile | Val | Gly |
|---|---|---|---|---|---|---|---|---|---|---|---|---|---|---|
| 1175 | | | | | 1180 | | | | | 1185 | | | | |

| Ala | Tyr | Gln | Ala | Thr | Leu | Tyr | Gly | Asp | Ser | Asn | Tyr | Thr | Gly | Lys |
|---|---|---|---|---|---|---|---|---|---|---|---|---|---|---|
| 1190 | | | | | 1195 | | | | | 1200 | | | | |

| Ala | Tyr | Asn | Leu | Thr | His | Asn | Val | Ala | Asn | Leu | Lys | Asp | Val | Gly |
|---|---|---|---|---|---|---|---|---|---|---|---|---|---|---|
| 1205 | | | | | 1210 | | | | | 1215 | | | | |

| Met | Asn | Asp | Ile | Val | Ser | Ser | Ile | Lys | Ile | Phe | Ser | Val | | |
|---|---|---|---|---|---|---|---|---|---|---|---|---|---|---|
| 1220 | | | | | 1225 | | | | | 1230 | | | | |

<210> SEQ ID NO 27
<211> LENGTH: 3702
<212> TYPE: DNA
<213> ORGANISM: Artificial
<220> FEATURE:
<223> OTHER INFORMATION: A nucleotide sequence encoding TIC4006_His comprised of a histidine tag coding sequence operably linked 5' to the TIC4006 coding sequence.

<400> SEQUENCE: 27

```
atgcatcacc atcaccatca ccatcaccat cacggtaccg agaccgtccg cttccaatcc      60
atgaatcaat atgttacaac agtgcaaaag gcagttaatg cattattttc aaataatacc     120
ttacccttaa acattactga ttataatata gaccagacag catatcttgt agaacgtata     180
tctaatgata gatattctaa agacaagatg atgttactca atcaagtcaa atttgcgaaa     240
cgtttgagtc gagcgcgtaa cttattgaaa ggtggcgctt ttgaattatc agataagaat     300
agatggaaga caaacaatta tgcgaatatt ttatcaggtt ctctcctatc caaaggccaa     360
tctttaaaca ttctaagcgc aagccctaca gtaagtagtc aaattattcc gactcatgta     420
tatcaaagaa tagatgaatc aaagttaaaa ccatatacac gttatttagt aagagggttc     480
gttgaaaaga gtcgagattt agaactattt gtgctcagat ataacaaaga ggtgtataaa     540
agaatcaatg tacccaagaa tgaggattat catatccact cgcatttaaa tgaagaagag     600
aatccatggc acaataaata tatccaaaac actccggttc aaaattcaat ctctatgcgc     660
aagaattcac atgagtttac gtgtcatatt gatatagggg aactggatat aaagaaagga     720
cctggtataa ccatcggttt tcaaattagc acaacagatg ggatggcaac attagataat     780
atagaagtga tagaagcaca tccgttaact ggagacgatt taacacgtat ccaaaggcgt     840
```

```
gaacgtaaat ggaaacaaaa atggctagag aatcaaatac aaatcgaaaa agctgcacaa    900
acagcgaaag aggcgattaa aaatttattt acatgcccac aacaaaatca attgacctgg    960
atgacaaccc taaacgacat tatacaggca gaaaaattga tacaagagat tccatattgg   1020
tatagccgac ttttaggtga ggatttcccc atactaccag aagaggcata tgacacccgtt  1080
caacaacttt caactgcagt tgaaaccgca aaattgttgt atgcacaacg aaatgtggtg   1140
aataatgggg atttttcaagc tggattttca aattggaata cgaccgatgg tgcagagata  1200
aaacaaattc aggattcatc ttctgttcta gtaattacgg actgggctgc aaatatttca   1260
caggacatgc gtgtggttga aaaggtggc tatctgctgc gcgtaacagc gaaaaaagaa   1320
gatgccggag aaggttatat aacaattagt gattgttccg tagtgatgga aaaattgaca   1380
tttacaacag gggattctgt agagagtctg gcacattctg atatttattc aaggatccat   1440
aagcgctatg ctaaaaaaca aataacaaat catctttcag aaagatatga aatagaatcg   1500
aatcctcatt taattaatag agcggaacaa atgcttcccc tcccttctag ctatgtaacc   1560
aaaacgattg aagtctttcc ggaaaccaat cgagtacgcg ttgaaattgg agaaacaggt   1620
ggaacattta tcgtggaaag tgtcgaattg attcgaatgg aacagatgaa cgaaacaaac   1680
aatccagctg tagatattca aactgtaatg aatgatacac ccgctacaca atttgatcca   1740
gtttctttta cagaatcaac ggtgagtccc agaaatactc aatatgcata ttctcatgat   1800
tcaaatatag gttatgaaaa tcctaactgg atggctgata tttcaggtga tactttatt   1860
agtgatttat ctatccctgg tacacataat acaatggctt tttatggagg agatattaca   1920
caatgtcaaa cgatgtcact gaatacgcaa ttacatgtag gaattcgtta tttagatatt   1980
cgctgtaggc atatcgaaaa tattttttgcg attcatcatg gaattgtgta ccaaaatgcg   2040
acgtttacag atgtttgtat agccgtaaga gattttttga ggaacaaccc tagtgagaca   2100
gtatttatgc ggataaaaga gaacataca gcagaaaata atacaagatc ttttggggag   2160
acatttgcag actataagtc tcaatatagc gacttatttt ggaattggac gggtgataac   2220
ccaagattaa gtgaaataag aggaaaagtt gttgttttgc aaaattttt tggggataaa   2280
tttggtatcg attacaatac actgaataaa caagatcaat atcatttaaa tacaaactgg   2340
gatttatatg ataaatggct atttgtaaaa gaacatttgt atgccgctga cgattcttat   2400
aaaaatggtc gtaaacaagc atatctaaat tatctaagcg ggtcaggtgg ttctttttcct  2460
tatttgttg caagtggaca cagtagtcct ggtacaaatg cttcaaatct atctacaggg   2520
ctaacaacac cggcatttga aagctggtat ccggattttc cacggggaag ttgtttttata   2580
ggaatttgca caatttattt tgaaggaaca atattctta caagtgagtg gatacagaaa   2640
agtgattta aatatgtagg aatcatagct gctgattttc caggaagaac attaatttcc   2700
aatattatta gtctgaataa tcttcttagt ttagaaatta aaaatggtgg tacctatcaa   2760
attgttccg ctttaaataa tagtagtgtt gtagatatga atccaggaga ccaaaatatt   2820
cacttatgga acaataacgg tactgctaat caattatgga aattcgtata taattcaaat   2880
gaattagcat accaaaattaa aagtttatct aatgaaaatt tagtattaac ctgggcttac   2940
aatagtagta atccagataa tgtaattgct gcttccaatc aaaataggtc tgagcaatat   3000
tggatacctg agcgtacggg agcatatcat tattttaaaa atctaagcaa tcgttcggga   3060
gcattagatg taagcggctc agagacaaaa aacggaacaa acattctgta ctggagttat   3120
aaaaaagcaa caaatcaaaa attcaaactg acagaagtaa atgtatctgg aggtcaagct   3180
```

```
gaaggtgtat atttatatgc agatgccaat tatgtagggc aatctgtagg gctaacaaat    3240
agtgtcgcag accttagcga agttggtatg aatgatatag ctagttctat aaaatttatt    3300
ggtccttatc aagctactct atatgagcat gctgatttta aaggtgcggt ttttactccc    3360
acaactaata ttgcaaattt aaaagatgtt ggcatgaatg atacaatcag ctctataaaa    3420
attacaaaga catctggagg ccgagctgca ggtatatatt tatattcgga tgccaattat    3480
gtgggaaggt ctatatggtt aacgtctaat gttgcaaatt taaaagatgt tggcatgaat    3540
gatacaatca gttccgtaga aattgttggc gcatatggag tcactttata tggggatgcc    3600
aattatacag gtaaggctta tgctctcaca tctaatgttg caaatttaaa agatgttggc    3660
atgaatgata tagtcagttc tataaaaatt tttagtgtat aa                       3702
```

<210> SEQ ID NO 28
<211> LENGTH: 1233
<212> TYPE: PRT
<213> ORGANISM: Artificial
<220> FEATURE:
<223> OTHER INFORMATION: The amino acid sequence of TIC4006_His.

<400> SEQUENCE: 28

```
Met His His His His His His His His His Gly Thr Glu Thr Val
1               5                   10                  15

Arg Phe Gln Ser Met Asn Gln Tyr Val Thr Thr Val Gln Lys Ala Val
            20                  25                  30

Asn Ala Leu Phe Ser Asn Asn Thr Leu Pro Leu Asn Ile Thr Asp Tyr
        35                  40                  45

Asn Ile Asp Gln Thr Ala Tyr Leu Val Glu Arg Ile Ser Asn Asp Arg
    50                  55                  60

Tyr Ser Lys Asp Lys Met Met Leu Leu Asn Gln Val Lys Phe Ala Lys
65                  70                  75                  80

Arg Leu Ser Arg Ala Arg Asn Leu Leu Lys Gly Gly Ala Phe Glu Leu
                85                  90                  95

Ser Asp Lys Asn Arg Trp Lys Thr Asn Asn Tyr Ala Asn Ile Leu Ser
            100                 105                 110

Gly Ser Leu Leu Ser Lys Gly Gln Ser Leu Asn Ile Leu Ser Ala Ser
        115                 120                 125

Pro Thr Val Ser Ser Gln Ile Ile Pro Thr His Val Tyr Gln Arg Ile
    130                 135                 140

Asp Glu Ser Lys Leu Lys Pro Tyr Thr Arg Tyr Leu Val Arg Gly Phe
145                 150                 155                 160

Val Glu Lys Ser Arg Asp Leu Glu Leu Phe Val Leu Arg Tyr Asn Lys
                165                 170                 175

Glu Val Tyr Lys Arg Ile Asn Val Pro Lys Asn Glu Asp Tyr His Ile
            180                 185                 190

Thr Ser His Leu Asn Glu Glu Asn Pro Trp His Asn Lys Tyr Ile
        195                 200                 205

Gln Asn Thr Pro Val Gln Asn Ser Ile Ser Met Arg Lys Asn Ser His
    210                 215                 220

Glu Phe Thr Cys His Ile Asp Ile Gly Glu Leu Asp Ile Lys Lys Gly
225                 230                 235                 240

Pro Gly Ile Thr Ile Gly Phe Gln Ile Ser Thr Thr Asp Gly Met Ala
                245                 250                 255

Thr Leu Asp Asn Ile Glu Val Ile Glu Ala His Pro Leu Thr Gly Asp
            260                 265                 270
```

```
Asp Leu Thr Arg Ile Gln Arg Arg Glu Arg Lys Trp Lys Gln Lys Trp
        275                 280                 285
Leu Glu Asn Gln Ile Gln Ile Glu Lys Ala Ala Gln Thr Ala Lys Glu
    290                 295                 300
Ala Ile Lys Asn Leu Phe Thr Cys Pro Gln Gln Asn Gln Leu Thr Trp
305                 310                 315                 320
Met Thr Thr Leu Asn Asp Ile Ile Gln Ala Glu Lys Leu Ile Gln Glu
                325                 330                 335
Ile Pro Tyr Trp Tyr Ser Arg Leu Leu Gly Glu Asp Phe Pro Ile Leu
            340                 345                 350
Pro Glu Glu Ala Tyr Asp Thr Leu Gln Gln Leu Ser Thr Ala Val Glu
        355                 360                 365
Thr Ala Lys Leu Leu Tyr Ala Gln Arg Asn Val Val Asn Asn Gly Asp
    370                 375                 380
Phe Gln Ala Gly Phe Ser Asn Trp Asn Thr Thr Asp Gly Ala Glu Ile
385                 390                 395                 400
Lys Gln Ile Gln Asp Ser Ser Val Leu Val Ile Thr Asp Trp Ala
                405                 410                 415
Ala Asn Ile Ser Gln Asp Met Arg Val Glu Lys Gly Gly Tyr Leu
            420                 425                 430
Leu Arg Val Thr Ala Lys Lys Glu Asp Ala Gly Glu Gly Tyr Ile Thr
        435                 440                 445
Ile Ser Asp Cys Ser Val Val Met Glu Lys Leu Thr Phe Thr Thr Gly
    450                 455                 460
Asp Ser Val Glu Ser Leu Ala His Ser Asp Ile Tyr Ser Arg Ile His
465                 470                 475                 480
Lys Arg Tyr Ala Lys Lys Gln Ile Thr Asn His Leu Ser Glu Arg Tyr
                485                 490                 495
Glu Ile Glu Ser Asn Pro His Leu Ile Asn Arg Ala Glu Gln Asn Ala
            500                 505                 510
Ser Leu Pro Ser Ser Tyr Val Thr Lys Thr Ile Glu Val Phe Pro Glu
        515                 520                 525
Thr Asn Arg Val Arg Val Glu Ile Gly Glu Thr Gly Gly Thr Phe Ile
    530                 535                 540
Val Glu Ser Val Glu Leu Ile Arg Met Glu Gln Met Asn Glu Thr Asn
545                 550                 555                 560
Asn Pro Ala Val Asp Ile Gln Thr Val Met Asn Asp Thr Pro Ala Thr
                565                 570                 575
Gln Phe Asp Pro Val Ser Phe Thr Glu Ser Thr Val Ser Pro Arg Asn
            580                 585                 590
Thr Gln Tyr Ala Tyr Ser His Asp Ser Asn Ile Gly Tyr Glu Asn Pro
        595                 600                 605
Asn Trp Met Ala Asp Ile Ser Gly Asp Thr Leu Phe Ser Asp Leu Ser
    610                 615                 620
Ile Pro Gly Thr His Asn Thr Met Ala Phe Tyr Gly Gly Asp Ile Thr
625                 630                 635                 640
Gln Cys Gln Thr Met Ser Leu Asn Thr Gln Leu His Val Gly Ile Arg
                645                 650                 655
Tyr Leu Asp Ile Arg Cys Arg His Ile Glu Asn Ile Phe Ala Ile His
            660                 665                 670
His Gly Ile Val Tyr Gln Asn Ala Thr Phe Thr Asp Val Cys Ile Ala
        675                 680                 685
Val Arg Asp Phe Leu Arg Asn Asn Pro Ser Glu Thr Val Phe Met Arg
```

-continued

```
            690                 695                 700
Ile Lys Glu Glu His Thr Ala Glu Asn Asn Thr Arg Ser Phe Gly Glu
705                 710                 715                 720

Thr Phe Ala Asp Tyr Lys Ser Gln Tyr Ser Asp Leu Phe Trp Asn Trp
                725                 730                 735

Thr Gly Asp Asn Pro Arg Leu Ser Glu Ile Arg Gly Lys Val Val Val
                740                 745                 750

Leu Gln Asn Phe Phe Gly Asp Lys Phe Gly Ile Asp Tyr Asn Thr Leu
            755                 760                 765

Asn Lys Gln Asp Gln Tyr His Leu Asn Thr Asn Trp Asp Leu Tyr Asp
        770                 775                 780

Lys Trp Leu Phe Val Lys Glu His Leu Tyr Ala Ala Asp Asp Ser Tyr
785                 790                 795                 800

Lys Asn Gly Arg Lys Gln Ala Tyr Leu Asn Tyr Leu Ser Gly Ser Gly
                805                 810                 815

Gly Ser Phe Pro Tyr Phe Val Ala Ser Gly His Ser Ser Pro Gly Thr
                820                 825                 830

Asn Ala Ser Asn Leu Ser Thr Gly Leu Thr Thr Pro Ala Phe Glu Ser
            835                 840                 845

Trp Tyr Pro Asp Phe Pro Arg Gly Ser Cys Phe Ile Gly Ile Cys Thr
        850                 855                 860

Ile Tyr Phe Glu Gly Thr Asn Ile Leu Thr Ser Glu Trp Ile Gln Lys
865                 870                 875                 880

Ser Asp Phe Lys Tyr Val Gly Ile Ile Ala Ala Asp Phe Pro Gly Arg
                885                 890                 895

Thr Leu Ile Ser Asn Ile Ile Ser Leu Asn Asn Leu Leu Ser Leu Glu
            900                 905                 910

Ile Lys Asn Gly Gly Thr Tyr Gln Ile Val Ser Ala Leu Asn Asn Ser
        915                 920                 925

Ser Val Val Asp Met Asn Pro Gly Asp Gln Asn Ile His Leu Trp Asn
930                 935                 940

Asn Asn Gly Thr Ala Asn Gln Leu Trp Lys Phe Val Tyr Asn Ser Asn
945                 950                 955                 960

Glu Leu Ala Tyr Gln Ile Lys Ser Leu Ser Asn Glu Asn Leu Val Leu
                965                 970                 975

Thr Trp Ala Tyr Asn Ser Ser Asn Pro Asp Asn Val Ile Ala Ala Ser
            980                 985                 990

Asn Gln Asn Arg Ser Glu Gln Tyr Trp Ile Pro Glu Arg Thr Gly Ala
        995                 1000                1005

Tyr His Tyr Phe Lys Asn Leu Ser Asn Arg Ser Gly Ala Leu Asp
        1010                1015                1020

Val Ser Gly Ser Glu Thr Lys Asn Gly Thr Asn Ile Leu Tyr Trp
    1025                1030                1035

Ser Tyr Lys Lys Ala Thr Asn Gln Lys Phe Lys Leu Thr Glu Val
    1040                1045                1050

Asn Val Ser Gly Gly Gln Ala Glu Gly Val Tyr Leu Tyr Ala Asp
    1055                1060                1065

Ala Asn Tyr Val Gly Gln Ser Val Gly Leu Thr Asn Ser Val Ala
    1070                1075                1080

Asp Leu Ser Glu Val Gly Met Asn Asp Ile Ala Ser Ser Ile Lys
    1085                1090                1095

Phe Ile Gly Pro Tyr Gln Ala Thr Leu Tyr Glu His Ala Asp Phe
    1100                1105                1110
```

-continued

```
Lys Gly Ala Val Phe Thr Pro Thr Thr Asn Ile Ala Asn Leu Lys
    1115            1120            1125

Asp Val Gly Met Asn Asp Thr Ile Ser Ser Ile Lys Ile Thr Lys
    1130            1135            1140

Thr Ser Gly Gly Arg Ala Ala Gly Ile Tyr Leu Tyr Ser Asp Ala
    1145            1150            1155

Asn Tyr Val Gly Arg Ser Ile Trp Leu Thr Ser Asn Val Ala Asn
    1160            1165            1170

Leu Lys Asp Val Gly Met Asn Asp Thr Ile Ser Ser Val Glu Ile
    1175            1180            1185

Val Gly Ala Tyr Gly Val Thr Leu Tyr Gly Asp Ala Asn Tyr Thr
    1190            1195            1200

Gly Lys Ala Tyr Ala Leu Thr Ser Asn Val Ala Asn Leu Lys Asp
    1205            1210            1215

Val Gly Met Asn Asp Ile Val Ser Ser Ile Lys Ile Phe Ser Val
    1220            1225            1230
```